United States Patent
Akin et al.

(10) Patent No.: US 7,892,246 B2
(45) Date of Patent: Feb. 22, 2011

(54) DEVICES AND METHODS FOR INTERCONNECTING CONDUITS AND CLOSING OPENINGS IN TISSUE

(75) Inventors: Jodi J. Akin, Alamo, CA (US); Stephen R. Ramee, New Orleans, LA (US)

(73) Assignee: BioConnect Systems, Inc., Ambler, PA (US)

( * ) Notice: Subject to any disclaimer, the term of this patent is extended or adjusted under 35 U.S.C. 154(b) by 1587 days.

(21) Appl. No.: 10/235,948

(22) Filed: Sep. 4, 2002

(65) Prior Publication Data
US 2003/0100920 A1    May 29, 2003

Related U.S. Application Data

(63) Continuation-in-part of application No. 09/771,007, filed on Jan. 26, 2001, now Pat. No. 6,458,140, and a continuation-in-part of application No. PCT/US00/20588, filed on Jul. 28, 2000, which is a continuation-in-part of application No. 09/363,309, filed on Jul. 28, 1999, now Pat. No. 6,251,116, which is a continuation-in-part of application No. 09/363,310, filed on Jul. 28, 1999, now Pat. No. 6,165,185.

(51) Int. Cl.
*A61B 17/04* (2006.01)
*A61M 29/00* (2006.01)
(52) U.S. Cl. ........................ 606/155; 606/153
(58) Field of Classification Search .......... 606/213, 606/151, 153, 154, 155, 191, 194; 623/1.15
See application file for complete search history.

(56) References Cited

U.S. PATENT DOCUMENTS 2,127,903 A    8/1938   Bowen
(Continued)

FOREIGN PATENT DOCUMENTS

EP    0894475    2/1999
(Continued)

OTHER PUBLICATIONS

International Search Report for PCT/US02/03919 dated Dec. 12, 2002.
(Continued)

*Primary Examiner*—Vy Q Bui
(74) *Attorney, Agent, or Firm*—Kilpatrick Townsend & Stockton LLP

(57) ABSTRACT

The subject invention provides devices and methods for closing and sealing an opening in a conduit. The subject devices consist of an implantable flexible member adapted to conform to and seal with an inner surface of a conduit and further adapted to utilize the internal conduit pressure exerted thereon to form a substantially fluid-tight seal with the inner surface of the conduit whereby substances are prevented from leaking from the opening under normal physiological conditions. In the subject methods, a subject device is provided and positioned inside a conduit, operatively aligned over an opening to be sealed. The device is conformed to and sealed with an inner surface of the conduit and a substantially fluid-tight seal is formed between the device and the inner surface of the conduit utilizing the internal conduit pressure whereby substances within the conduit are prevented from leaking from the opening under normal physiological conditions.

41 Claims, 25 Drawing Sheets

U.S. PATENT DOCUMENTS

| | | |
|---|---|---|
| 3,974,835 A | 8/1976 | Hardy, Jr. |
| 4,352,358 A | 10/1982 | Angelchik |
| 4,366,819 A | 1/1983 | Kaster |
| 4,368,736 A | 1/1983 | Kaster |
| 4,667,673 A | 5/1987 | Li |
| 4,705,040 A | 11/1987 | Mueller et al. |
| 4,744,364 A | 5/1988 | Kensey |
| 4,787,386 A | 11/1988 | Walsh et al. |
| 4,852,568 A | 8/1989 | Kensey |
| 4,890,612 A | 1/1990 | Kensey |
| 5,061,274 A | 10/1991 | Kensey |
| 5,108,421 A | 4/1992 | Fowler |
| 5,141,516 A | 8/1992 | Detweiler |
| 5,192,302 A | 3/1993 | Kensey et al. |
| 5,197,976 A * | 3/1993 | Herweck et al. ............ 623/1.27 |
| 5,222,974 A | 6/1993 | Kensey et al. |
| 5,282,827 A | 2/1994 | Kensey et al. |
| 5,330,445 A | 7/1994 | Haaga |
| 5,453,090 A | 9/1995 | Martinez et al. |
| 5,456,714 A | 10/1995 | Owen |
| 5,503,635 A | 4/1996 | Sauer et al. |
| 5,549,633 A | 8/1996 | Evans et al. |
| 5,586,987 A | 12/1996 | Fahy |
| 5,620,461 A | 4/1997 | VanDe Moer et al. |
| 5,634,936 A | 6/1997 | Linden et al. |
| 5,649,959 A | 7/1997 | Hannam et al. |
| 5,669,924 A | 9/1997 | Shaknovich |
| 5,676,670 A | 10/1997 | Kim |
| 5,683,451 A | 11/1997 | Lenker et al. |
| 5,716,325 A | 2/1998 | Bonutti |
| 5,728,134 A | 3/1998 | Barak |
| 5,796,178 A | 8/1998 | Onuma |
| 5,830,222 A | 11/1998 | Makower |
| 5,853,422 A | 12/1998 | Huebsch et al. |
| 5,868,761 A | 2/1999 | Nicholas et al. |
| 5,868,763 A | 2/1999 | Spence et al. |
| 5,868,777 A | 2/1999 | Lam |
| 5,893,886 A | 4/1999 | Zegdi et al. |
| 5,921,995 A | 7/1999 | Kleshinski |
| 6,007,544 A | 12/1999 | Kim |
| 6,007,576 A | 12/1999 | McClellan |
| 6,017,352 A | 1/2000 | Nash et al. |
| 6,030,395 A | 2/2000 | Nash et al. |
| 6,036,702 A | 3/2000 | Bachinski et al. |
| 6,036,705 A | 3/2000 | Nash et al. |
| 6,056,762 A | 5/2000 | Nash et al. |
| 6,063,114 A | 5/2000 | Nash et al. |
| 6,068,638 A | 5/2000 | Makower |
| 6,068,654 A | 5/2000 | Berg et al. |
| 6,077,291 A | 6/2000 | Das |
| 6,113,612 A | 9/2000 | Swanson et al. |
| 6,117,145 A | 9/2000 | Wood et al. |
| 6,152,945 A | 11/2000 | Bachinski et al. |
| 6,165,185 A | 12/2000 | Shennib et al. |
| 6,171,329 B1 | 1/2001 | Shaw et al. |
| 6,176,864 B1 | 1/2001 | Chapman |
| 6,190,353 B1 | 2/2001 | Makower et al. |
| 6,190,397 B1 | 2/2001 | Spence et al. |
| 6,193,734 B1 | 2/2001 | Bolduc et al. |
| 6,206,893 B1 | 3/2001 | Klein et al. |
| 6,206,913 B1 | 3/2001 | Yencho et al. |
| 6,214,022 B1 | 4/2001 | Taylor et al. |
| 6,214,029 B1 | 4/2001 | Thill et al. |
| 6,217,585 B1 | 4/2001 | Houser et al. |
| 6,231,587 B1 | 5/2001 | Makower |
| 6,241,741 B1 | 6/2001 | Duhaylongsod et al. |
| 6,241,768 B1 | 6/2001 | Agarwal et al. |
| 6,251,116 B1 | 6/2001 | Shennib et al. |
| 6,254,630 B1 | 7/2001 | Inoue |
| 6,270,515 B1 | 8/2001 | Linden et al. |
| 6,283,983 B1 | 9/2001 | Makower et al. |
| 6,302,905 B1 | 10/2001 | Goldsteen et al. |
| 6,350,280 B1 | 2/2002 | Nash et al. |
| 6,371,965 B2 | 4/2002 | Gifford, III et al. |
| 6,395,019 B2 * | 5/2002 | Chobotov .................. 623/1.13 |
| 6,402,767 B1 | 6/2002 | Nash et al. |
| 6,409,739 B1 | 6/2002 | Nobles et al. |
| 6,419,681 B1 | 7/2002 | Vargas et al. |
| 6,428,550 B1 | 8/2002 | Vargas et al. |
| 6,440,163 B1 | 8/2002 | Swanson et al. |
| 6,443,965 B1 | 9/2002 | Gifford, III et al. |
| 6,458,140 B2 | 10/2002 | Akin et al. |
| 6,461,320 B1 | 10/2002 | Yencho et al. |
| 6,464,709 B1 | 10/2002 | Shennib et al. |
| 6,485,496 B1 | 11/2002 | Suyker et al. |
| 6,497,710 B2 | 12/2002 | Yencho et al. |
| 6,508,824 B1 | 1/2003 | Flaherty et al. |
| 6,517,558 B2 * | 2/2003 | Gittings et al. .............. 606/153 |
| 6,537,287 B1 | 3/2003 | Yencho et al. |
| 6,537,288 B2 | 3/2003 | Vargas et al. |
| 6,565,581 B1 | 5/2003 | Spence et al. |
| 6,585,762 B1 | 7/2003 | Stanish |
| 6,589,277 B1 | 7/2003 | Fabiani et al. |
| 6,616,675 B1 | 9/2003 | Evard et al. |
| 6,620,129 B2 | 9/2003 | Stecker et al. |
| 6,626,920 B2 | 9/2003 | Whayne |
| 6,626,939 B1 * | 9/2003 | Burnside et al. ........... 623/1.38 |
| 6,652,543 B2 | 11/2003 | Spence et al. |
| 6,655,386 B1 | 12/2003 | Makower et al. |
| 6,695,875 B2 | 2/2004 | Stelter et al. |
| 6,699,257 B2 | 3/2004 | Gifford, III et al. |
| 6,709,441 B2 | 3/2004 | Bolduc et al. |
| 6,712,831 B1 | 3/2004 | Kaplan et al. |
| 6,719,781 B1 | 4/2004 | Kim |
| 6,726,697 B2 | 4/2004 | Nicholas et al. |
| 6,736,825 B2 | 5/2004 | Blatter et al. |
| 6,740,101 B2 | 5/2004 | Houser et al. |
| 6,776,785 B1 | 8/2004 | Yencho et al. |
| 6,786,914 B1 | 9/2004 | Vargas et al. |
| 6,790,229 B1 | 9/2004 | Berreklouw |
| 6,913,607 B2 | 7/2005 | Ainsworth et al. |
| 6,916,327 B2 | 7/2005 | Northrup, III et al. |
| 6,926,724 B1 | 8/2005 | Chu |
| 6,962,596 B2 | 11/2005 | Bolduc et al. |
| 6,972,023 B2 | 12/2005 | Whayne et al. |
| 7,008,436 B2 | 3/2006 | Barath |
| 7,018,388 B2 | 3/2006 | Yencho et al. |
| 7,025,773 B2 | 4/2006 | Gittings et al. |
| 7,029,482 B1 | 4/2006 | Vargas et al. |
| 7,041,110 B2 | 5/2006 | Yencho et al. |
| 7,063,712 B2 | 6/2006 | Vargas et al. |
| 7,128,749 B1 | 10/2006 | Vargas et al. |
| 7,160,311 B2 | 1/2007 | Blatter et al. |
| 7,172,608 B2 | 2/2007 | Vargas et al. |
| 7,175,637 B2 | 2/2007 | Vargas et al. |
| 2001/0004699 A1 * | 6/2001 | Gittings et al. .............. 606/153 |
| 2001/0047165 A1 | 11/2001 | Makower et al. |
| 2001/0049539 A1 | 12/2001 | Rehil |
| 2002/0022853 A1 | 2/2002 | Swanson et al. |
| 2002/0029079 A1 | 3/2002 | Kim et al. |
| 2002/0091398 A1 | 7/2002 | Galdonik et al. |
| 2003/0065344 A1 | 4/2003 | Kirsch et al. |
| 2003/0212418 A1 | 11/2003 | Yencho et al. |
| 2003/0229365 A1 | 12/2003 | Whayne et al. |
| 2003/0236542 A1 | 12/2003 | Makower |
| 2004/0024345 A1 | 2/2004 | Gharib et al. |
| 2004/0073282 A1 | 4/2004 | Stanish |
| 2004/0097991 A1 | 4/2004 | Makower |
| 2004/0088042 A1 | 5/2004 | Kim et al. |
| 2004/0102796 A1 | 5/2004 | Hill et al. |
| 2004/0122318 A1 | 6/2004 | Flaherty et al. |
| 2004/0133225 A1 | 7/2004 | Makower |
| 2004/0158143 A1 | 8/2004 | Flaherty et al. |
| 2004/0249400 A1 | 12/2004 | Vargas et al. |

| | | | |
|---|---|---|---|
| 2004/0260318 A1 | 12/2004 | Hunter et al. | |
| 2005/0043751 A1 | 2/2005 | Phan et al. | |
| 2005/0043752 A1 | 2/2005 | Phan et al. | |
| 2005/0137614 A1 | 6/2005 | Porter et al. | |
| 2005/0149073 A1 | 7/2005 | Arani et al. | |
| 2005/0165426 A1 | 7/2005 | Manzo | |
| 2005/0251187 A1 | 11/2005 | Beane et al. | |
| 2006/0064119 A9 | 3/2006 | Tilson et al. | |
| 2006/0241342 A1 | 10/2006 | Macaulay et al. | |

FOREIGN PATENT DOCUMENTS

| | | |
|---|---|---|
| JP | 03-018355 | 1/1991 |
| JP | 9-511409 | 11/1997 |
| JP | 02003220065 | 8/2003 |
| WO | WO 90/14796 | 12/1990 |
| WO | 9514442 | 6/1995 |
| WO | 9727898 | 8/1997 |
| WO | 9802099 | 1/1998 |
| WO | 9807399 | 2/1998 |
| WO | 9816174 | 4/1998 |
| WO | 9819629 | 5/1998 |
| WO | 9819636 | 5/1998 |
| WO | 9840036 | 9/1998 |
| WO | 9852471 | 11/1998 |
| WO | 9852474 | 11/1998 |
| WO | WO 99/08603 | 2/1999 |
| WO | 9911180 | 3/1999 |
| WO | 9948427 | 9/1999 |
| WO | 0027310 | 5/2000 |
| WO | 0027313 | 5/2000 |
| WO | 0041633 | 7/2000 |
| WO | 0053104 | 9/2000 |
| WO | WO 00/69365 | 11/2000 |
| WO | 0139672 | 6/2001 |
| WO | 0141653 | 6/2001 |

OTHER PUBLICATIONS

"International Preliminary Report on Patentability," issued by The International Bureau of WIPO in connection with International Patent Application No. PCT/US2008/072166, on Feb. 2, 2010 (11 pages).

"International Preliminary Report on Patentability," issued by The International Bureau of WIPO in connection with International Patent Application No. PCT/US2008/072167, on Feb. 2, 2010 (18 pages).

* cited by examiner

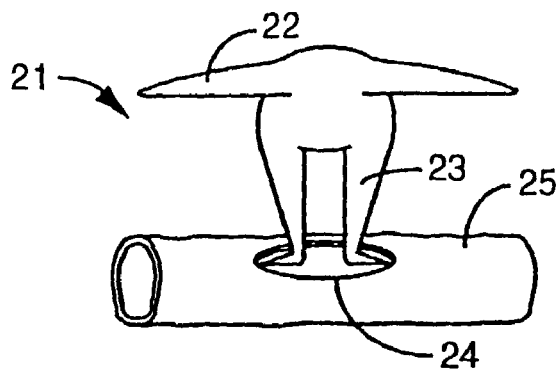
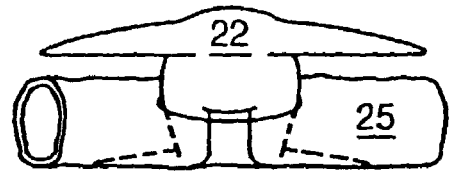
FIG. 4A
FIG. 4B
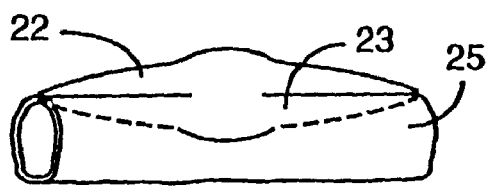
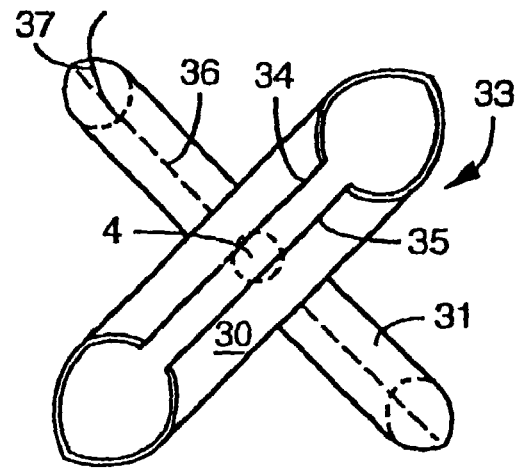
FIG. 4C
FIG. 5
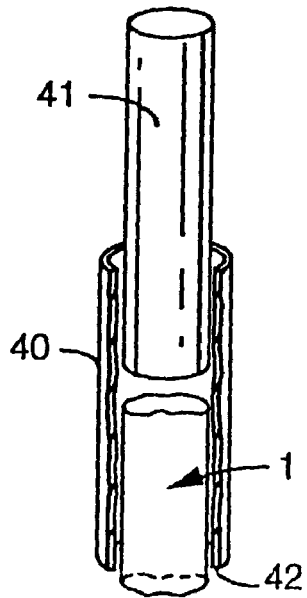
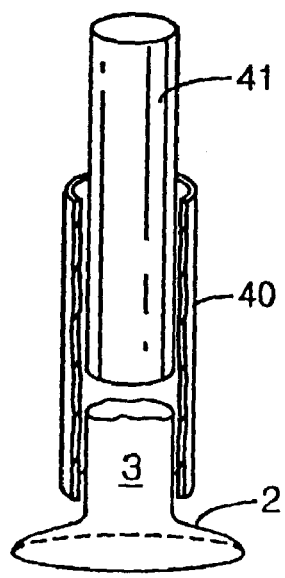
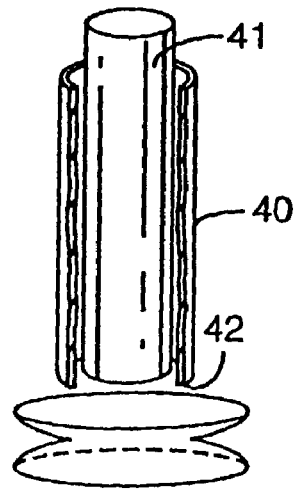
FIG. 6A
FIG. 6B
FIG. 6C

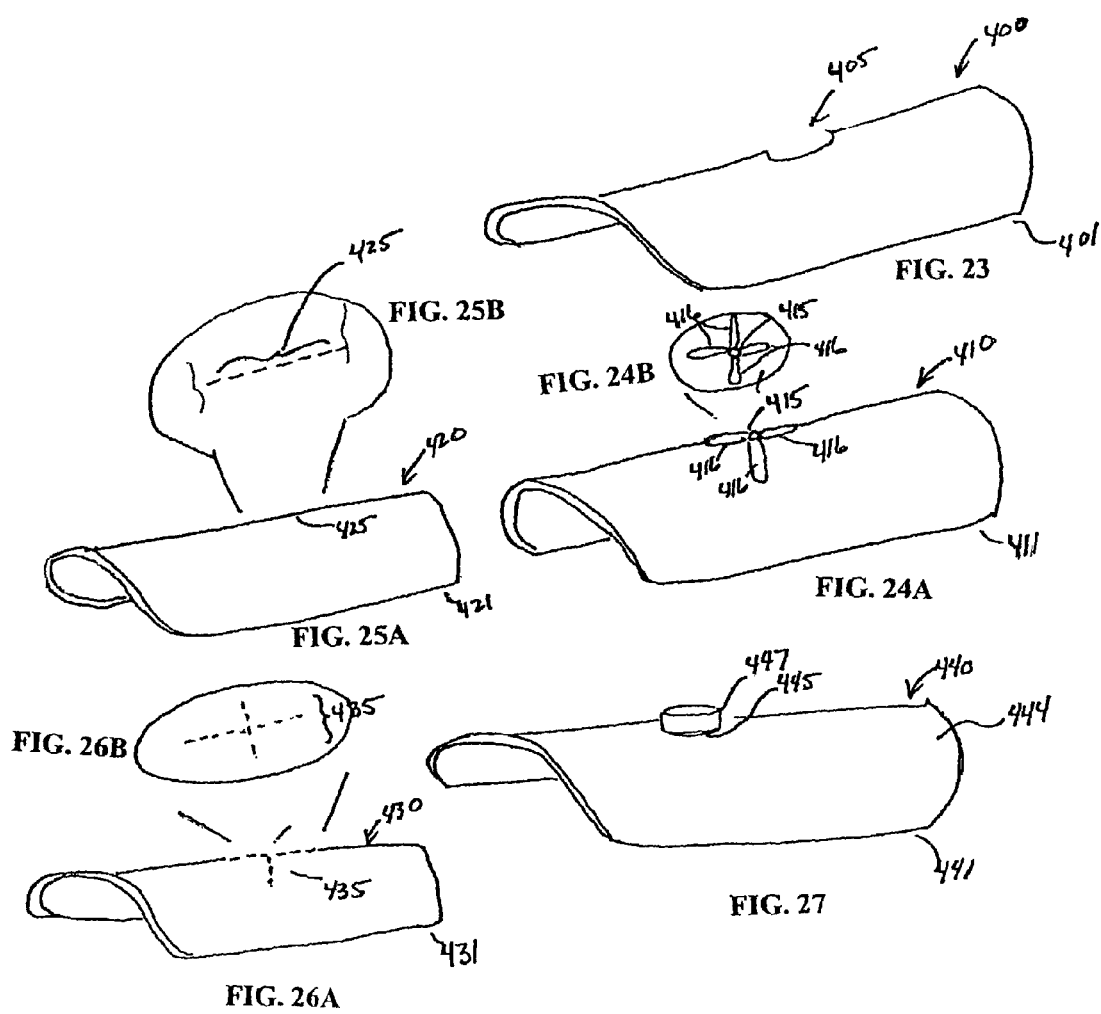

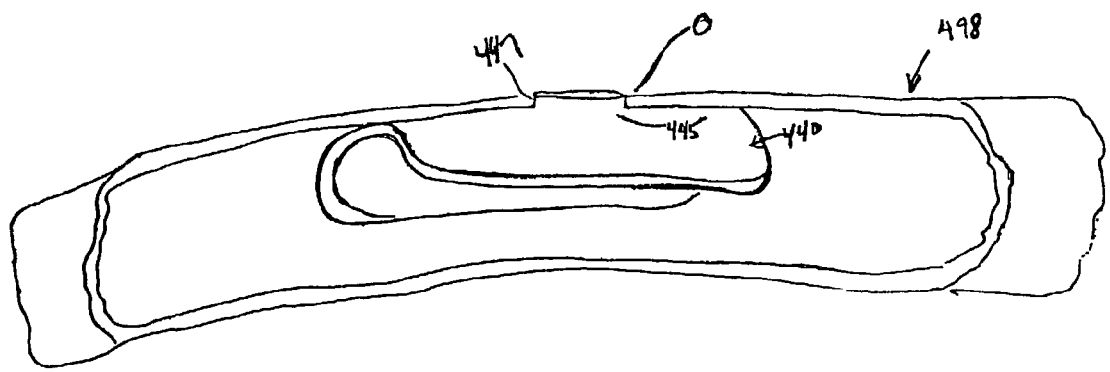
FIG. 28
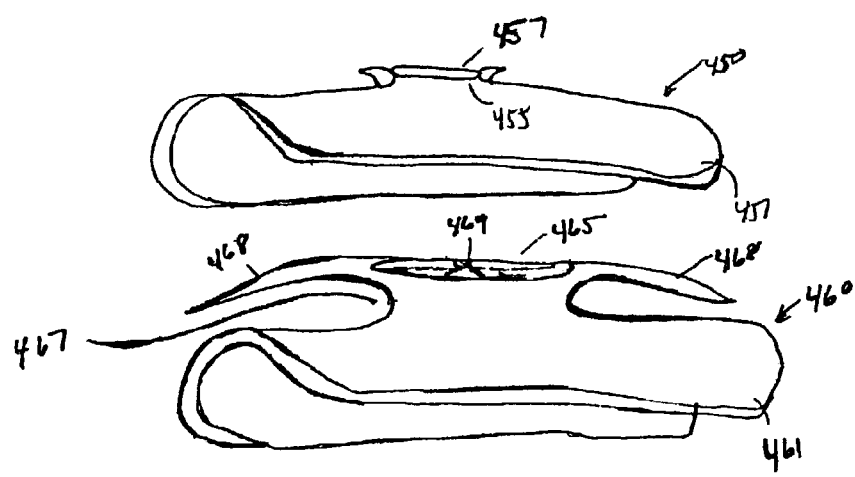
FIG. 29
FIG. 30

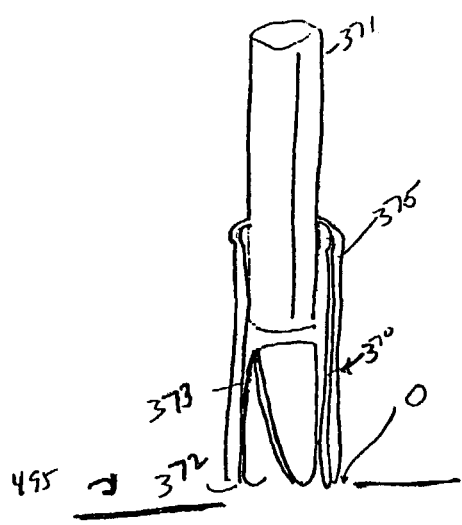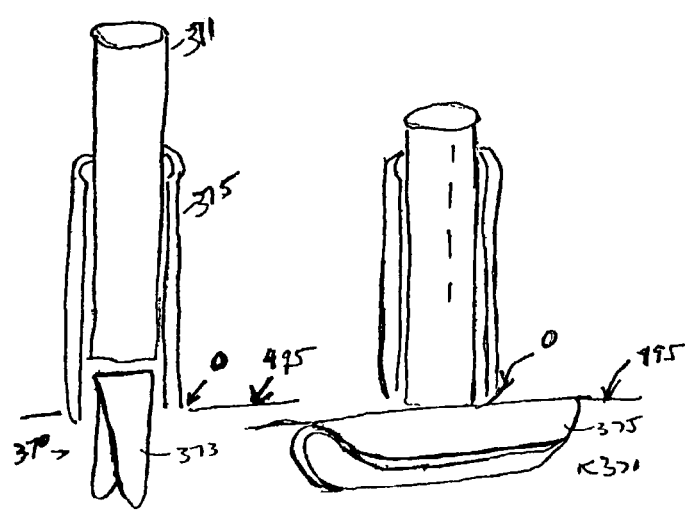
FIG. 35A
FIG. 35B
FIG. 35C

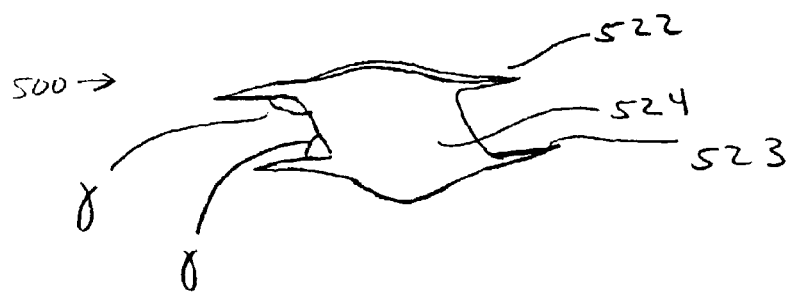
FIG. 36A
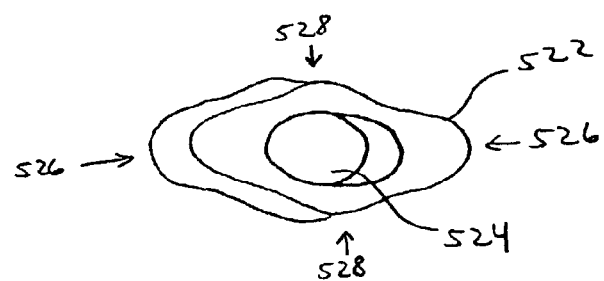
FIG. 36B
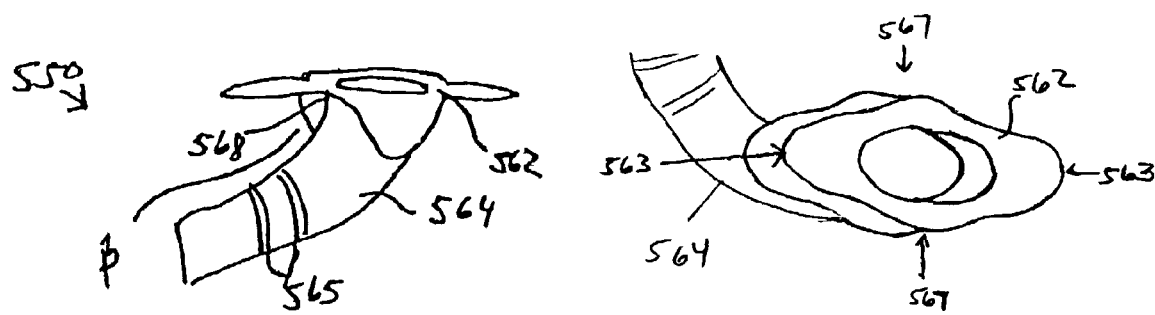
FIG. 37A
FIG. 37B

DEVICES AND METHODS FOR INTERCONNECTING CONDUITS AND CLOSING OPENINGS IN TISSUE

CROSS-REFERENCE TO RELATED APPLICATIONS

This application is a continuation-in-part of application Ser. No. 09/771,007 filed on Jan. 26, 2001, which is a continuation-in-part of application serial no. PCT/US00/20588 filed on Jul. 28, 2000; which application is a continuation-in-part of application Ser. No. 09/363,309 filed on Jul. 28, 1999 and application Ser. No. 09/363,310 filed on Jul. 28, 1999, now U.S. Pat. No. 6,165,185 issued on Dec. 26, 2000; the disclosures of which are herein incorporated by reference.

INTRODUCTION

1. Technical Field

The field of this invention is related to the interconnection of conduits and the closure of openings within tissue.

2. Background of the Invention

The human body has numerous vessels carrying fluid to essential tissues and areas for recirculation or excretion. When vessels become damaged, severed or wholly occluded due to physiological problems, certain sections must be bypassed to allow for the free and continuous flow of fluids. Anastomosis is performed for the purpose of connecting different conduits together to optimize or redirect flow. In cardiac surgery, anastomosis is done to bypass the occluded vessel by harvesting a member of an unobstructed vessel and joining it to the occluded vessel below the point of stenosis.

The common procedure for performing the anastomosis during bypass surgery requires the use of very small sutures, loupes and microsurgical techniques. Surgeons must delicately sew the vessels together being careful not to suture too tightly so as to tear the delicate tissue, thereby injuring the vessel which may then result in poor patency of the anastomosis. Recently, some surgeons have used staples and associated stapling mechanisms and techniques to form an anastomosis, but many of the same difficulties and problems have presented themselves. Basically, the tension and/or compression forces exerted on the vessel walls as a result of suturing and stapling can result in damage to the vessel wall, even to the extent of causing tissue necrosis. Damage to the intima of a vessel is particularly problematic as it may inhibit the natural bonding process that occurs between the anastomized vessels and which is necessary for sufficient patency. Furthermore, damaged vessel walls are likely to have protuberances that when exposed to the bloodstream could obstruct blood flow or may produce turbulence which can lead to formation of thrombus, stenosis and possible occlusion of the artery.

As cardiac surgery is moving into less invasive procedures, surgical access is being reduced, forcing surgeons to work in constantly smaller surgical fields. The procedures are made more difficult due to the multiple characteristics that are unique to each anastomosis and to each patient. For example, the arteries' internal diameter dimensions are difficult to predict and the inside walls are often covered with deposits of stenotic plaque which creates the risk of dislodging plaque into the patient's blood stream during the anastomosis procedure. The resulting emboli in turn create a greater risk of stroke for the patient. The dislodgement of plaque is most likely to occur when the vessel wall undergoes trauma such as the puncturing, compression and tension exerted on the vessel by suturing and stapling. The vessel walls can also be friable and easy to tear, and are often covered with layers of fat and/or are deeply seated in the myocardium, adding to the difficulty of effectively and safely performing conventional anastomotic procedures.

Cardiac surgeons sometimes inadvertently suture too loosely, resulting in leakage of fluid from the anastomosis. In addition to creating a surgical field in which it is difficult to see, leakage of fluid from the anastomosis can cause serious drops in blood pressure, acute or chronic. The loss of blood may cause other deleterious effects on the patient's hemodynamics that may even endanger the patient's life. In addition, blood loss may induce local scar tissue to develop which often results in further blockage within or damage to the sewn vessel. Furthermore, anastomosing blood vessels may involve risks of physical injury to the patient. For example, when performing coronary artery bypass grafting (CABG) procedures, anastomosis often requires manipulation of the heart, so that surgeons may access the back of the heart as well as the front. When done on a beating heart, this manipulation may result in hemodynamic compromise possibly subjecting the patient to cardiac arrest, particularly during lengthy procedures. In "stopped heart" procedures, patients are supported by cardiopulmonary bypass and, thus, risk post-surgical complications (e.g., stroke) that vary directly with the duration for which the heart is under cardioplegic arrest. Consequently, surgeons are constantly searching for techniques to both reduce the risk of tissue damage as well as the laborious and time-consuming task of vessel suturing.

Stapling and coupling procedures have been used in performing large conduit anastomosis. While stapling is successful in gastrointestinal procedures due to the large size and durability of the vessels, as briefly mentioned above, it is less adequate for use in vascular anastomosis. The manufacturing of stapling instruments small enough to be useful for anastomosing smaller vessels, such as coronary arteries, is very difficult and expensive. As stapling instruments are typically made of at least some rigid and fixed components, a stapler of one size will not necessarily work with multiple sizes of vessels. This requires a surgeon to have on hand at least several stapling instruments of varying sizes. This may significantly raise the cost of the equipment and ultimately the cost of the procedure.

When staples are adapted to conform to the smaller sized vessels, they are difficult to maneuver and require a great deal of time, precision, and fine movement to successfully approximate the vessel tissue. Often stapling or coupling devices require the eversion of the vessel walls to provide intima-to-intima contact between the anastomosed vessels. Everting may not always be practical especially for smaller arteries because of the likelihood of tearing when everted. Another factor which may lead to damage or laceration of the vessel and/or leakage at the anastomosis site is the variability of the force that a surgeon may use to fire a stapling instrument causing the possible over- or under-stapling of a vessel. Still other factors include the unintended inversion of the vessel edges and the spacing between staple points. Rectifying a poorly stapled anastomosis is itself a complicated, time-consuming process which can further damage a vessel.

The creation of an arteriovenous (AV) fistula is another instance where two conduits are joined together and involves surgically joining an artery to a vein. AV fistulas are formed for a variety of reasons, one being to provide vascular access for hemodialysis patients. In such a context, the most common site for creation of the AV fistula is at the wrist using a cephalic vein and radial artery, however other locations are used as well, e.g., the upper arm, etc. Another method for hemodialysis vascular access involves the use of Brachio-basilic vein AV fistula.

Regardless of the method or site employed to create the AV fistula, the most common method of creating the fistula uses sutures to anastomose the vein and the artery. This procedure is difficult to perform and time consuming, the difficulty compounded by the small sizes of the vessels involved. Furthermore, anastomosing the vein and artery together using sutures suffers from many of the problems described above with respect to suturing, such as suturing too loosely, suturing too tightly, inducing scar tissue, damaging the vessel, and the like.

Regardless of the reason for interconnecting conduits, openings in the conduit created for carrying out the anastomosis procedure must eventually be closed and sealed. However, it is not just in the context of interconnecting two or more vessels where vessel walls are opened and require subsequent closure. For example, in a carotid endardarectomy procedure, the carotid artery wall is incised in order to remove obstructions within the carotid artery and is then closed by means of hand suturing. Furthermore, many therapeutic and diagnostic procedures are performed intravascularly, wherein a site in a vessel remote from the target site is incised at a convenient location, e.g., the femoral artery in the groin area, to provide an opening in the vessel for the introduction and delivery of interventional instrumentation, such as guide wires, catheters, embolic protection devices, anastomotic devices, stents, and the like, for the percutaneous treatment or diagnosis of a diseased or damaged area of the vasculature or within the heart. Accordingly, one or more openings in a vessel and/or tissue are created to provide an access point for surgical instruments used in a procedure that may be distant from the access point.

In the context of coronary and peripheral surgeries for example, coronary and other vascular catheters, as well as other surgical instruments, may be introduced into the patient's vasculature through the opening and used at a site that is at a distance from the access point. Vascular access is usually established using the well known Seldinger technique as described, for example, in William Grossman's "Cardiac Catheterization and Angiography," 3rd Ed., Lea and Febiger, Philadelphia, 1986, incorporated herein by reference.

Such procedures begin by introducing a small gauge hollow needle through the skin to a target blood vessel or directly into the target vessel where a "cut-down" is used, such as the femoral artery in the region of the patient's groin. A guide wire is then introduced through the needle to a target site within the body and the needle is withdrawn over the guide wire. An introducer sheath is next introduced over the guide wire and both the sheath and guide wire are left in place to provide access to the femoral artery and points accessible therefrom during the surgical procedure. Exemplary procedures performed through this approach include diagnostic procedures such as angiography, ultrasound imaging, etc., and interventional procedures such as angioplasty, atherectomy, stent placement, laser ablation, graft placement, femoro-popletial bypass, arteriovenous fistula formation, CABG, and the like.

When vascular access is no longer required, the instruments (catheter(s), guide wire, introducer sheath and other surgical instruments used) are removed from the patient's vasculature. Accordingly, it is necessary to close the vascular opening to provide hemostasis (i.e., to stop blood loss) and allow the site to heal. However, devices and methods currently used to close openings in vessels have not been wholly satisfactory.

For example, as mentioned above, in carotid endardarectomy procedures, an opening in the carotid artery wall is created to so that a carotid endardarectomy may be performed, i.e., obstructions within the carotid artery may be removed, which opening is then closed by means of hand suturing. Such hand suturing is time consuming, requires a prolonged healing time and often does not provide complete patency.

Another common approach for vessel closure, for example to close a femoral artery access site at the groin, involves applying external force near and upstream from the puncture site, typically by manual or "digital" compression, in order to create hemostasis. This approach suffers from a number of disadvantages. First, the pressure application technique may fail to prevent hemorrhage. Such a hemorrhage may be a life-threatening hemorrhage or lead to a large hematoma. A large hematoma in the groin, for instance, may compromise the major nerve supply to the anterior lower extremity. Additionally, the digital compression method is time-consuming, frequently requiring one-half hour or more of compression before hemostasis is assured, and is very uncomfortable for the patient and frequently requires administering analgesics to be tolerable. For example, a PTCA may be completed in 2 to 3 hours, but the patient will typically be hospitalized for several additional hours or overnight, simply to allow the access site to seal physiologically. During this extended hospital stay the patient is required to stay immobile, often with a sand bag taped to his thigh (in the case of femoral artery access). During this recumbent time, renewed bleeding may occur resulting in bleeding through the tract, hematoma and/or pseudoaneurism formation as well as arteriovenous fistula formation. Moreover, the application of excessive pressure can at times totally occlude the underlying blood vessel, resulting in ischemia and/or thrombosis. Thus, the increased length of in-hospital stay necessitated by the pressure application technique considerably increases the expense of procedures requiring such vascular access. These complications may require blood transfusion and/or surgical intervention. The incidence of these complications increases when the sheath size is increased and when the patient is anticoagulated. It is clear that the standard technique for arterial closure can be risky and is expensive and onerous to the patient.

To overcome the problems associated with manual compression, bioabsorbable fasteners have been proposed. In this approach, bioabsorbable material, such as collagen, is placed at the superficial arterial wall over the puncture site. While potentially effective, this approach suffers from a number of problems. It can be difficult to properly locate the interface of the overlying tissue and the adventitial surface of the blood vessel, and locating the fastener too far from that surface can result in failure to provide hemostasis and subsequent hematoma and/or pseudo aneurism formation. Conversely, if the fastener intrudes into the arterial lumen, intravascular clots and/or collagen pieces with thrombus attached can form and embolize downstream causing vascular occlusion. Also, thrombus formation on the surface of a fastener protruding into the lumen can cause a stenosis which can obstruct normal blood flow. Other possible complications include infection as well as adverse reactions to the collagen implant.

There are still other vascular closure devices and techniques which obviate many of the disadvantages just mentioned, such as the automated suturing devices disclosed in U.S. Pat. Nos. 5,860,991, 6,036,699 and 6,206,893. However, these devices involve complex componentry and require much precision on the part of the user in order to achieve an acceptable vessel closure.

Attempts have been made to minimize the componentry involved in devices for vascular closure. U.S. Pat. No. 5,620, 461 describes a vascular sealing device that is made of a flexible sheet material attached to a fixation element such as a thread. In use, the flexible sheet is inserted through the opening in the vessel and fit around the opening to seal it. The flexible sheet is held in position over the opening by the thread, which is then sutured to the skin to anchor it in place. The flexible sheet and thread are preferably made of bioabsorbable material such that these components disappear after time as they are absorbed by the body. In certain embodiments, the device also includes an arresting element such as a ring that is placed around the thread and engages with the outer surface of the vessel to hold the flexible member in a fixed position.

However, the device described in the '461 patent suffers from significant disadvantages. First and foremost, the effectiveness of such a device is dependent upon the proper placement and securement of the fixation or thread element to the skin by way of suturing. For example, if the thread element is secured too tightly to the skin, excess tension may be created on the vessel which may result in blood leakage from the opening and damage to the vessel wall. Such vessel wall damage may result in ischemia and/or thrombus forming at the site which can dislodge and potentially be life-threatening. On the other hand, if the thread element is secured too loosely to the skin, the flexible member may not be held in proper alignment over the opening, thereby enabling blood to leak from the opening. Still further, if the wall of the vessel is compressed too tightly between the flexible member and the ring, the vessel wall may be damaged resulting in ischemia and the like.

Accordingly, there is a need for an easier, safer and more efficient means for forming anastomotic connections and providing closure of openings within tissue which requires less time and access space than conventional procedures. Of particular interest are devices which are permanently implantable and which are held in a fixed positioned relative to the vessel openings to be interconnected or closed by passive means so that the positioning of the device, and thus the integrity of the seal at the opening, is not dependent upon a secondary element such as a fixation element or other device which compresses, staples or places tension on the adjacent tissue.

Relevant Literature

U.S. patents of interest include: U.S. Pat. Nos. 6,113,612; 6,113,611; 6,090,136; 6,068,656; 6,068,637; 6,063,114; 6,056,762; 6,036,705; 6,036,704; 6,036,703; 6,036,702; 6,030,392; 6,026,814; 6,007,576; 6,007,544; 6,001,123; 5,961,545; 5,948,018; 5,921,995; 5,916,226; 5,904,697; and 4,214,586. Also of interest are the following PCT publications: WO 00/24339; WO 99/65409; WO 99/48427; WO 99/45852; WO 99/08603; WO 98/52474; WO 98/40036; WO 97/31591 and WO 97/31590.

BRIEF DESCRIPTION OF THE DRAWINGS

FIG. 4 includes FIGS. 4A, 4B and 4C all of which show a alternative side-to-side embodiment of the invention with FIG. 4A showing a first segment of the device in a completely folded form being inserted within an opening in a vessel, FIG. 4B showing the first segment partially unfolded and further inserted within the vessel and FIG. 4C showing the first segment completely unfolded and completely inserted within the vessel;

FIG. 5 shows an alternative side-to-side embodiment of the invention where the first and second segments are connected in a manner such that each segment is at a right angle or perpendicular to the other segment;

FIG. 6 includes FIGS. 6A, 6B and 6C each of which show an alternative side-to-side embodiment of the invention being delivered by a surgical dispenser and inserted into a vessel with FIG. 6A showing the device almost completely inserted within the surgical dispenser lumen, FIG. 6B showing the device partially extruded from the surgical dispenser lumen and FIG. 6C showing the device completely extruded;

FIG. 23 shows a perspective view of an exemplary embodiment of a closure device having an aperture therein according to the subject invention;

FIG. 24 includes FIGS. 24A and 24B which show an exemplary embodiment of another subject closure device with FIG. 24A showing a perspective view of the closure device having an aperture therein in the shape of a cross or star according to the subject invention and FIG. 24B showing an enlarged, top view of the aperture of FIG. 24A;

FIG. 25 includes FIGS. 25A and 25B which show an exemplary embodiment of another subject closure device with FIG. 25A showing the closure device having an aperture therein in the shape of a slit according to the subject invention and, FIG. 25B showing an enlarged, top view of the aperture of FIG. 25A;

FIG. 26 includes FIGS. 26A and 26B which show an exemplary embodiment of another closure device of the subject invention with FIG. 26A showing a perspective view of the closure device having a slit therein in the shape of a cross or star according to the subject invention and FIG. 26B showing an enlarged, top view of the aperture of FIG. 26A;

FIG. 27 shows a perspective view of another exemplary embodiment of a subject closure device having a stoma;

FIG. 28 shows the device of FIG. 27 operatively positioned in a vessel;

FIG. 29 shows a perspective view of another exemplary embodiment of a subject closure device having a stoma with contoured walls;

FIG. 30 shows a perspective view of another exemplary embodiment of a subject closure device having a stoma with a transition portion;

FIG. 35 includes FIGS. 35A-35C each of which show a step of deploying a subject closure device into an opening in a vessel wall to be closed and closing the opening with the device;

FIG. 36 includes FIGS. 36A and 36B each of which shows an alternative side-to-side embodiment of the invention with FIG. 36A showing a perspective side view of the device and FIG. 36B showing a top perspective view of the device;

FIG. 37 includes FIGS. 37A and 37B both of which show an alternative end-to-side embodiment of the invention with FIG. 37A showing a perspective side view of the device and FIG. 37B showing a top perspective view of the device;

SUMMARY OF THE INVENTION

Figure 1:
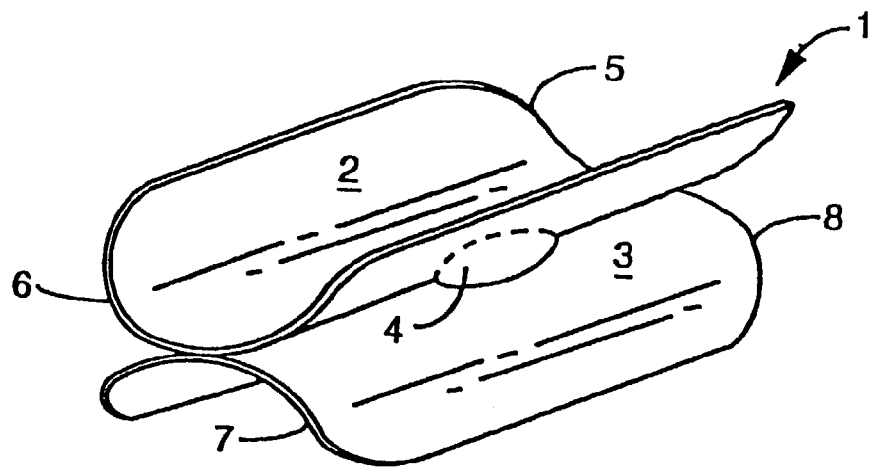
FIG. 1 is a perspective view of a simple side-to-side embodiment of the invention where two partial cylindrical segments are interconnected along the periphery of an opening.

The present invention provides implantable devices and associated methods for closing an opening in and/or interconnecting human vessels, lumens, ducts or other tubular organs or tissue rapidly, safely and in a minimally invasive manner. These devices and methods are particularly helpful in surgical procedures involving small vessels or the like within a limited surgical access field, such as coronary artery bypass graft procedures (CABG). A CABG procedure involves the establishment of an alternate blood supply path to bypass a diseased section of a coronary artery. With the present invention, an implantable device is positioned within a target vessel, such as downstream of a diseased coronary artery, which allows the attachment of a second, graft vessel to form the anastomosis. The procedure for attaching the vessels is called anastomosis.

The subject invention provides devices and methods for forming both side-to-side and end-to-side anastomosis. A side-to-side anastomosis procedure involves the attachment of two vessels at incised locations (e.g., arteriotomies) within a side wall of each of the vessels. An end-to-side anastomosis procedure involves the attachment of two vessels at an incised location within a side wall of one of the vessels and at the transected end of the other vessel.

Also provided are devices and methods of use thereof for closing and sealing an opening in tissue such as an opening in a vessel wall to provide a substantially fluid-tight seal at the opening. The closure devices and methods of the subject invention advantageously close an opening in tissue using passive forces, i.e., internal conduit pressure exerted on a subject device. Accordingly, the precision and accuracy of aligning the closure device with the opening and the effectiveness of the seal provided thereby are not dependent upon a secondary element such as a fixation element or the like.

Common to all of the devices of the present invention is the presence of at least one flexible member, herein also referred to as a first segment in the form of a sheet, membrane or flange. The flexible member is adapted to conform to and seal with an inner surface or circumference of a vessel into which it is delivered. Furthermore, the flexible member is adapted to utilize the internal vessel pressure exerted thereon to form a substantially fluid-tight seal with the inner surface of the conduit whereby substances within the vessel are prevented from leaking from the artificial opening under normal physiological conditions.

More particularly, the flexible member has first and second surfaces. The first surface, herein also referred to as the lumen-facing surface, is adapted to utilize the internal conduit pressure exerted thereon to form a substantially fluid-tight seal between the second surface and an inner surface of the conduit. The second surface, herein also referred to as the contact surface, is adapted to contact and form a substantially fluid-tight seal with an inner wall or circumference of the vessel. Thus, upon deployment of the flexible member into a vessel, the member conforms to the interior walls of the vessel to provide a sealing contact along the second surface and sufficient physical stability to the device to prevent displacement from the vessel. Moreover, the substantially fluid-tight seal is formed without compressing, tensioning or puncturing the vessel wall.

The side-to-side anastomotic devices of the subject invention include both a first segment and a second segment connected by a flow opening along the periphery of the two connected segments. The first and second segments are sufficiently flexible and compliant, as well as sufficiently stiff, for easy insertion into an incision made within each vessel. Upon release, each segment subsequently conforms to the interior walls of a conduit to provide a sealing contact along the contact surface of the segment. Once deployed within the conduits, the sealing contact and stiffness properties of the segments provide sufficient physical stability to the device to prevent displacement from the respective vessels. The flow opening provides a pathway through which fluid can be transported between anastomosed conduits. More specifically, the flow opening provides a location of permanent connection between the two segments of the anastomosis device and, thus, establishes fluid communication between the vessels connected by the implanted device.

The end-to-side anastomotic devices of the subject invention include a first segment as described above positioned at one end of a tubular member, where the tubular member and the first segment are connected by a flow opening analogous to that found in the side-to-side device of the present invention. The first segment of the end-to-side device has the same or similar properties and advantages as described above with respect to the segments of the side-to-side device. The tubular member may be normal to, or positioned at an angle relative to, the surface of the first segment.

The closing devices of the subject invention are typically made-of a single segment that has the same or similar properties and advantages as described above with respect to the subject anastomotic devices. That is, the segment that forms a subject closure device is sufficiently flexible and compliant, as well as sufficiently stiff, for easy insertion into the opening to be closed within each conduit wall. Upon release, the segment subsequently conforms to the interior walls of a conduit to provide a sealing contact along the contact surface of the segment. Once deployed within the conduit, the sealing contact and stiffness properties of the segment provides sufficient physical stability to the device to prevent displacement from the respective conduit, i.e., to prevent displacement from the opening of the conduit.

The segments of the subject devices are constrictable (such as by bending or folding) to a size sufficient to fit through the artificial opening and are expandable to be securely and permanently self-retained within the vessel upon implantation. The segments comprise relatively thin walls, thus minimally interfering with fluid flow within the interconnected vessels. The intravascular pressure against the underside of the segment secures the segment against the inside vessel wall thereby preventing leakage from the anastomosis site. Additionally, the configuration of the segments is such that it provides an element of passive force when deployed within the vessel so as to pull the two vessels together for better sealing and healing of the vessel walls. The selection of materials for making the implantable devices of the present invention is also important for the devices to achieve their intended purposes. In addition to being adequately biocompatible, the material(s) have appropriate mechanical properties for facilitating insertion, retention and sealing of the segments within the vessels. Additionally, the biocompatible devices may be made of any suitable bioresorbable and/or biodegradable materials, as well as autologous, allo- and xeno-graft biomaterials.

The implantable devices of the present invention are preferably in the form of a single-component unit but may be comprised of two (and possibly more) connectable components or pieces. The devices may be inserted or implanted using surgical tools or alternatively using a catheter designed specifically for the less invasive placement and release of the device within the vessels for interconnection thereof. The present invention may be provided in an assortment of sizes, shapes, configurations, etc. in order to close and seal openings within or interconnect vessels of various sizes, shapes and orientations. Also, the device(s) may be provided as a component of a kit along with other accessory components such as instruments for making an incision in a vessel for instrument access or for making an arteriotomy in a vessel to be anastomosed, for sizing or measuring the openings and/or vessels for determining the proper size of the device to be implanted, for sizing the intravascular segment, and for inserting the device into a vessel. These accessory instruments may perform one or more of the above functions either simultaneously or successively during the procedure. For example, an instrument capable of creating an arteriotomy may also be configured to successively insert an anastomosis device of the present invention into that arteriotomy. Preferably, the successive steps may be accomplished in a singular action or one fluid motion of the instrument.

The implantable devices may be used to close any type of opening in any type of tissue such as any bodily conduit, (e.g., a vessel), organ, etc., or join any two (or more) vessels together such that fluid communication is established between the lumens of the two joined vessels, where representative types of vessels include, but are not limited to, vascular vessels and other vessels of the body, where one of the vessels may be a synthetic vessel or graft vessel from a donor, e.g., autograft or allograft. While the specific embodiments described herein illustrate devices for joining only two vessels, those skilled in the art can appreciate that embodiments for joining three, or possibly four or more, vessels are possible under the present invention.

As mentioned above, the implantable device, and the associated implant methods, are particularly applicable for performing anastomosis surgery for grafting two juxtaposed cardiac vessels or for grafting a native vessel to one or more natural or synthetic graft vessels. The CABG surgery may be performed on either a stopped or a beating heart. In many embodiments of interest, the subject devices and methods are employed in distal anastomosis applications, although other anastomosis applications are also of interest, e.g., proximal, etc. Furthermore, as described above, the implantable device and associated implantation methods are applicable to close and seal openings in any vessel, lumen, duct or tubular organ.

An object of the invention is to provide a device for interconnecting two vessels within a patient—which device is configured so as to be easily inserted into an opening in a vessel and allow for a flow of material through the vessel after insertion.

Another object of the invention is to provide for a method of quickly and efficiently performing an anastomosis.

Another object of the present invention is to provide anastomotic devices and methods which avoid puncturing of a vessel and which avoid or minimize tension and compression forces at the site of the anastomosis.

Another object of the present invention is to provide an anastomotic device whose primary means of sealing to the vessel is by the device's ability to conform to the inside vessel wall and then by the intravascular pressures against the device caused by flow within the vessel.

Yet another object of the present invention is to provide anastomotic devices and methods which minimize the risk of creating emboli while performing an anastomosis procedure.

Another object of the invention is to provide a device for closing and sealing an opening in tissue such as in a bodily conduit, e.g., a vessel or in an organ, e.g., septal wall, etc., which device is configured so as to be easily inserted into the opening and to provide for a substantially fluid-tight seal at that opening while allowing for a flow of material through the conduit, for example, after insertion and implantation.

Another object of the invention is to provide for a method of quickly and efficiently closing and sealing an opening in tissue that is not dependent on placing and securing a secondary element or device such as a fixation element or the like.

Another object of the present invention is to provide devices and methods for closing and sealing an opening in tissue which avoid puncturing of the tissue and which avoid or minimize tension and compression forces at the site of the closure.

Another object of the present invention is to provide a tissue closing and sealing device whose primary means of closing and sealing an opening in tissue is by the device's ability to conform to tissue and then by the physiological pressures against the device caused by flow in or around the tissue, e.g., a subject device's primary means of closing and sealing an opening in conduit such as a vessel is by the device's ability to conform to the inside conduit wall and then by the intraluminal pressures against the device caused by flow within the conduit.

Yet another object of the present invention is to provide tissue closing and sealing devices and methods which minimize the risk of creating emboli or creating other trauma and adverse consequences to the tissue.

Yet another object of the present invention is to provide tissue closing and sealing devices and methods that promote natural, biological closing and sealing of an opening, for example by promoting thrombogenesis at the opening.

Another object of the present invention is to provide a device for patching and sealing irregularities present on a surface of tissue, e.g., on the surface of a conduit such as a vessel wall.

An advantage of the invention is that the methods can be readily performed because the device is small, flexible and easily manipulated.

A feature of the devices of the invention is that they can be comprised of a variety of materials.

Another feature of the invention is that the devices are flexible and readily conform to the inside wall of the native vessels to minimize irritation to the endothelial cells of the vessel wall.

Another feature of the devices is that the surface contact area of the devices with the vessel wall is minimized to reduce unwanted biological responses to the implant.

Another feature of the invention is that one device can be used to accommodate a wide range of different size vessels.

Another feature of the invention is that the same device can be used to close and seal a wide range of different size openings.

Another feature of the invention is that the same device can be used to patch and seal a wide range of tissue surface irregularities.

Another feature of the invention is that the surface of the device can be modified for example to provide a porous device and/or may be coated and/or embedded with one or more agents or components such as endothelial cells, growth factors, stimulants, thrombogenic material, etc.

Another feature of the invention is that the device can be sold in a kit containing a range of different sizes of devices that could be useful for insertion into a wider range of vessel sizes and/or for closing a wider range of openings.

Another feature of the invention is that the device can be sold in a kit containing the means to size the intravascular segment for insertion into a range of vessel sizes.

Another feature of the invention is that the device can be sold in a kit containing the means to size an opening to be closed.

Another feature of the invention is that the intraluminal pressure provides a sealing force on the implanted device to prevent leakage at the anastomosis site.

Another feature of the invention is that the intraluminal pressure or other analogous physiological pressure provides a sealing force on the implanted device to prevent leakage at the seal.

An aspect of the invention is a side-to-side anastomotic device comprised of a first segment connected to a second segment along the periphery of an interconnecting opening.

Another aspect of the invention is an end-to-side anastomotic device comprised of a first segment connected to a tubular member along the periphery of an interconnecting opening.

Another aspect of the invention is a tissue closing and sealing device made at least in part of a flexible member.

Another aspect of the invention is a tissue closing and sealing device that promotes a natural, permanent closure and seal at an opening in the tissue such as at an opening in a vessel wall.

Another aspect of the invention is a patching and sealing device that patches and seals over a tissue surface irregularity and provides a smooth tissue surface.

Another aspect of the invention is that the device can be loaded into a catheter delivery system.

Another aspect of the invention is that the device can be loaded into a surgical delivery dispenser.

Another aspect of the invention is that it facilitates the application of adhesive.

Another aspect of the invention is that it can be inserted using robotic assist devices (U.S. Pat. No. 5,855,583).

Another aspect of the invention is that it can be used with a variety of tissues, conduits, vascular grafts, artificial or prosthetic. Examples of vascular grafts are coronary artery to the coronary vein, radial artery to the coronary artery, saphenous vein to the coronary artery, gastroepoploic artery to the coronary arteries, femoro-popletial bypass using vein or other conduit, etc.

Yet another aspect of the invention is that the anastomosis procedure can be carried out using a loading device or an endovascular catheter in order to insert a device of the invention.

These and other objects, aspects, advantages and features of the invention will become apparent to those skilled in the art upon reading this disclosure in combination with the accompanying figures.

DETAILED DESCRIPTION OF THE SPECIFIC EMBODIMENTS

As summarized above, the subject invention provides implantable tissue closure devices and anastomotic devices and methods for using the same. The subject devices are characterized by having at least one segment, a "first segment," that, upon deployment in a vessel, conforms to the inner surface of the vessel wall in a manner such that a sealing relationship is produced between the implanted device and the vessel wall. This sealing relationship is passive in that no other mechanical (e.g., staples, sutures, etc.) or adhesive (e.g., a biological glue) means is used or is necessary to be used for maintaining the sealed engagement of this first segment. Instead, the sealing engagement is caused primarily by the ability of the device to conform within and to the vessel wall and to be retained in that sealing relationship by means of the pressure within the vessel.

Both side-to-side and end-to-side anastomotic devices, as well as tissue closure devices, as described above are provided by the subject invention. Also provided are kits for use in performing tissue closing procedures and anastomotic procedures, including both side-to-side and end-to-side anastomotic procedures. In further describing the subject invention, the devices themselves are first described in greater detail, followed by a review of various representative anastomotic and tissue closure protocols in which the devices may be employed and a further elaboration on the kits of the subject invention.

Before the present invention, devices and methods used therein are disclosed and described, it is to be understood that this invention is not limited to the particular components, devices or steps illustrated and discussed, as such may, of course, vary. For example, the anastomosis devices of the invention and use of these devices is primarily described in the context of CABG procedures; however, the invention is useful for many other medical procedures for the connection of other natural and synthetic lumens and organs. Some of these other procedures include general vascular reconstruction and cerebral spinal fluid shunting for the treatment of hydrocephalus. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

Anastomotic Devices and Tissue Closure Devices

As summarized above, the subject tissue closure devices and the subject anastomotic devices, for both side-to-side and end-to-side applications, are all characterized as having at least one segment (a "first segment") that, upon deployment in a conduit such as a vessel, conforms to the interior walls of the vessel to provide a sealing contact along the contact surface of the segment inserted within the vessel. By "sealing contact" it is meant that the area of contact produces a barrier that is substantially impervious to fluid flow, such that fluid does not flow across the border defined by the area of the contact.

In certain embodiments, at least a portion of the segment is comprised of a flexible, compliant material to enhance conformity of the segment to the vessel wall. The compliant material may take the form of a membrane or flange, or a plurality of membranes or flange elements which can be easily constricted for ease of insertion but which have a natural tendency to return to an unconstricted (i.e., an unfolded or unbent) configuration to readily seal to and conform with the inside vessel wall. In some embodiments, this tendency provides a spring-like force that assists in securing the membranes or flanges to the vessel wall. When operatively placed, the membrane(s) or flange(s) are caused to press against at least a portion of the inside wall of the target vessel primarily by the pressure within the target vessel, for example, by the intravascular blood pressure in the context of a CABG procedure. Thus, the contact and conformation of the segment or a flange portion thereof to the vessel wall is accomplished passively, preferably without the additional use of adhesive (e.g., biologic glue) means or means which penetrate and compress the vessel wall (e.g. staples or sutures).

The configuration and dimensions of the flexible segments of the subject devices are important for the devices to accomplish their intended purposes. More specifically, each segment has a thickness(es), surface area, length and width (or diameter) dimensions for optimizing insertability of the segment into the vessel, maximizing the sealability of the segment to the vessel wall, minimally interfering with fluid flow within the interconnected vessels and maximizing the tensile strength of the device to retain itself (i.e., "self-retaining") within the vessel under a range of likely physiological conditions without the need for an ancillary fixation or retention device or component.

The segments comprise relatively thin-walls, thus minimally interfering with fluid flow within the interconnected vessels. A segment may have one continuous thickness or may have varying thicknesses throughout its structure. In either case, the segments have optimal thicknesses such that segments are sufficiently compliant and flexible so as to be compressible for insertion into a vessel, while being sufficiently rigid to facilitate insertion without the segment folding on itself or becoming kinked or otherwise mechanically damaged upon entry into the vessel.

The thickness as well as the surface area of a segment are also optimized for providing sufficient physical stability so that the segment remains securely positioned within the vessel particularly when subject to internal forces (e.g., an increase in a patient's blood pressure either during or after surgery) and/or external forces (e.g., the tugging and pulling that are likely to result from manipulation of the device during the anastomosis procedure or by the normal beating of the patient's heart after the procedure).

Still further, the thickness and surface area of the segments are such that, when operatively used, cause the segment(s) to provide an element of passive force that can pull, for example in the context of an anastomosis procedure, the two anastomized vessels together. More specifically, the pressure against the wall created by the intravascular fluid flow or blood pressure, which is typically in the range from about 60 to 180 mm of Hg under normal conditions, secures each segment in a sealing engagement against the inside vessel wall. This sealing engagement holds the individual segments in a stable and permanent position within the vessel. The sealing engagement also prevents the leakage of fluid from the opening or incision or arteriotomy within the vessel wall during the implantation of the device, as well as from the resulting anastomotic site after completion of the anastomosis procedure or from the resulting seal in the context of closing and sealing an opening in a vessel. The stable and leak-free positioning of the anastomotic device enables the vessels, and more particularly their respective incised edges, to be accurately appositioned with respect to each other, thereby facilitating the natural tissue bonding between the two, preferably without the use or with minimal use of other mechanical or adhesive means.

Figure 9:
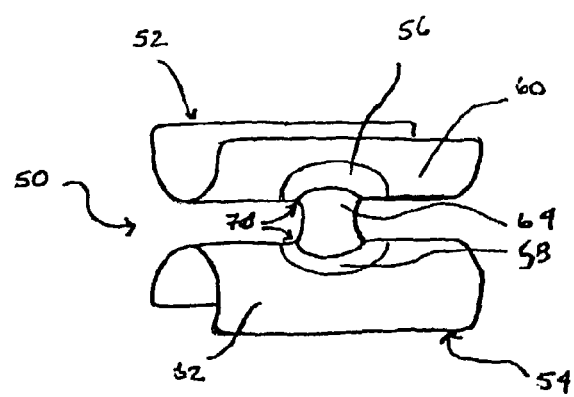
FIG. 9 illustrates another side-to-side embodiment of the invention having a flow channel extending between the two segments.

As described below in greater detail, the segments of the present invention may have a variety of different configurations, thickness(es), surface areas, lengths and widths (or diameters). For example, useful configurations include, but are not limited to, partial cylinders (see FIGS. 1, 2, 5, 7A-E, 9 and 10 for anastomotic devices and FIGS. 16 and 18 for closure devices) and full cylinders (see FIG. 3 for an anastomotic device and FIG. 19 for a closure device), or generally planar configurations having circular (see FIGS. 6A-C and 11A-B for anastomotic devices and FIG. 21 for a closure device), elliptical (see FIGS. 12A and 15A-C for anastomotic devices and FIG. 20 for a closure device), starred, petaled or rectangular shapes, or combinations of these configurations (e.g., see FIG. 9 showing an anastomotic device and FIG. 22 showing a closure device having a segment having a generally planar rectangular shape which is conformable into a partial cylinder). Generally, the size and shape of the segments of the present invention are dependent on the size (i.e., the circumference or diameter) and shape of the bodily lumen or tissue structure into which it is to be used and the size (i.e., the circumference or diameter) and shape of the opening to be closed and sealed. For example, in the context of anastomotic devices and procedures, larger segments may be preferable when performing a proximal anastomosis to an aorta, or when anastomosing peripheral (e.g., in the leg) or abdominal vessels while smaller segments are more appropriate for coronary arteries and veins. Also, the length or width (or diameter) dimensions or both, may be dictated by the length of the incision or arteriotomy within the lumen or vessel into which the segment is to be placed.

In side-to-side embodiments of the anastomotic device, the flow opening between the segments which establishes fluid communication between the two may also have varying shapes and sizes according to the size of the arteriotomy and the application in which it is being used. The length of the flow opening (i.e., the distance between the two segments), may also vary depending on the distance between the vessels' respective attachment points. In some embodiments, where the outer surfaces of the segments are close enough to touch each other, the flow opening for each of the segments is necessarily one and the same (see FIGS. 1, 3, 4A-C, 5, 6A-C and 7A-E). Other embodiments have flow openings that define a tubular pathway or channel between the segments (see FIGS. 9, 10, 11A-B and 36A and 36B). The flow opening between segments is configured to minimize disturbances to the fluid flow such as turbulence or no-flow regions.

Both side-to-side and end-to-side anastomotic devices are provided by the subject invention and are now separately described in greater detail below, followed by a description of the subject closure devices.

Side-to-Side Anastomotic Devices

The side-to-side anastomotic devices of the subject invention include a first segment and a second segment connected by a flow opening along the periphery of the two connected segments or by a flow channel extending between the respective flow openings. The first and second segments are flexible and compliant for easy insertion into an incision made within each vessel. Upon release, each segment subsequently conforms to the interior walls of a vessel to provide a sealing contact along the contact surface of the segment inserted within the vessel. Preferably, the features mentioned above with respect to the first segment also apply to the second segment of the side-to-side embodiments of the present invention. The flow opening/channel provides a permanent connection between the two segments and fluid communication between the vessels connected by the implanted device.

FIG. 1 shows the flexible device 1 that is comprised of a first segment 2 and a second segment 3. In this embodiment the first segment 2 and the second segment 3 are mirror images of each other and are interconnected (preferably in a permanent manner) to each other along the periphery of an interconnecting opening 4. The first segment 2 has an end 5 and an opposite end 6. The ends 5 and 6 are equal distance from the center of the opening 4. Although the ends shown here have smooth, rounded edges the ends may be shaped in any desired form noting that it is preferable to have end edges which can be easily inserted into a vessel and not cause damage to the vessel. The second segment 3 has an end 7 and an opposite end 8 each of which are also equal distance from the center of the opening 4. In their unconstricted, unfolded or unbent states, segments 2 and 3 each have a generally planar configuration but may, however, have other than planar configurations (e.g., cylindrical) in an unconstricted state.

Figure 2:
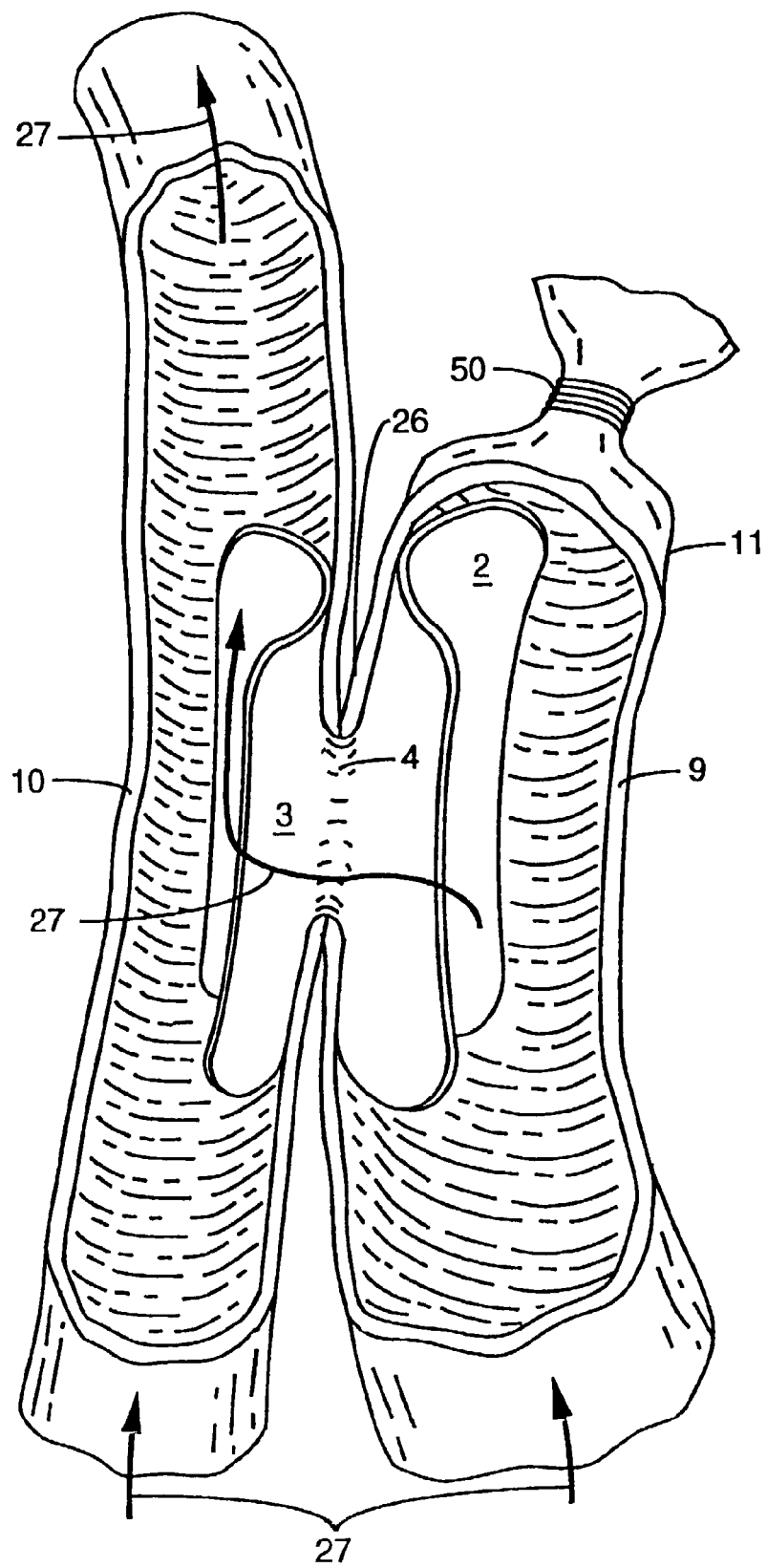
FIG. 2 shows the embodiment of FIG. 1 inserted within two vessels thereby interconnecting those vessels.

The device 1 as shown in FIG. 1 is shown inserted into vessels 9 and 10 in FIG. 2. Depending on the particular configuration of the device 1 the insertion can be carried out in a number of different ways. As an example, the first segment 2 can be constricted, either manually or by the aid of an insertion tool, so that it forms a tighter semi-circle and/or the ends 5 and 6 can be folded towards each other. In this position the ends 5 and 6 can be made to touch each other and can be inserted within the opening of a first vessel 9. Thereafter the second segment 3 can be inserted within an opening of a second vessel 10 in the same manner. Once properly seated within the vessel, each segment is released from its constricted state and allowed to deploy whereby the respective ends unfold or expand and move against and conform to the inside vessel wall thereby establishing a fluid pathway between the vessels via the center of opening 4. Thus, a side-to-side interconnection of vessels 9 and 10 is completed. In many situations it is desirable to close off one end of one of the vessels. As shown in FIG. 2, the end 11 of the vessel 9 has been tied off.

In the embodiment of the device 1 as shown in FIG. 1 the first segment 2 and second segment 3 are mirror images. However, the two segments can be different in size (circumference, width or length) and shape from each other. Different sizes are useful in situations where it is desirable to interconnect two vessels which are different in size. The embodiment of FIG. 1 also shows that the ends 5 and 6 of the first segment 2 as well as the ends 7 and 8 of the second segment 3 are equal distance along their entire edge from the center of the opening 4. However, the ends 5, 6, 7 and 8 can be configured in any given manner and distance from interconnection hole 4 as well as being tapered or rounded on each or either end.

FIG. 2 illustrates an exemplary anastomosis surgery consisting of grafting two juxtaposed vessels 9 and 10. After creating an artificial opening (e.g., an arteriotomy) in each vessel, the surgeon inserts one segment 2 in one vessel 9 and the other segment 3 into the other vessel 10 whereby the pressure created by device 1 due to expansion of its segments and the action of intraluminal pressure prevents leakage of fluid from the graft site 26. The fluid then passes along flow path 27 from vessel 9 through the hollow connecting hole 4 into the vessel 10. The surgeon may tie off the distal end of the graft vessel using a thread 50, staple or other suitable closure or binding means. When the segments 2, 3 expand back to their original size and shape, they will conform to the vessel walls to provide a sealing pressure and a firm fit.

After insertion and completion of the anastomosis using the device 1 shown in FIG. 1 and inserted within the vessels of FIG. 2, it is necessary that the free end of the vessel be tied off by any standard closure or binding means using sutures, metal clips or other securing mechanisms such as the thread 50 shown in FIG. 2. For example, the saphenous vein, right or left internal mammary artery, or radial artery used to form the anastomosis is terminated or closed off at the end as shown with the thread 50. Other closure means are taught in U.S. Pat. No. 5,234,448. Closing off of the vessel 9 would clearly not be necessary during any side-to-side anastomosis where the vessel is to be anastomosed to another vessel at a more distant point. During the procedure, the placement of one to three stay sutures in order to stabilize the graft to the heart or to juxtaposition the two vessels together may be desired. Such sutures are easily placed through the fat or tissue surrounding the vessels in order to provide additional stability to the anastomosis. This is normally performed when grafting an internal mammary artery to the coronaries but may be required during implantation of the inventive device in order to prevent the anastomosed vessels from being inadvertently separated from each other during or after the procedure. However, far fewer, if any at all, suture points would be required or used in the context of the methods of the present invention than would otherwise be used in the case where an entire anastomosis is formed by suturing alone.

Although the device 1 shows a first segment 2 and second segment 3 each of which has a partial cylindrical shape and each of which is identical in size and shape to the other, a variety of different configurations are contemplated by the present invention. Some of these configurations are shown in the other embodiments—see FIGS. 3, 4, 5, 6, 9, 10, 11, 12 and 36A and 36B. However, those skilled in the art will contemplate numerous additional embodiments upon reading this disclosure. As one example it is pointed out that the first segment 2 and second segment 3 can be generally flat or planar, i.e., have outer surfaces which are contained within a single plane. If each segment is flat or generally planar, then the segment is folded before being placed in the opening of a vessel. Once in place each segment will assume the configuration of the interior wall of the vessel it is placed within. Further, each segment will apply some pressure against the interior wall of the vessel thereby holding the device in place. With each of the embodiments of the invention, the segments may be designed to be flexible and in a slightly bent or constricted shape when present within the interior wall of the vessel so that the outer surface of each segment is forcing itself against the interior wall of the vessel while the device is attempting to reassume its original configuration. This aspect of the devices augments the force created by blood pressure or other fluid pressure within the vessels that holds the device in place.

In the device 1 shown in FIG. 1 and used within FIG. 2, the first segment 2 and second segment 3 are connected along the periphery of the opening 4. Accordingly, the first segment 2 and second segment 3 touch each other along a line extending outwardly along the periphery of the opening 4 to the respective ends of each segment. However, in alternative embodiments, the opening 4 can be in the form of an open channel that could be cylindrical in shape (see FIG. 9, for example). The open channel would connect to the opening 4 on each segment of the device. The channel would separate the first segment 2 from the second segment 3 by the length of the channel and it would be used in situations where the vessels being connected are not positionable against each other. For example, one of the vessels may be embedded within a layer of muscle or other tissue.

Figure 3:
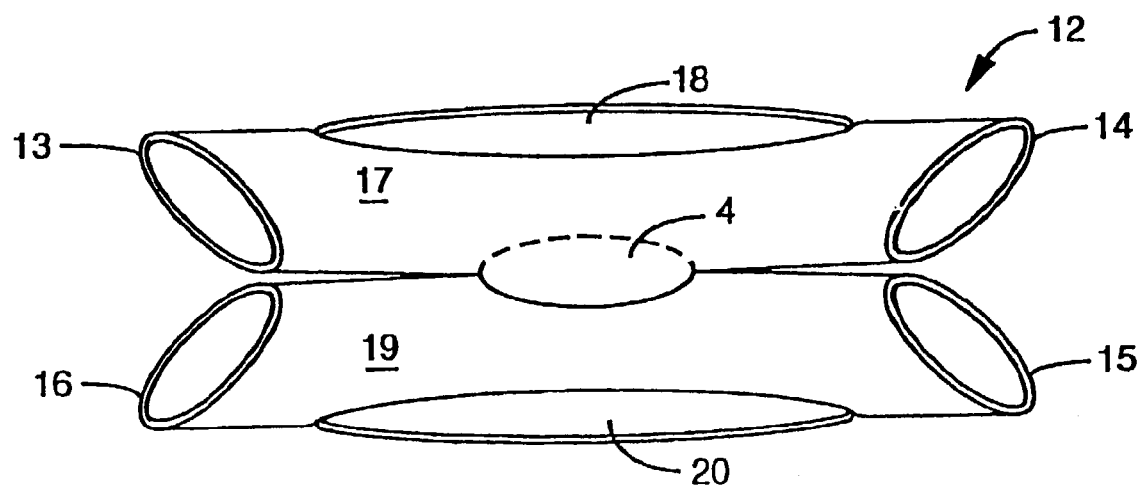
FIG. 3 shows an alternative side-to-side embodiment of the device of the invention where full (complete) cylindrical segments having tapered ends are interconnected along the periphery of an opening wherein each of the segments has an opening in its upper surface.

FIG. 3 shows an alternative embodiment 12 of the invented device having tubular segments 17 and 19. Tubular segment 17 comprises tapered ends 13 and 14 and tubular segment 19 comprises tapered ends 15 and 16. The tapering of these ends may have a low friction coating and be very smooth thereby providing a number of advantages which include making it easier to insert into a vessel. The configuration of FIG. 1 shows that the first segment and second segment are each configured in the form of a portion of a cylinder in an unconstricted state. However, the device could be configured so that each segment is a complete cylinder (see FIG. 3) in an unconstricted or constricted state. An advantage of having each of the segments a partial cylinder is the ability to conform to a wider range of different vessel diameters to improve the fitting range. Another advantage is the maximizing of the amount of endothelial wall of the vessel not covered by the device 12 to minimize any negative biological response to the implantable device 12. In the configuration shown in FIG. 3 a complete cylinder is provided for each segment. However, the first segment 17 has an opening 18 in its upper surface and the second segment 19 has an opening 20 in its upper surface.

Another embodiment of the invention is shown in FIGS. 4A, 4B and 4C each of which shows a folding/expandable device 21. In FIG. 4A the segment 22 is in its expanded configuration and the segment 23 is in a completely folded configuration. FIG. 4A shows the segment 23 being inserted into an opening 24 in a vessel 25. Once the segment 23 has been inserted, it is released and it begins expanding to a partially folded configuration as shown in FIG. 4B. FIG. 4C shows the segment 23 completely expanded. After this procedure is completed the same procedure could be carried out with the segment 22 on a separate vessel (not shown).

In device 1 of FIG. 1, the first segment 2 and the second segment 3 are connected in a manner such that they are parallel to each other. However, as shown in FIG. 5 the first segment 30 may be positioned at a right angle to the second segment 31. As with the embodiment as shown in FIG. 1 the device 33 shown in FIG. 5 has the segments 30 and 31 interconnected along the periphery of an opening 4. Those skilled in the art will recognize that the segments of the device can be interconnected at other places. However, interconnection in some manner along or near the periphery of the opening is important in order to provide a seal between the first and second segments. The device 33 shown in FIG. 5 is also different from the device 1 shown in FIG. 1 in that the first segment 30 is larger in diameter than the second segment 31. This differentiation in the diameter of the two segments is preferable in situations where the surgeon is interconnecting two vessels which are different in diameter.

In the embodiment as shown in FIG. 5 the first segment 30 and second segment 31 are positioned at a 90° angle with respect to each other. However, the first and second segments can be positioned at any angle relative to each other, i.e., any angle between being directly parallel as shown in FIG. 1 to being at a right angle or 90° angle as shown in FIG. 5. Thus, the embodiment of FIG. 1 shows the first segment 2 and second segment 3 positioned at a 0° angle. In this position it is sometimes difficult to provide the necessary access in terms of a required line of sight or manual manipulations. Accordingly, offsetting one segment relative to the other at some angle (between 0° to 90° or more preferably between 20° to 90°) may improve visual and manual access. In the embodiment of FIG. 5 the first segment 30 and second segment 31 are directly connected to each other along the periphery of the flow opening 4. However, as explained above, the first and second segments may be interconnected by a channel. The channel could be of any length but is preferably 2 cm or less in length and has a diameter which is substantially equal to the diameter of the interior wall of one or both of the vessels being connected, and, as such, is designed to minimize flow disturbances.

The device 33 shown in FIG. 5 is also different from the prior configuration shown in FIG. 1 in another important feature. Specifically, the larger first tubular segment 30 nearly forms a complete cylinder. The edges 34 and 35 are close to each other compared to those of the device shown in the configuration of FIG. 1, which forms half or less than half of a cylinder. The second tubular segment 31 (FIG. 5) is shown in a state where it initially forms a complete cylinder along a separation string or thread 37 (shown along the dashed line 36). When thread 37 is pulled the edges of the second tubular segment 31 separate causing the tubular segment to form a partial cylinder as is shown with the first tubular segment 30. Thus, the second tubular segment 31 is shown in its original state wherein the first tubular segment 30 is shown in a state after the separation thread 37 has been pulled apart. Once the separation thread 37 has been pulled apart and the edges are separated from each other, the cylinder expands radially outwardly to conform to the interior walls of the vessel. Thus, the device is first inserted into the vessels and then the separation thread 37 in each tubular segment is pulled apart allowing the edges to separate and the partial cylinder to expand and apply force against the interior walls of the vessel. In this manner the device is securely held in place and the fluid flow within the vessel is not obstructed by the device.

In describing the device of the present invention the terminology "conforms" or "conforms to" and the like is used to refer to the outer surface area of each segment of the device. What is intended by this terminology is that the device is designed to sufficiently conform and seal the interior walls of the vessel when it is placed within. As indicated above each segment of the device may be planar in configuration and bent into a curved cylindrical portion during insertion into a vessel. Once the segment is inserted and released, the segment attempts to resume its original configuration, with the additional action of intraluminal pressure, it conforms substantially to the interior walls of the vessel.

The embodiment shown in FIG. 5 shows the application of a thread 37 for separating the edges of a tubular segment and conforming to the interior walls of the vessel. Other means for edge separation and constriction are possible for use with the present invention. For example, both segments or portions of the device shown in FIG. 5 could be separated providing edges such as the edges 34 and 35 shown in the first segment 30. A thread could be tied around the first segment 30 forcing the edges 34 and 35 together or even forcing them to overlap each other. Thereafter the segment 30 is placed within the vessel and the thread is removed. After the thread is removed the segment 30 attempts to resume its original configuration and the outer surfaces of the segment 30 force themselves against the inner surfaces of the vessel and thereby conform to the interior wall of the vessel. Other means of constricting the diameter of each segment or portion prior to insertion and thereafter allowing that segment or portion to relax and attempt to reassume its original configuration are contemplated by the present invention.

FIG. 9 illustrates yet another embodiment of a side-to-side device 50 of the subject invention. Device 50 has a first segment 52 and a second segment 54, each having a rectangular contact surface which, when in constricted conditions, has a semi-cylindrical configuration. Segments 52, 54 each comprise a reinforcement portion 56 and 58, respectively, and a membrane or flange portion 60 and 62, respectively. Within the boundaries of the reinforcement portions 56, 58 are flow openings in between which extends a flow channel 64 providing fluid communication between the vessels into which the segments 52, 54 are inserted. Reinforcement portions 56 and 58 are integral with flange portions 60 and 62, respectively, and act to further reinforce the sealing force of the flanges against the vessel walls. Here, reinforcement portions 56, 58 have a circular configuration comprising a surface area which extends radially outward from their respective flow openings. However, reinforcement portions 56, 58 may have any other appropriate configuration including, but not limited to, a ridge, radially extending petals, an ellipse or a rectangle. The respective flange portions 60, 62 are made of the same or similar materials as the segments of the embodiments described. Furthermore, flange portions 60, 62 may have the same or similar biocompatibility, sealing, insertion, compliance and tensile properties as the segments of the embodiments described above. Reinforcement portions 56, 58 preferably incorporate a polymer material such as nylon, polypropylene, and polyethylene, or a metal such as stainless steel or nitinol. To provide a ridge configuration, the material may be in the form of a monofilament. The reinforcement acts to better support and stabilize the segments 52, 54, respectively, within the vessels into which they are implanted, and thus, optimizing the overall stability of the device, once the anastomosis has been completed.

Although FIG. 9 illustrates base portions 56, 58 as having annular configurations that encircle the circumference of the respective flow openings, the reinforcement portions may have any appropriate configuration. For example, the reinforcement portion may also comprise a spine (not shown) that extends radially, in proximal and distal directions, from the flow opening along a line that bisects and is parallel to the longitudinal axis of the segment. Such a configuration facilitates the folding or constricting of the flange portions and provides additional stiffness to the segment as it is being inserted into a vessel.

Another aspect of the devices of the present invention that is important to consider is the radius of curvature of the juncture between a segment and the flow channel of a device of the present invention. This juncture runs the circumference of the contact area between the segment and the flow channel. The radius of curvature of the junction is selected to minimize turbulence of the fluid flow from the host vessel into the flow channel and from the flow channel into the graft vessel. Additionally, the radius of curvature may be selected to optimize the appositioning of the two vessels. In side-to-side embodiments having a flow channel extending between the segments, there are two such junctures, one between each of the segments and the flow channel. In FIG. 9, these junctures are identified by reference number 70.

Figure 10:
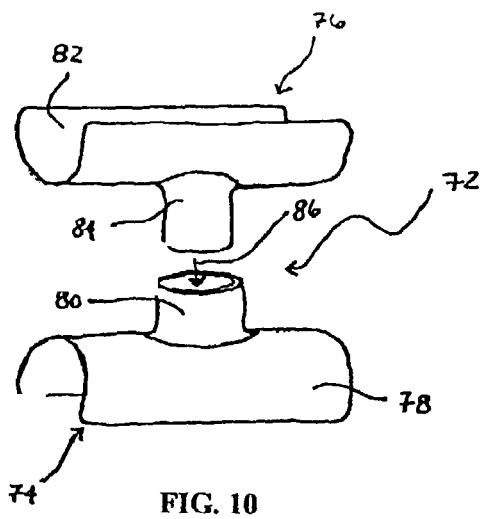
FIG. 10 illustrates another side-to-side embodiment of the invention having a two-piece configuration which pieces are connectable with each other for forming a fluid-tight flow channel between the two segments.

While only single-piece anastomosis devices have been discussed thus far, the present invention also provides for multiple piece devices. For example, FIG. 10 illustrates a side-to-side embodiment of a two-piece device 72 comprising a first piece 74 and a second piece 76. First piece 74 includes a first segment 78 and a first tubular flow channel portion 80 extending substantially perpendicular from the center of first segment 78. Second piece 76 includes a second segment 82 and a second tubular flow channel portion 84 extending substantially perpendicular from the center of second segment 82. First channel portion 80 has an inside diameter substantially the same as the outer diameter of second channel portion 84 such that a fluid-tight flow channel is created when second channel portion 84 is inserted, in the direction of arrow 86, within the lumen of first channel portion 80.

Figure 11A:
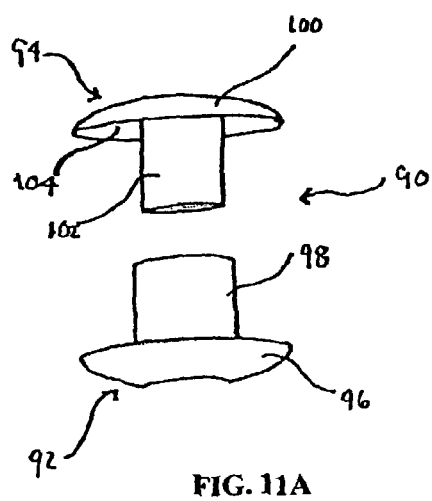
FIG. 11 includes FIGS. 11A and 11B which illustrate yet another side-to-side embodiment of the invention having segments with a rivet-type configuration.
FIG. 11B shows the device having one of its segments operatively positioned within a vessel.
Figure 11B:
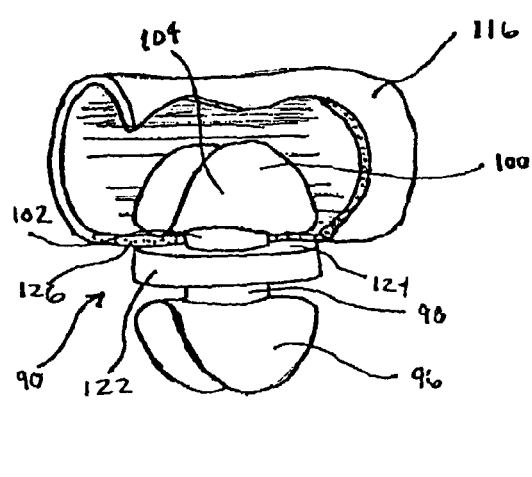

Another two-piece anastomotic device 90 of the present invention is shown in FIGS. 11A and 11B. Device 90 includes a first piece 92 and a second piece 94 each of which has a rivet-like configuration. First piece 92 includes a first segment 96 and a first tubular flow channel portion 98 extending substantially perpendicular from the center of first segment 96. Second piece 94 includes a second segment 100 and a second tubular flow channel portion 102 having the same relative relationship as the corresponding counterparts of first piece 92. First and second channel portions 98 and 102 also have the same relative relationship as their counterparts in FIG. 10 to form a complete flow channel. Here, however, the diameter of the resulting flow channel is greater than that of FIG. 10 and, thus, is more appropriate for use with larger vessels. Also different, is the annular, rivet-like shape of segments 96 and 100 which, when in their natural, unconstricted state (as in FIG. 11A), first and second segments 92, 94 have a cup-like configuration having opposing concave and convex sides. Concave side 104 of second segment 94, for example, faces the flow channel and opposing first segment 92. However, when operatively placed in a vessel, as shown in FIG. 1B, segments 96, 100 are forced to evert by an inherent spring-force inherent in the design of the device, with the originally concave sides 104 having a contact area flush with the inside of the vessel walls 116, creating a sealing pressure against the vessel walls. The sealing pressure caused by the spring-like action of the implanted segment 100 may be further augmented by a coupling mechanism 122, as shown in FIG. 1B. Here, the two pieces 92 and 94 of device 90 are operatively coupled to each other wherein first flow channel portion 98 of first piece 92 and a second flow channel portion 102 of second piece 94 are in a fluid-tight engagement in the same or similar manner as the device of FIG. 10.

As discussed previously, the primary and secondary means of sealing the segments or flanges of the present invention to the vessel wall are, respectively, the intravascular pressures against the segments or flanges and the physical properties of the segments or flanges themselves (including the reinforcement portion if used, such as reinforcement portions 56 and 58 of FIG. 9). The invention also provides a third and optional means of sealing in the form of a securement member or members which is/are generally positioned proximate the flow channel and/or the junction between the flow channel and which may be internal or external to the device. In FIG. 1B, for example, the securement means is in the form of a single collar, cuff or ring 122. Collar 122 is positioned around the outside of the flow channel and has a thickness such that its end surfaces 124 are in sealing engagement with the outside walls of the interconnected vessels (only one vessel 116 is shown). As such, the vessel wall 126 is atraumatically held between segment 94 and collar 122 with collar 122 acting as an external, static counter force to the internal forces of the segment's natural spring action and of the intravascular pressures. Preferably, at least the end surfaces of collar 122 are made of or coated with a material that stimulates hemostasis and wound healing.

Figure 34A:
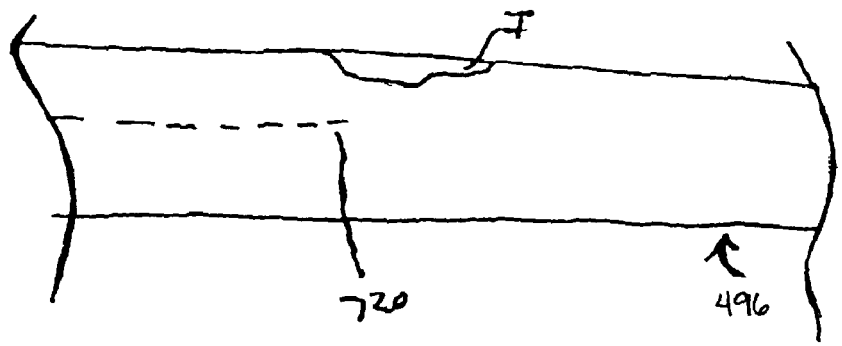
FIG. 34 includes FIGS. 34A-34D each of which show a step of delivering and deploying a subject device using an over-the-wire approach for patching and sealing an irregularity on a surface of a conduit wall.

FIG. 36A illustrates a perspective side view of another side-to-side anastomotic connector 500 having a first segment or flange 522 having a petaled configuration and a second segment or flange 523 having a petaled configuration. In this particular embodiment, four petals are shown on each flange, but it is to be understood that any number of petals may be employed, where the number of petals present for each flange may vary. Flanges 522 and 523 are connected by a flow channel 524 which extends between the two flanges to provide fluid communication between the vessels into which flanges 522 and 523 are inserted. The first and second flanges may be of the same shape, configuration and/or have the same dimensions, or may have different shapes, configurations and/or dimensions. For example, while device 500 is shown with both flanges having petaled shapes, it will be apparent that one of the flanges may have a shape or configuration other than petaled such as a shape of any of the embodiments described herein, e.g., circular, elliptical, rectangular, etc., and/or other configurations such as full cylinder, etc. Flow channel 524, as well as the flow channel of any embodiment of the subject invention, may be positioned at an angle relative to the flanges, i.e., the juncture of the channel and a flange may define an angle that is more or less than 90° or non-normal with respect to the flange. For example, angle $\gamma$ shown in FIG. 36A may define an angle that may range from about 1° to about 90°, usually from about 5° to 90°, and more usually range from about 20° to 90, as shown in FIG. 34A, or may be normal, i.e., positioned at approximately a 90° angle, with respect to a flange.

Side-to-side or end-to-end distances of flanges 522 and 523 designated by arrows 26 and 28, shown in the top perspective view of anastomotic connector device 500 in FIG. 36B, may be the same or differ from each other. In certain embodiments, the flanges may have a major axis, such as defined by arrows 526, and a minor axis, such as defined by arrows 528. The distance across the major axis may range from about 8 mm to about 30 mm, and more typically range from about 13 mm to about 15 mm. The distance across the minor axis may range from about 5 mm to about 15 mm, and more typically range from about 7 mm to about 9 mm. The flanges are bendable or foldable about either axis, and thus, device 500 may be delivered in a folded or bent configuration such as by folding or bending about one or both axes, as required by the surgical application.

While a number of different configurations are possible, as demonstrated above by the review of various representative configurations, the thickness and the area of contact between the deployed first and second segments and their representative vessels should be sufficient to provide for a sealing contact of sufficient strength to achieve the purpose of the devices. The segments have a surface contact area at least marginally greater than the surface area of the opening in the vessel through with the segment is inserted. For example, for devices suitable for use in CABG anastomosis procedures, the contact surface of the first and second segments has a surface area that is generally in the range from at least about 40 $mm^2$, usually at least about 70 $mm^2$ and more usually at least about 90 $mm^2$, and usually no greater than about 450 $mm^2$ (such as for use in the aorta or other large lumen). The thickness of the first and second segments is generally in the range from about 100 to 500 microns and preferably in the range from about 200 to 400 microns. The width typically ranges from about 15% to about 100% of the target conduit, usually from about 25% to about 85% and more usually from about 50% to about 75% in those embodiments that are not configured as complete cylinders. Exemplary width and length (or diameter) dimensions for these surface area ranges are generally from about 5 mm to about 15 mm for the width and from about 8 mm to about 30 mm for the length. And more usually from about 7 mm to about 9 mm for the width and from about 13 mm to about 15 mm for the length, depending on the exact size of the target vessel to be anastomosed.

In addition, the flow opening has a diameter that provides for the desired flow rate between the two vessels connected by the device. The diameter of the flow opening (and connecting tube depending the particular embodiment) generally approximates the diameter of at least one of the vessels being joined by the device. As such, the diameter of the flow opening is typically at least about 1 mm, and usually ranges from about 1 mm to about 10 mm, usually from about 1.5 mm to about 8.5 mm and more usually from about 2.0 mm to about 7.5 mm., however the dimensions of the flow opening will vary depending on the particular application at hand and as such may, in certain embodiments, have a length dimension greater than 10 mm such that the length may be as great as about 10 mm to about 25 mm or more. In addition, the flow opening may be in the form of an ellipse whose short axis conforms to the specifications for the diameter and whose long axis is typically at least about 1 mm, usually at least about 2 mm and more usually at least about 3 mm, where the long axis may be as long as 5 mm or longer, but generally does not exceed 20 mm.

End-to-Side Anastomotic Devices

The end-to-side anastomotic devices of the present invention, like the side-to-side anastomotic devices of the present invention, are characterized by the presence of a first segment that, upon deployment, forms a sealing relationship with the inner surface of the vessel in which it is deployed. Connected to this first segment at a flow opening is a tubular member, which member is designed to be positioned within the transected end of a graft vessel to be joined to the side of a host vessel.

Figure 12A:
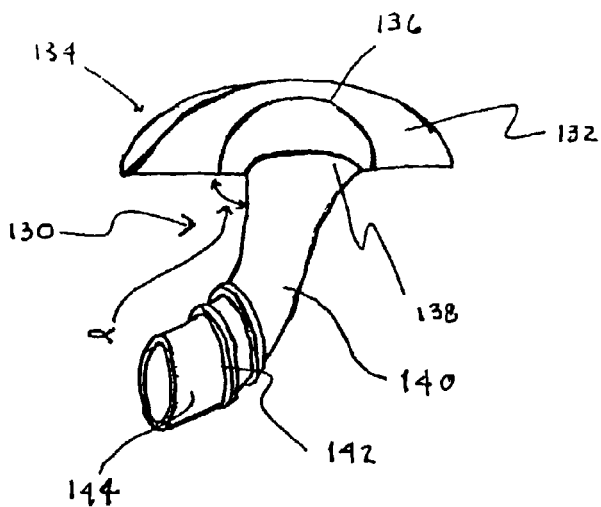
FIG. 12 includes FIGS. 12A and 12B which show an end-to-side embodiment of the invention.
FIG. 12B is a partial cut-away view of the tubular member of the device operatively positioned within a vessel.

Referring now to FIGS. 12A-B, 13, 14, 15A-C and 37A and 37B, there are illustrated end-to-side anastomotic device embodiments according to the present invention. The one-piece device 130 of FIG. 12A is made up of first segment 134 and a tubular member 140 joined together at flow opening defined externally by juncture 138. First segment 134 is shown as a partial cylinder having an elliptically shaped contact surface. As with the side-to-side embodiments discussed previously, first segment 134 may have any other appropriate shape (e.g., circular, elliptical, rectangular, petal-like, etc.) and configuration (e.g., a full cylinder, etc.). First segment 134 has a flange section 132 and a reinforcement portions in the form of annular ridge 136 which functions similarly to the reinforcement portions of device 50 of FIG. 9. The length, width, thickness and surface area dimensions of segment 134 are within the ranges provided above with respect to the first and second segments of the side-to-side embodiments.

Tubular member 140 of device 130 extends from the flow opening (not shown) of segment 134 and is designed to fit inside of the transected end of a graft vessel that is to be joined to the side of a host vessel. The length of tubular member 140 typically ranges from about 10 to 20 mm. The outer diameter of tubular member 140 has a dimension that approximates the inner diameter of the graft vessel to be attached, and therefore is typically in the range from about 2 to 6 mm, and more typically from about 3 to 5 mm. The inner diameter of tubular member typically ranges from about 1 to 5 mm, and more typically from about 2 to 4 mm. Also identified in FIG. 12A is juncture 138 at the connecting point between tubular member 140 and first segment 134 which, internal to device 130, defines the flow opening which typically has a diameter that is substantially the same as the inner diameter of the tubular member.

Figure 12B:
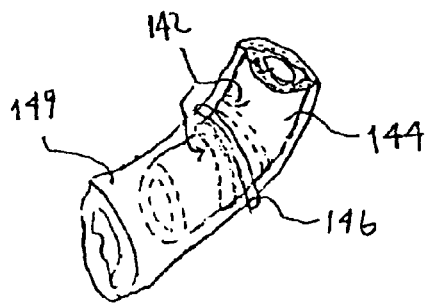

Tubular member 140 has distal end 144 having a vessel securement means 142. Here, vessel securement means is in the form of two parallel rings surrounding the circumference of tubular member 140. After tubular member 140 has been inserted into the graft vessel 149, as illustrated in FIG. 12B, and appropriately positioned vis-à-vis the host vessel (not shown), another component of the securement means, here in the form of a suture, cuff or ring 146 may be temporarily or permanently positioned about the graft vessel 149 and within the spacing formed by rings 142.

Figure 15A:
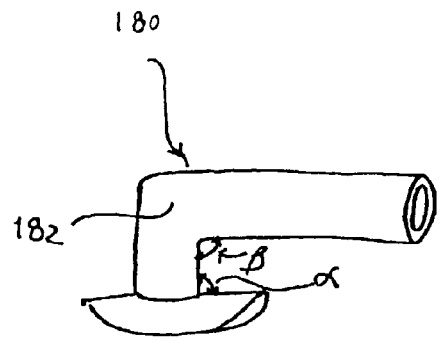
FIG. 15 includes FIGS. 15A, 15B and 15C which illustrate various exemplary end-to-side embodiments of the invention wherein the respective tubular members have varying configurations and are at varying angles to their respective segments.
Figure 15B:
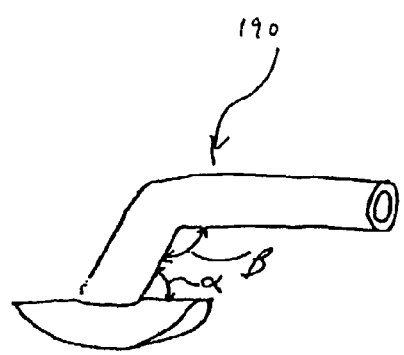
Figure 15C:
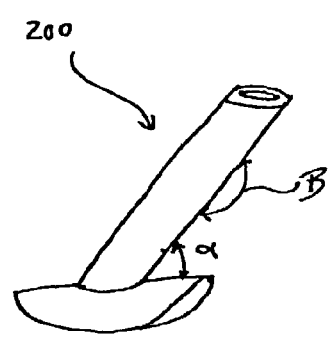

The positioning of tubular member 140 with respect to segment 134 and also the configuration of tubular member 140 may be selected in order to better present tubular member 140 within the surgical field and to facilitate visual and manual access by the surgeon particularly in a minimally invasive opening. For example, tubular member 140 may be angled with respect to first segment 134. While device 130 of FIG. 12A is depicted as having tubular element 140 normal to the upper surface of first segment 134 such that angle α is approximately 90°, tubular element 140 may also be non-normally angled with respect to the upper surface of first segment 134, depending on the particular anastomotic protocol in which the device is to be employed. As such, angle α may range from about 1° to 90°, and will typically range from about 5° to 90°, and will more usually range from about 20° to 90°. For example, FIGS. 15A-C illustrate exemplary configurations of angle α wherein the device 180 of FIG. 15A has an angle α of 90°, device 190 of FIG. 15B has an angle α approximately between about 50° to 60, and device 200 of FIG. 15C has an angle α approximately between about 30° to 45°.

The configuration of the tubular member may also facilitate presentation, access and positioning of the vessels being anastomized. Referring again to FIG. 12A, distal end 144 of tubular member 140 is curved but may have any appropriate configuration. For example, tubular member may have a bend or an elbow portion along its length defining an angle β is in the range from about 90° to 179°. Referring now FIGS. 15A-C, tubular member 180 of FIG. 15A has an angle β of about 90°. Tubular member 190 of FIG. 15B has an angle β at about 120°, while angle β of tubular member 200 of FIG. 15C is 180°, having a straight configuration. When operatively positioned, these tubular member configurations may also facilitate positioning of the graft vessel with respect to the native vessel such that the interconnected vessels lie relative to each other in a manner that minimizes any pulling tension that may occur from the natural beating of the heart. Depending on the particular anastomotic protocol in which the device is to be employed, angle β may range from about 90° to 180°. Furthermore, the values of angles α and β can be chose such that the combination of the two optimizes the particular anastomotic procedure at hand.

FIG. 37A shows an embodiment of an end-to-side device 550 which has the same general construct as device 150 of FIG. 12A; however, first segment 562 has a petaled shape. In this particular embodiment, four petals are shown, but it is to be understood that any number of petals may be employed. Accordingly, device 550 is made up of a flange 562 and a tubular member 564 joined together at a flow opening defined externally by juncture 568. Device 550 may or may not include reinforcement portions, as described above. Furthermore, tubular member 564 may be normal to the upper surface of flange 562 or may, in certain embodiments, be non-normally angled to the upper surface of segment 562, as described above with respect to device 150.

Side-to-side or end-to-end distances of flange 562 designated by arrows 563 and 567, shown in the top perspective view of anastomotic connector device 550 in FIG. 37B, may be the same or differ from each other. In certain embodiments, the flange may have a major axis, such as defined by arrows 563, and a minor axis, such as defined by arrows 567. The distance across the major axis may range from about 8 mm to about 30 mm, and more typically range from about 13 mm to about 15 mm. The distance across the minor axis may range from about 5 mm to about 15 mm, and more typically range from about 7 mm to about 9 mm. The flange is bendable or foldable about either axis, and thus, device 550 may be delivered in a folded or bent configuration such as by folding or bending about one or both axes, as required by the surgical application.

Figure 13:
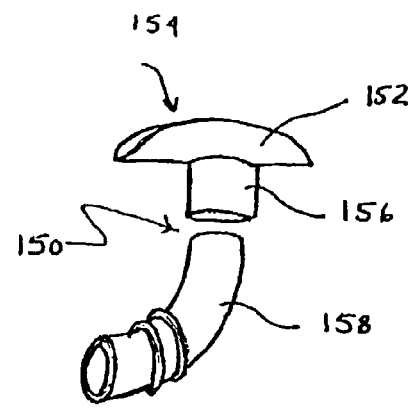
FIG. 13 shows another end-to-side embodiment having a two-piece configuration which pieces are connectable with each other for forming a fluid-tight seal between the segment and the tubular member.

Referring now to FIG. 13, there is shown a two-piece embodiment of an end-to-side device 150 which has the same general construct as device 130 of FIG. 12A. Here, however, tubular member 158 is a separate component from component 154 which includes a first segment 152 and a first fluid channel portion 156 extending from the flow opening (not shown) of segment 152. The coupling of tubular member 158 to fluid channel portion 156 is accomplished much in the same way that first piece 74 and second piece 76 of FIG. 10 are coupled together.

Figure 14:
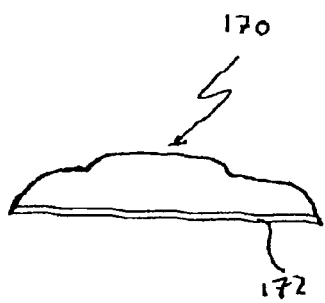
FIG. 14 illustrates another embodiment of a segment of the invention.

FIG. 14 shows a side view of an alternate embodiment of a first segment 170 of the present invention having a pleat 172, running centrally along the longitudinal axis of segment 170 to assist folding and deployment of segment 170 within a target vessel.

Closure Devices

The subject invention also provides implantable devices for closing openings in tissue, e.g., in body conduits or lumens, organs such as septal openings, etc., and sealing the openings to provide a substantially fluid-tight seal at the opening so that fluid does not leak out of the opening. For example, in the context of closing a vascular opening, the opening that is closed is sealed such that fluid from within the vessel does not leak out of the opening. Accordingly, the subject closure devices are implantable, i.e., permanently implantable, such that they are intended and configured to remain in the tissue or conduit, operatively aligned with the opening therein, after the opening has been closed and sealed by the device, where in certain embodiments the closure device is configured to be reabsorbed over time leaving a natural, permanent closure and seal at the opening. The subject closure devices may also be used to seal or patch irregularities present on a surface of tissue, e.g., on a surface of a conduit such as on an intravascular surface or the like, as will be described in greater detail below.

The tissue closure devices of the subject invention typically have a single segment, where the segment has the same or similar properties and features as the segments or flanges described above with respect to the subject anastomotic devices. That is, the closure devices have a segment that, upon deployment, forms a sealing relationship with the inner surface of the conduit or tissue structure in which it is deployed. More specifically, the subject closure devices have one segment that is insertable into a conduit or the like such as a vessel and is capable of conforming to and sealing with an inner surface of the vessel and further adapted to utilize the internal vessel pressure exerted thereon to form a substantially fluid-tight seal with the inner surface of the vessel whereby substances within the vessel are prevented from leaking from the opening in the vessel under normal physiological conditions, thereby closing and sealing the opening in the vessel wall.

Figure 16:
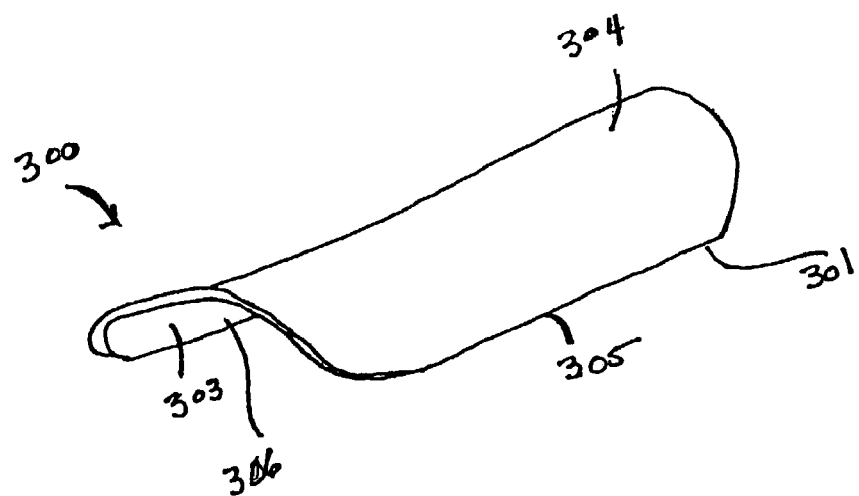
FIG. 16 shows a perspective view of an exemplary embodiment of a subject closure device.

Turning again to the Figures, FIG. 16 shows an exemplary embodiment of a subject closure device 300 in an unfolded or unconstricted configuration such that it is in a configuration to conform to the interior of a vessel to close and seal an opening in the vessel, i.e., in an original or tissue closing and sealing configuration. Closure device 300 may be correctly characterized as having segment 301 that has a lumen facing surface 303 and a conduit facing, i.e., conduit wall facing or tissue facing, surface 304.

Figure 17:
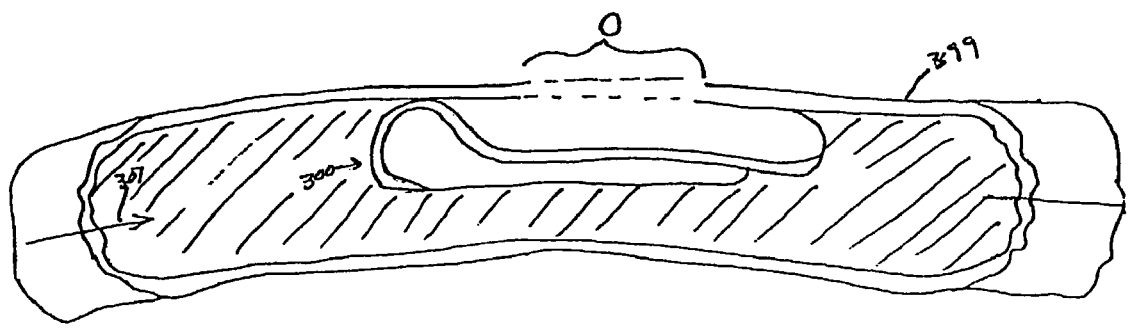
FIG. 17 shows the closure device of FIG. 16 operatively positioned within a vessel to close and seal an opening in that vessel.

FIG. 17 shows a partial cut-away view of vessel 399 having opening O and closure device 300 inserted into vessels 399 such that closure device 300 is operatively aligned with opening O of vessel 399 to close and seal the opening. In all embodiments of the subject invention, depending on the particular configuration of the closure device, the insertion of the closure device through the opening in the vessel or other tissue structure into the interior of the vessel may be carried out in a number of different ways. As an example, segment 301 may be constricted from an original state, either manually or by the aid of an insertion tool, so that it forms a tighter configuration. For example, sides 305 and 306 can be folded or bent towards each other. In this position, sides 305 and 306 may be made to touch each other and can be inserted within the opening of a vessel. Once properly seated within the vessel, the segment is released from its constricted state and allowed to deploy whereby respective sides 305 and 306 unfold or expand from the constrictable state and move against and conform to the inside vessel wall thereby establishing a substantially fluid-tight seal or barrier over the opening O while providing ample space for fluids to continue to flow through the vessel so as not to disrupt normal physiological functions. In other words, fluid is able to continue to flow along flow path 307 without disruption by implanted closure device 300. The pressure provided by closure device 300 due to expansion of segment 301 and the action of intraluminal pressure prevents leakage of fluid from the opening in the vessel. As such, when segment 301 expands back to its original size and shape from its constricted state in the interior of the vessel, it will conform to the vessel walls to provide a sealing pressure and a firm fit at the opening in the vessel, utilizing the internal vessel pressure exerted thereon.

Although closure device 300 shows segment 301 having a planar or slightly arched configuration, a variety of different shapes and configurations are contemplated by the present invention (see for example FIGS. 18, 19, 20, 21, 22 and 38). However, those skilled in the art will contemplate numerous additional embodiments upon reading this disclosure.

Figure 18:
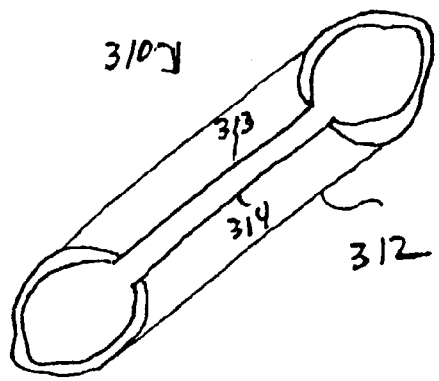
FIG. 18 shows a perspective view of another exemplary embodiment of a closure device according to the subject invention.

FIG. 18 shows another exemplary embodiment of the subject invention. Closure device 310 in FIG. 18 has a segment 312 that nearly forms a complete cylinder. The edges 313 and 314 are close to each other compared to those of the device shown in the configuration of FIG. 16, which forms half or less than half of a cylinder. Device 310 is inserted into a vessel and forms a sealing relationship with the walls of a conduit to provide a substantially fluid-tight seal around an opening thereof in the manner described above.

Figure 19:
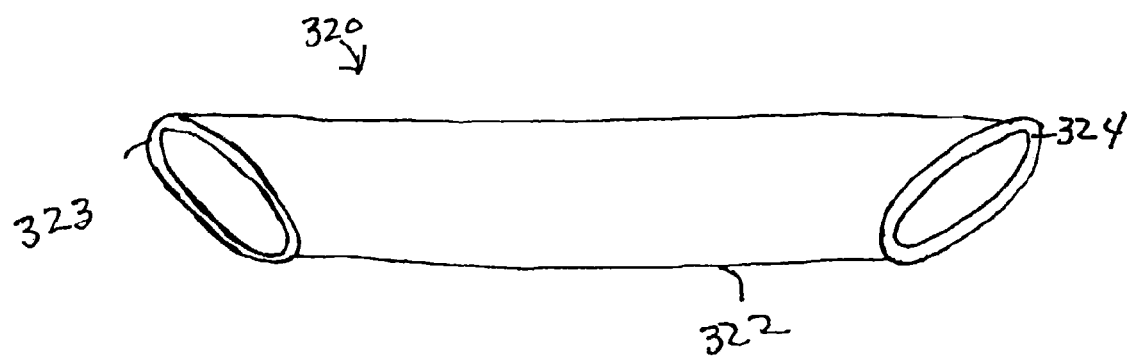
FIG. 19 shows a perspective view of another exemplary embodiment of a closure device according to the subject invention.

FIG. 19 shows an alternative embodiment of the invented closure device 320 having a segment 322 in the form of a complete cylinder. Device 320 is inserted into a vessel and forms a sealing relationship with the walls of a conduit to provide a substantially fluid-tight seal around an opening thereof in the manner described above.

Segment 322 has tapered or angled ends 323 and 324. The tapering of these ends may have a low friction coating and be very smooth, thereby providing a number of advantages which include making it easier to insert into an opening in a vessel. As described above, closure device 300 in FIG. 16 and closure device 310 in FIG. 18 are configured in the form of a portion of a cylinder in an unconstricted or original state. However, the devices could be configured so that the segments are complete cylinders, as shown in FIG. 19, in an unconstricted or original state and/or in a constricted state.

As mentioned above with respect to the subject anastomotic devices and which is also applicable to the subject closure devices, an advantage of having the segment configured as a partial cylinder is the ability of a partial cylinder segment to conform to a wider range of different vessel diameters to improve the fitting range than a complete cylinder configuration. Another advantage of a partial cylinder segment is the ability to maximize a greater amount of the vessel wall, e.g., the endothelial wall of the vessel, not covered by a closure device to minimize any negative biological response to the implantable device. On the other hand, a complete cylinder configuration as shown in FIG. 19 may be desired for patching and sealing surface irregularities such as large irregularities, for example.

Figure 20:
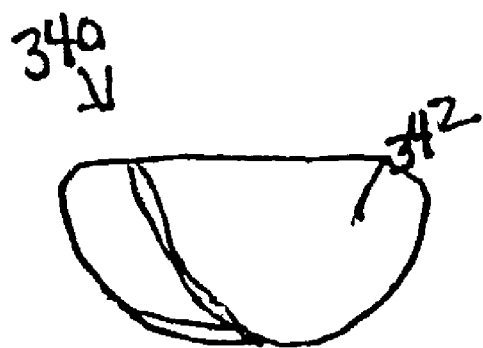
FIG. 20 shows a perspective view of yet another exemplary embodiment of a closure device according to the subject invention.

FIG. 20 shows another exemplary embodiment of a subject closure device 340 having a segment 342 having a substantially elliptical shape when in an unfolded or unconstrained configuration. When inserted into a vessel, organ or other conduit or tissue structure, device 340 forms a sealing relationship with the walls of the tissue, e.g., the walls of the vessel, to provide a substantially fluid-tight seal across an opening thereof in the manner described above.

Figure 21:
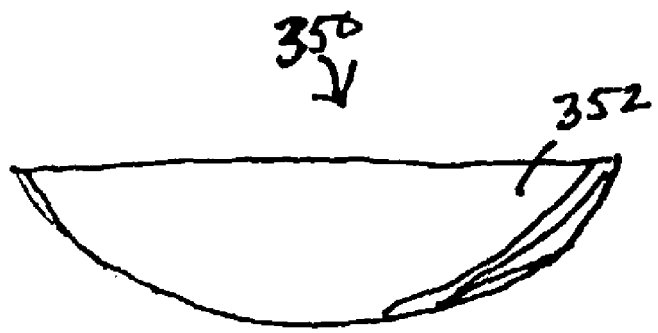
FIG. 21 shows a perspective view of another exemplary embodiment of a closure device according to the subject invention.
Figure 22:
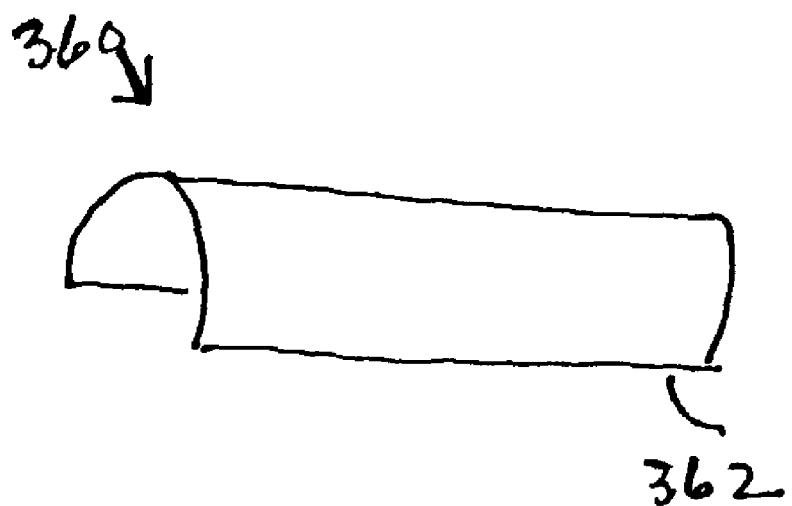
FIG. 22 shows a perspective view of another exemplary embodiment of a closure device according to the subject invention.

FIG. 21 shows yet another exemplary embodiment of a subject closure device 350 having a segment 352 having a substantially circular shape when in an unfolded or unconstricted configuration. When inserted into a vessel, organ or other conduit or tissue structure, device 350 forms a sealing relationship with the walls of the tissue, e.g., the walls of the vessel, to provide a substantially fluid-tight seal across an opening thereof in the manner described above.

FIG. 22 shows an exemplary embodiment of yet another embodiment of a closure device of the subject invention. Device 360 has segment 362 having a rectangular contact surface which, when in constricted conditions, has a semi-cylindrical configuration. When inserted into a vessel, organ or other conduit or tissue structure, device 360 forms a sealing relationship with the walls of the tissue, e.g., the walls of the vessel, to provide a substantially fluid-tight seal across an opening thereof in the manner described above.

Figure 38:
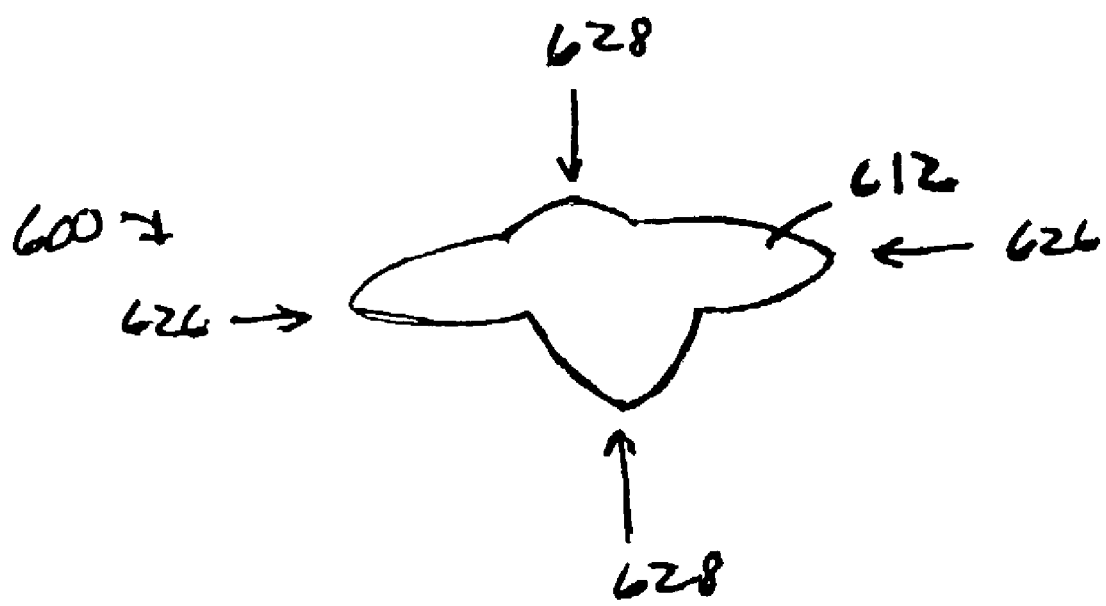
FIG. 38 shows an alternative embodiment of a closure device of the subject invention.

In certain embodiments, it may be desirable to employ a closure device that has an irregular or complex shape. FIG. 38 shows an exemplary embodiment of a subject closure device 600, shown here in an original or unconstricted state. Device 600 includes segment 612 having a petaled shape. In this particular embodiment, four petals are shown on each flange, but it is to be understood that any number of petals may be employed, where the number of petals present may vary. Side-to-side or end-to-end distances of segment 612 designated by arrows 626 and 628 may be the same or may differ from each other. In certain embodiments, the segment may have a major axis, such as defined by arrows 626, and a minor axis, such as defined by arrows 628. The distance across the major axis may range from about 8 mm to about 30 mm, and more typically range from about 13 mm to about 15 mm. The distance across the minor axis may range from about 5 mm to about 15 mm, and more typically range from about 7 mm to about 9 mm. The segment is bendable or foldable about either axis, and thus, device 600 may be delivered in a folded or bent configuration such as by folding or bending about one or both axes, as required by the surgical application.

The segments of the closure devices of the present invention may include a pleat (not shown with respect to a closure device), running centrally along the longitudinal axis (or any other appropriate axis) of the segment to assist folding and deployment of the device within a target vessel.

In all embodiments of the subject closure devices, an aperture may be provided to enable deployment in the interior of a conduit over a guide wire (or guide catheter in certain instances). In this manner, a guide wire that is operatively positioned through an opening in a conduit wall for a procedure may be used to deploy a subject closure device to the interior of the conduit over that guide wire. As such, at least a portion of the device, e.g., an area within or around the aperture, may include a thrombogenic substance that promotes closing and sealing of the opening by thrombosis and/or the aperture is self-closing and self-sealing for example after penetration by and removal of a guide wire, as will be described in greater detail below.

FIGS. 23-30 shows exemplary embodiments of the subject closure devices having various shapes and configurations of apertures, where the figures provided are for exemplary purposes only and are in no way intended to limit the scope of the invention as any appropriately shaped and/or configured aperture and segment may be employed.

FIG. 23 shows an exemplary embodiment of closure device 400 which is shaped similarly to device 300 of FIG. 16; however, any shaped device may be used. Device 400 includes aperture 405 positioned through segment 401. Aperture 405 may be any shape. For example, aperture 405 may be a simple shape such as oval (shown here), circle, oblong, square, rectangle, triangle, or the like or may be a complex or irregular shape. Aperture 405 may be any convenient size and will be capable of accommodating a guide wire or similar delivery device therethrough. As mentioned above, an area adjacent or surrounding aperture 405 may include a thrombogenic material that promotes a thrombogenic response by the blood flowing through the conduit in which closure device 400 is seated at the site of the aperture so that the resultant thrombus closes and seals the opening in the conduit wall, i.e., provides a natural and permanent closure and seal. In certain embodiments, a thrombogenic substance may be coated or lined about aperture 405, e.g., around the circumference of aperture 405. Aperture 405 may also be filled with a thrombogenic substance for example aperture 405 may include a "plug" of a thrombogenic substance. Still further, aperture 405 may be covered or filled with a substance, element or material that is permeable to a guide wire or other delivery instrumentation, but that automatically closes and/or hardens around the aperture to prevent fluid flow therethrough once the guide wire or instrumentation is removed therefrom, i.e., the aperture is self-sealing and impermeable to fluid once sealed. For example, the aperture may include a material that closes in on itself after the guide wire has been removed or the aperture may include a one-way or hemostatic valve. The material around the aperture may harden and thus close the aperture upon contacted with blood, where such may be accomplished using processes involving coagulation, polymerization, precipitation, ionization, etc., or a combination thereof. In certain embodiments, the aperture is covered by a thin membrane or the like such as a blood-impermeable membrane or a mesh such as a wire mesh or the like that is penetrable by a guide wire or similar delivery device. The membrane or wire mesh may provide a physical structure to which a thrombogenic substance may be attached. In certain embodiments, the thin membrane cover is self-closing and sealing such that upon removal of a guide wire or similar delivery device from the membrane or wire, the opening created by the guide wire or other delivery device is closed and sealed automatically, e.g., by the closing of a valve or closing in of the material of the membrane, immediately following removal of such from the membrane.

FIG. 24A shows an exemplary embodiment of a device 410 similar to device 25 described above; however device 410 has an aperture 415 that is surrounded and covered by radially extending fingers or flaps such as fingers 416 fabricated from nitinol or other shaped-memory material. Any number of extensions or fingers may be employed. FIG. 24B shows and enlarged, top view of aperture 415 and fingers 416. Device 410 includes a thrombogenic substance about aperture 415 and/or a self-sealing cover, as described above with respect to FIG. 23.

FIG. 25A shows another exemplary embodiment of a subject closure device 420 which is shaped similarly to device 300 of FIG. 16; however again any shaped device may be used. Device 420 has segment 421 and aperture 425 configured as a slit along a portion of the longitudinal axis of segment 421. Device 420 may have any number of slits in any arrangement or pattern. FIG. 25B shows an enlarged view of slit 425. Device 420 includes a thrombogenic substance and/or a self-sealing cover and/or shaped-memory fingers about slit 425, as described above with respect to FIGS. 23 and 24A-24B.

FIG. 26A shows another exemplary embodiment of a subject closure device 430 which is shaped similarly to device 300 of FIG. 16; however again any shaped device may be used. Device 430 has segment 431 and aperture 435 configured as a slit having a cross-like pattern. It will be apparent that a variety of different patterns may be employed such as a starred pattern, an asterisk-shaped pattern, and the like (not shown). FIG. 26B shows an enlarged view of crossed slit 435. Device 430 includes a thrombogenic substance and/or a self-sealing cover and/or shaped-memory fingers about cross 435, as described with respect to FIGS. 23 and 24A-24B.

In certain embodiments, the subject closure devices include a stoma or elongate portion which extends a distance above an aperture on the conduit contacting surface of a closure device. Such stomas provide an area for retaining a thrombogenic substance that is greater, or rather has a greater thickness or volume, than an aperture without such a stoma, which would be about the thickness of the segment. A stoma may be any convenient shape and size, where the selection of the shape and size employed in a closure procedure may be dictated, in part, by the shape and size of the opening to be closed and sealed.

Accordingly, FIG. 27 shows an exemplary embodiment of a closure device 440 having aperture 445 and stoma extension 447 extending therefrom, i.e., extending above conduit contacting surface 444. Stoma extension 447 defines a channel through which a guide wire or similar delivery device may be accommodated. As described above, the interior of stoma 447 may be coated or layered with a thrombogenic substance and/or may be filled with a thrombogenic substance such as in the form of a plug or the like that is penetrable by a guide wire and/or covered by a membrane that is self-sealing and/or coated with a thrombogenic substance and/or covered by a shaped-memory material such as radially extending fingers or flaps, etc. Stoma 447 may also include a valve, as described below.

FIG. 28 shows a cut-away view of vessel 498 having opening O in a wall therein and device 440 of FIG. 27 deployed in vessel 498 and operatively positioned therein to close and seal opening O. As shown, stoma 447 is positioned within opening O and is substantially flush with the outer wall of vessel 498. As will be apparent, the stoma may have any length or diameter, where in many embodiments the stoma is at least substantially flush with the outer vessel wall, i.e., will not usually extend too far beyond the outer vessel wall; however, the stoma may have a length that is less than the length or thickness of the opening into which it is positioned.

In order to provide a smooth transition or interface between the device and the outer vessel wall, the stoma may be contoured or shaped to provide an intimate contact or transition with the outer vessel wall or area of a tissue structure with which it is used. FIG. 29 shows an exemplary embodiment of such a contoured stoma. Device 450 has segment 451 and opening 455. The sides of stoma 457 are contoured so that the tops of the stoma overlay the outer wall of the vessel without damaging the vessel wall. In other words, the stoma does not puncture or compress the vessel wall. As described above, the stoma may include a coating and/or filling of a thrombogenic substance or may include a physical structure such as a membrane or plug that may serve as a scaffold to which a thrombogenic substance is attached and/or which may be self-sealing.

Figures 31, 32:
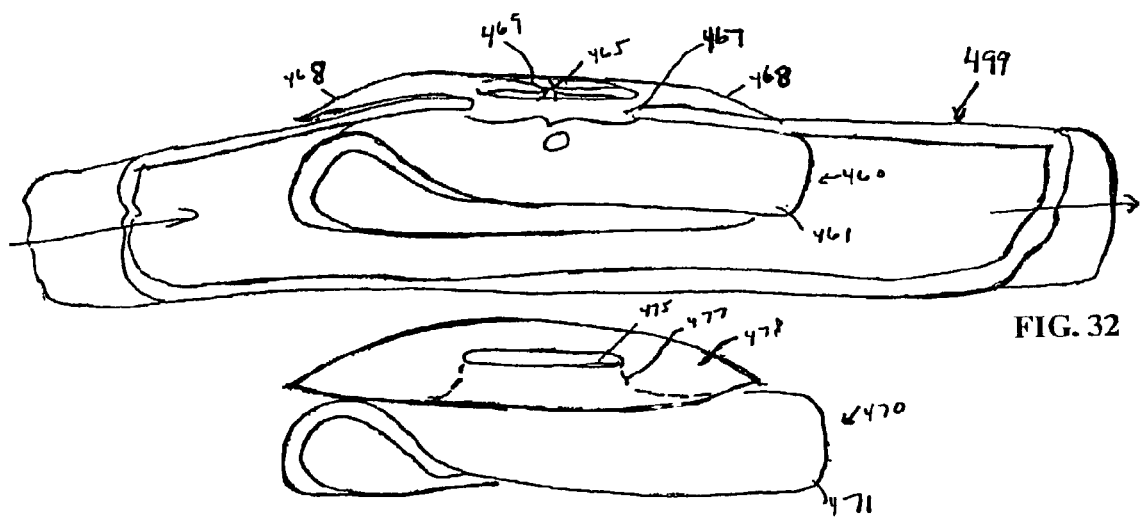
FIG. 31 shows a perspective view of another exemplary embodiment of a subject closure device having a stoma with a transition portion in the form of a complete circle.
FIG. 32 shows the device of FIG. 30 operatively positioned in a vessel.

In certain embodiments, the top portion of the stoma may be elongated or include extensions, i.e., a transition portion or more specifically a tissue transition portion, or the like to further smooth the interface between the device, more specifically between the stoma and the outer vessel wall or tissue structure with which it is used, and in certain instances such transition portion may assist in securing the device to the tissue surrounding the opening to be closed. FIG. 30 shows an exemplary embodiment of such a device. Device 460 includes segment 461 having stoma 467 with aperture 465. As shown, stoma 467 has elongated portions or extensions or flaps 468, herein shown as two extensions positioned on opposing sides of stoma 467, however any number of extensions may be used such that the extensions, in certain embodiments, may be a complete circle or the like. The extensions do not puncture or compress or otherwise create tension on the vessel wall or tissue surrounding the opening, but rather function to provide a smooth transition from the stoma and may also provide a means to help secure the device in place at the opening to be closed. The extensions may be made of nitinol or other shaped memory material, i.e., radially extending fingers or flaps as described above. FIG. 31 shows an exemplary embodiment of a closure device 470 having a transition portion 478 that does not have "fingers", but rather is a solid member in the shape of a circle, oval, complex or irregular design, or the like. As described, the stoma may include a thrombogenic substance operatively positioned with respect to the stoma and/or a thin blood-impermeable membrane cover or the like that is penetrable by a guide wire or other similar delivery device and which is capable of self-sealing following the removal of the guide wire or delivery device from the membrane, etc.

FIG. 32 shows how the transition portions 468 of a subject stoma provide a smooth interface between the stoma and the exterior wall of a vessel without puncturing or compressing the vessel wall. Accordingly, FIG. 32 shows a cut-away view of a vessel 499 having device 460 of FIG. 30 operatively positioned therein and within opening O. As shown, vessel transition portions 468 are contoured to overlay substantially flatly onto the exterior or outer wall of vessel 499 to provide a smooth transition from the stoma.

In all such embodiments of the subject closure devices having an aperture, one or more flow directing elements may be provided that is capable of preventing the flow of fluid out of the aperture during device deployment and placement, i.e., before thrombosis occurs to close and seal the opening, such as a one-way or hemostatic valve, a sol or gel or any material that forms an intimate contact with the delivery instrumentation positioned in the aperture so as to prevent flow there past. FIGS. 30 and 32 show a valve 469 operatively positioned within the aperture of the device which prevents blood flow out of the vessel through the aperture. Any suitable valve may be employed such as a one-way valve, hemostatic valve and the like.

While a number of different shapes and configurations are possible for the subject closure devices, as demonstrated above by the review of some exemplary shapes and configurations, in all embodiments the area of contact between the deployed segment and the tissue with which it is used should be sufficient to provide for a sealing contact of sufficient strength to achieve the purpose of the device. Accordingly, the segment of a subject closure device has a surface contact area, i.e., an area that contacts a surface of the tissue such as a surface of a vessel, at least marginally greater than the surface area of the opening in the tissue, e.g., the opening in a vessel, through with the segment is inserted and which is to be closed and sealed thereby. By way of example and in no way intended to limit the scope of the invention, for devices suitable for use in closing openings in a femoral artery in the groin area, for example openings created to provide access for surgical instrumentation for an angioplasty or stent placement procedure or the like, the diameter of the opening typically ranges from about 2 mm to 10 mm, usually from about 2 mm to about 6 mm. Accordingly, the contact surface of a segment suitable for use in closing such an opening typically has a surface area that is generally at least about 10 $mm^2$ to about 100 $mm^2$, and usually ranges from about 20 $mm^2$ to about 80 $mm^2$, more usually ranges from about 20 $mm^2$ to about 45 $mm^2$ or to about 50 $mm^2$, where in certain embodiments the surface area may be greater than about 100 $mm^2$, such as greater than about 110 $mm^2$ or even greater than about 120 $mm^2$. The thickness of the segment is generally in the range from about 100 to 500 microns and usually in the range from about 200 to 400 microns, where in certain embodiments the thickness may be less than about 100 microns or greater than about 500 microns, depending on the size of the vessel, the size of the opening to be closed, etc. Exemplary width and length (or diameter) dimensions for these surface area ranges are generally from about 5 mm to about 15 mm for the width and from about 8 mm to about 30 mm for the length; however these dimensions may vary as appropriate for the procedure at hand.

Materials

The subject closure devices, anastomotic devices and their components described above may be fabricated from a variety of different materials. The materials are generally biocompatible by which is meant that they are acceptable for implantation in the body and any adverse bodily reaction to their presence, if any, is not so great as to outweigh the benefit of the device when employed for its intended use. In certain embodiments, the devices are made from a biodegradable or bioresorbable material, where the terms biodegradable and bioresorbable are used interchangeably in this specification. Bioresorbable materials of interest include, but are not limited to, degradable hydrogels, polymers such as lactides/glycolides or PHAs; protein cell matrices, plant, carbohydrate derivatives (sugars), and the like. A metal mesh with the appropriate geometrical features, sinusoidal and circular, and cross patterns to provide adequate flexibility may be appropriate in certain circumstances; nitinol (a super elastic nickel titanium alloy) or other shape memory materials or stainless steel, vitalium or titanium can be used. Non-resorbable polymers and elastomers such as silicones, fluoropolymers, polyolephins or polyurethanes might also be used. In addition, the subject devices can be fabricated from composites of two or more different types of materials, etc. e.g., the device may be fabricated from a blood impermeable membrane attached to a structural article or scaffold.

Those skilled in the art will recognize that certain materials are preferred in connection with certain uses of the invention.

In general the material should be comprised of one or more materials which are biocompatible and non-toxic to the vessels into which they are inserted. In general the device is used for connecting vessels or closing and sealing openings in vessels of the cardiovascular system and therefore should be comprised of a material which provides a high degree of hemocompatibility. The material should not prevent growth of a new intima layer. The material used in the construction of the invented device should be designed to have thickness and properties appropriate for the stiffness and flexibility of the vessel into which the device is inserted. It should be noted that artery walls continuously dilate and contract due to the systole and diastole of the heart. If the device is too rigid the device can cause irritation and injury to the intima layer of the vessel. Accordingly, the device should be designed to avoid any inflammatory response or immune response that has adverse consequences. In addition to having the desired degree of flexibility and composition the device should be designed so that it does not present protrusions or disruptions to the flow of material through the vessels which are being connected or closed by the device. Interruption of flow can cause clots to form which could in certain circumstances be fatal to the patient.

In a preferred embodiment the device of the invention is bioresorbable material and it may be comprised of all or any of the following materials: Collagen, Polycaprolactone, Poly (glycolic acid), PLLA, Poly(3-hydroxybutric acid), Poly(dl-lactic acid), Poly(l-lactic acid), Poly(lactide/glycolide) copolymers, Poly(hydroxyvalerate), Poly(hydroxyvarelate-co-hydroxybutyrate), or other PHAs, or other resorbable materials, e.g., protein cell matrices, plant, carbohydrate derivatives (sugars); and the like. Further, see the materials disclosed and described in U.S. Pat. No. 5,056,211 as well as patents and publications cited therein. In instances where the device is made of a biodegradable material, such as a hydrogel material or a biological or synthetic polymer having a porous structure, the porous structure may serve as a scaffold for tissue in-growth to anchor the device to the conduit in which it is implanted, and thus promote angiogenic and arteriogenic growth between the device and the conduit. As the device biodegrades, the angiogenic and arteriogenic processes take over to form a more natural and permanent seal to the opening. Advantages of employing resorbable devices include the fact that, when resorbed, the devices leave behind a healed 'stoma' such that the anastomosis or conduit is completely physiologic, with no foreign body present. It is also possible to produce a device that is comprised of metal or has a metal mesh substructure coated with a polymer or bioabsorbable material, e.g., a blood impermeable membrane as described above. When the device is comprised of metal or includes metal components, the metal must be sufficiently flexible to provide the desired degree of flexibility in the vessels it is used in. The geometric pattern of the metal within the device may be important to obtaining preferred results and may be a woven, sinusoidal or circular metal substructure. The device may be comprised of surgical grade stainless steel, vitalium or nitinol which has useful superelastic properties. Polymers may be used not only to coat metals but to produce the entire device. Non-resorbable polymers and elastomeric materials such as silicone or fluoropolymers can be produced in the desired size, shape and flexibility.

With respect to the segment or flange portion in particular, materials such as polymers may be used to fabricate the segment or flange in either solid form as a thin section or membrane, or used in a woven or expanded foam state. Suitable polymers include elastomers, such as polyurethane and polysiloxane, or PTFE used in vascular grafts. Elastomers such as polyurethane allow a small amount of local deformation to aid in sealing. Due to the special deformation properties of elastomers, commercial elastomers are typically specified by hardness, with flexural and tensile modulus usually scaling in rough proportion to hardness. Experiments have shown elastomers with a durometer ranging from 80 Shore A (soft) to 55 Shore D (hard) have been suitable for use, with corresponding changes in flange thickness to achieve appropriate mechanical properties for deployment.

Other suitable segment or flange materials include fabrics used for vascular grafts such as Dacron and carbonaceous materials such as carbon fibers. Composite structures for the segment or flange may also be utilized, in the form of reinforcing struts or components to aid mechanical deployment and implant stability. Suitable reinforcing materials for the segment include metals such as stainless steel, titanium, vitalium, nitinol, structural polymers such as polycarbonate, polythethylene, and polypropylene. For further stability, the tubular member may be reinforced with a wound wire or other anti-kinking means. Any suitable material described herein may also be used for the fabrication of the stoma and tissue transition portions of a subject closure device. For example, a transition portion may be made of a memory metal such as nitinol, a polymer, urethane or a combination of more than one material such as a polymer lined with nitinol or other reinforcement material. As mentioned above, in those embodiments where the closure device is made from reabsorbable material, the associated stoma and transition portions will also be reabsorbable. As mentioned above, a stoma may be covered by a thin membrane such as a blood-impermeable membrane or scaffold or other physical structure to which a thrombogenic promoting material may be adhered or embedded, where such a structure may be fabricated from any of the materials described herein. The thin membrane may, in certain cases, be made of a thrombogenic material. In certain embodiments, the thin membrane is capable of automatically sealing an opening therein created by a guide wire or other delivery device upon removal of such a guide wire or delivery device from the membrane.

Any or all of the different materials can be coated with a desired compound or drug. The device blood-contacting surface may be lined with endothelial cells. These cells may be cells extracted from the patient within which the device is being placed or from a tissue culture of such cells from another patient. Such "endothelial seeding" is known in the art and generally utilizes viable endothelial cells which are seeded onto a surface to mimic the surface of natural blood vessels. The goal of this endothelial seeding technique is to produce a confluent, biologically active surface of viable endothelial cells, i.e., produce a surface that is anti-thrombogenic. The endothelial cells may be seeded directly onto the surface of a subject closure device or may be positioned on the surface following expansion in a cell culture. The subject devices may also be seeded or coated or layered (and/or embedded) with selected agents including but not limited to angiogenic and/or arteriogenic growth factors, mitogenic factors, antiplatelets, anticoagulants and other proteins, stimulants, adhesives, etc. Such coatings, seedings, agents, etc., may promote a natural, permanent closure/seal at the opening. In certain embodiments, an adhesive agent may be coated or layered, partially or completely, on one or more surfaces of the subject devices to promote securing of the device within the vessel wall.

One or more surfaces of the subject closure devices may be chemically or physically modified. For example, one or more surface, i.e., the lumen-facing surface and/or the conduit wall-facing surface, may be modified to facilitate adhesion of a coating or layer of one or more substances as described above such as to facilitate the seeding of endothelial cells, adhesion of growth factor, mitogenic factors, tissue stimulants, etc. A variety of surface modifications may be employed, where the particular surface modification employed will vary depending on a variety of factors such as the material of the device, the purpose of the modification, etc. Representative surface modification techniques include, but are not limited to, etching, adding or altering chemical moieties, altering surface charges, and the like. In certain embodiments, one or more surfaces may include one or more partial or complete holes (i.e., holes that extend the entire thickness of the device), e.g., laser ablated holes, where holes may be provided in varying degrees of sizes, various shapes and patterns, etc. The holes may promote tissue healing, e.g., vessel wall healing. For example, the holes may be designed to promote the full endotheliazation of the device into tissue such as into a vessel wall or otherwise promote the adherence of the device to the tissue such as adherence to a vessel wall.

As described above, in closure devices having an aperture, a thrombogenic substance, or plurality of substances, may be provided on or in the device at or around the area of the aperture to promote a thrombogenic response at the opening. The thrombogenic substance may be any suitable substance that promotes thrombosis or clotting, where representative thrombogenic substances include but are not limited to collagen, thrombin, gel foam, platelet activating materials, etc. Such thrombogenic substances may be coated, layered, embedded or otherwise suitably associated with the device. For example, the interior of the aperture, stoma or the like or an area around such may include one or more thrombogenic substances, where the thrombogenic substance(s) may be in any convenient form such as a layer, film, coating, membrane, foam, gel, sol, solid plug or the like. The thrombogenic material may also be associated with a one-way valve employed to prevent blood flow out of the vessel through the stoma.

Further, the materials may be embedded with any desired compound or drug which provides desired properties to the device. Useful coatings include drugs such as heparin which may be used alone or in combination with hydrogels or hydrophilic compounds. Any anticoagulant compound may be extremely useful as a coating on devices inserted into the vessels of the cardiovascular system.

A device of the invention may be comprised of any material that is appropriate for localized delivery of various compounds including compounds such as antiplatelet agents, calcium agonists, antiinflammatory compounds, antiproleferative drugs, hypolipidemic agents, and angiogenic factors. The device may be comprised such that all or any of these compounds are coated on the surface of the material, embedded within it or incorporated within a chamber (not shown) of the device so that the compound is released in a metered fashion from the device to the area surrounding the anastomosis.

In certain preferred embodiments, the devices are bioprosthetic devices fabricated from tissue, e.g., autologous, allogenic or xenogenic tissue. The tissue may be any convenient tissue that is capable of providing the appropriate flexibility and rigidity to the final bioprosthetic device, e.g., after one or more processing or "fixing" steps, such that the device is capable of serving its intended purpose. In many embodiments, the tissue is collagenous in nature, by which is meant that a substantial component of the tissue is collagen. Tissues of interest include, but are not limited to: pericardium, connective tissues, e.g., dura matter, tendons, ligaments, skin patches, mucosal patches, omentum, arteries, veins and the like, where the tissue is generally mammalian in nature, where specific species of interest include cow, horse, pig, sheep, primates, e.g., monkeys, baboons, and humans, where in many embodiments, the tissue will be of human origin, e.g., where the tissue may be an auto- or allograft, e.g., from a live person or a cadaver. Following harvest of the suitable tissue, the tissue is cut or shaped to the desired configuration, where the tissue may be manually shaped or shaped at least partially with the help of specialized tools/machines, e.g., die cutting devices, etc. At some point during preparation, the tissue may be processed to provide for one or more desirable attributes, where processes of interest include cross-linking, immunogenicity minimization modification, e.g., by fixation, modification to reduce enzymatic attack, and the like. Representative bioprosthetic materials and methods for their manufacture which may be readily adapted by those of skill in the art to fabricate anastomotic devices according to the present invention are described in U.S. Pat. Nos. 6,106,555; 6,093,530; 6,008,292; 5,984,973; 5,855,617; 5,609,600; 5,595,571; and the like, the disclosures of which are herein incorporated by reference.

Methods

Anastomotic Methods

As indicated above, the devices and methods of the subject invention may be employed to join any two or more vessels together, where the subject methods are particularly suited for joining vessels together that are located, or are to be located, in a living animal, e.g., the human body. The subject devices and methods are particularly suited for use in joining vascular vessels, where any type of vascular vessel may be joined to another vessel, where representative types of vascular vessels include, but are not limited to: coronary vessels, peripheral vessels, neurovascular vessels, etc. As such, the subject devices and methods can be used in a variety of applications, including coronary bypass applications, including both proximal and distal anastomoses, peripheral vascular bypass applications, neurovascular bypass applications, AV fistula formation, and the like. The vessels that are joined may be naturally occurring vessels, e.g., autologous donor to a graft, etc., or synthetic/fabricated vessels, e.g., synthetic vein, artery grafts, prosthetic tubes, etc. In those embodiments where the subject devices are intended to join vascular vessels together, e.g., human vascular vessels, they are dimensioned or shaped so as to work with the target vessels to be joined, e.g., they are shaped or dimensioned such that they fit within the human vessels, e.g., arteries, veins, to be joined.

The device of the invention in any of its embodiments may be inserted without the use of special surgical tools. Specifically, the device may be inserted manually (i.e., using the surgeon's fingers alone) or in combination with other surgical equipment normally used when operating on a patient. The subject methods may be performed intravascularly or extravascularly, i.e., an intravascular or extravascular approach may be employed with the subject devices. In intravascular methods, the device is delivered to the anastomotic site through a vessel, e.g., the donor or host vessel, where any convenient delivery means may be employed, including the delivery sheaths and devices described infra. For extravascular protocols, the device is introduced to the anastomotic site from outside of the vessel.

The present invention provides for the following general steps for interconnecting vessels using a flexible device of the present invention in which a first member is connected to a second member along a periphery of an opening in the first member and in the second member. First, the first member is bent to a reduced size, and then inserted into an opening of a vessel. When released, the first member expands to its original configuration and conforms to an inner surface or circumference of the vessel. The second member is inserted into the opening made in a second vessel. The surgeon then has the option to further secure the vessels to the device and to each other, or in other protocols, to secure the second vessel to the second member. This can be done by applying an adhesive between a surface of the member and a surface of the vessel, or by using a securement member (such as a cuff, collar or ring) positioned about the two.

More particularly, for side-to-side anastomoses, the side-to-side devices described above are employed to join two vessels in a side-by-side relationship, e.g., as shown in FIG. 2. In these methods, openings or slits are first prepared in the sides of the graft and host vessels. The openings or slits are sufficiently large to allow insertion of the first or second segments in a constricted or bent configuration, but are small enough such that the first or second segment cannot readily be pulled out of the vessel through the opening upon deployment of the segment and the first and second segments provide a leak free seal around the openings or slits. In many embodiments, the openings will be slits ranging in length from about 2 to 8 mm, usually from about 4 to 6 mm. Next, the first and second segments are inserted through the openings and allowed to deploy in a manner that produces a sealing relationship between the upper surface of the segment and the inner wall of the vessel. The above steps result in the establishment of fluid communication between the lumens of the host and graft vessels such that the two vessels are anastomosed to each other in a side-to-side configuration.

The end-to-side anastomosis protocols of the present invention are somewhat analogous to the side-to-side protocols and summarized above. In the end-to-side protocols, an opening or slit is prepared in the side of the host vessel, as described above. Next, the first segment of the end-to-side device is inserted through the opening and allowed to deploy. Depending on the particular protocol employed, the tubular member of the device may or may not have been pre-secured to the open end of the graft vessel. To secure the open end of the graft vessel to the tubular member, the open end of the graft vessel is placed over the tubular end of the device in a manner that provides for a secure positioning of the graft vessel over the tubular member. In certain embodiments, the dimensions of the tubular member are slightly larger than the inner diameter of the graft vessel such that the open end of the graft vessel must be stretched to slide it over the tubular member and, upon release of the stretching force, constricts with sufficient force to secure it to the tubular member. In other embodiments, a securing means may be employed to secure the end of the graft vessel to the tubular member. Securing means of interest include bioglues, sealing rings that can be slid the graft vessel/tubular member structure followed by constriction to secure the vessel to the tubular member, i.e., annular or ring securing means that move from a first expanded to a second constricted position, such as those described in U.S. Pat. No. 6,056,762, the disclosure of which is herein incorporated by references, ties, loops or lashes to secure the vessel to the tubular member, and the like.

As indicated above, any suitable delivery protocol may be employed. In connection with intravascular delivery of the device, it may be desirable to provide the device of the invention using a catheter or surgical dispenser through which the device is moved and inserted. FIGS. 6A, 6B and 6C illustrate a simple representation of how the device can be inserted using a surgical dispenser for bypass surgery with direct access to the heart.

The device such as the devices shown in FIGS. 1, 3, 5, 9, 10, 11 as well as any alternative embodiment of these will be referred to as device 1 as shown in FIG. 6A. The device 1 is placed within the delivery sheath 40. Because the device is flexible, it can be compacted to a relatively small shape. After being placed in the delivery sheath 40, the push plunger 41 is used to force the device 1 through the delivery sheath 40. The end 42 of the delivery sheath 40 is preferably first placed within an opening of a vessel. After being placed in that opening the push plunger 41 is used to force the first segment 2 of the device 1 out of the delivery sheath 40 as shown in FIG. 6B. Thereafter, the end 42 of the device is withdrawn from the opening, of the first vessel and placed in the vicinity of an opening of a second vessel. At this point, the plunger 41 is forced forward until the second segment 3 of the device 1 is extruded from the delivery sheath 40. The surgeon may ease the insertion by manipulating the vessels and the device 1 for optimum placement. At this point, the device 1 is in place interconnecting two vessels (See FIG. 2).

Figure 7A:
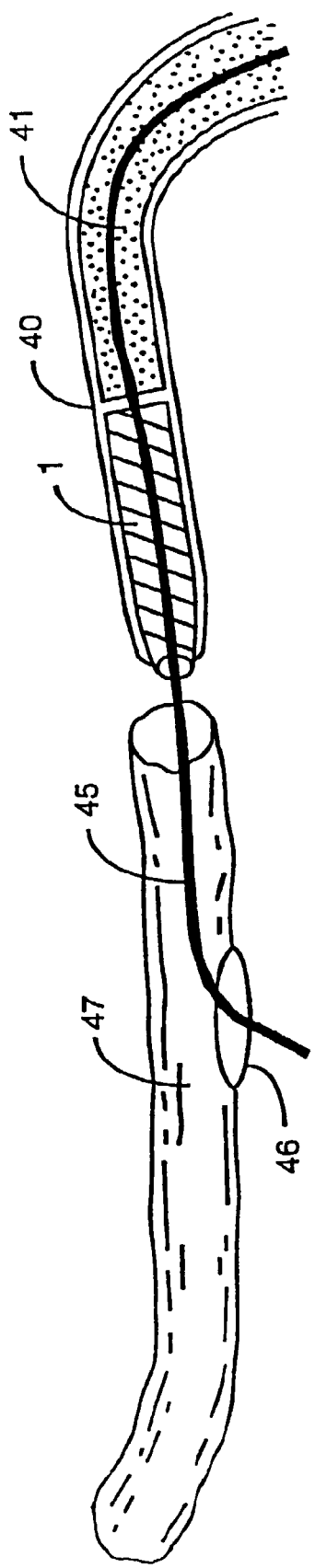
FIG. 7 includes FIGS. 7A, 7B, 7C, 7D and 7E each of which show a step of putting a side-to-side embodiment of the invention in place using a catheter and guide wire with FIG. 7A showing the device within the catheter and a guide wire in place, FIG. 7B showing the device moved toward the opening in the vessel guided by the guide wire, FIG. 7C showing the device partially inserted, FIG. 7D showing the device completely inserted into two vessels thereby interconnecting those vessels and FIG. 7E showing the catheter withdrawn.
Figure 7B:
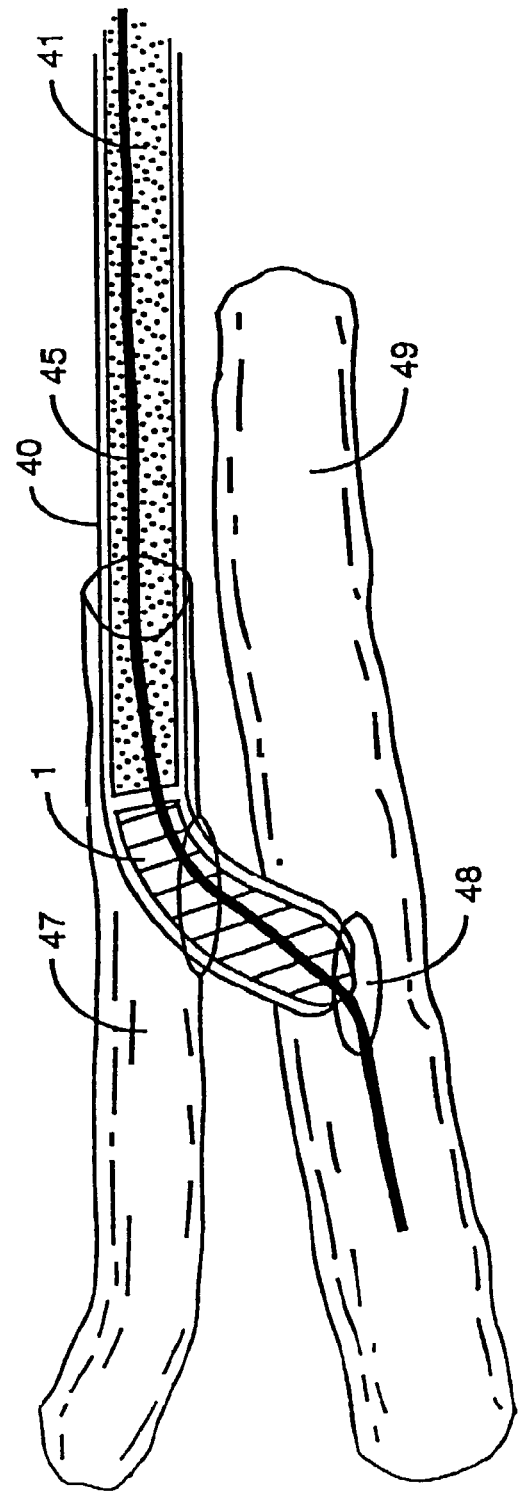
Figure 7C:
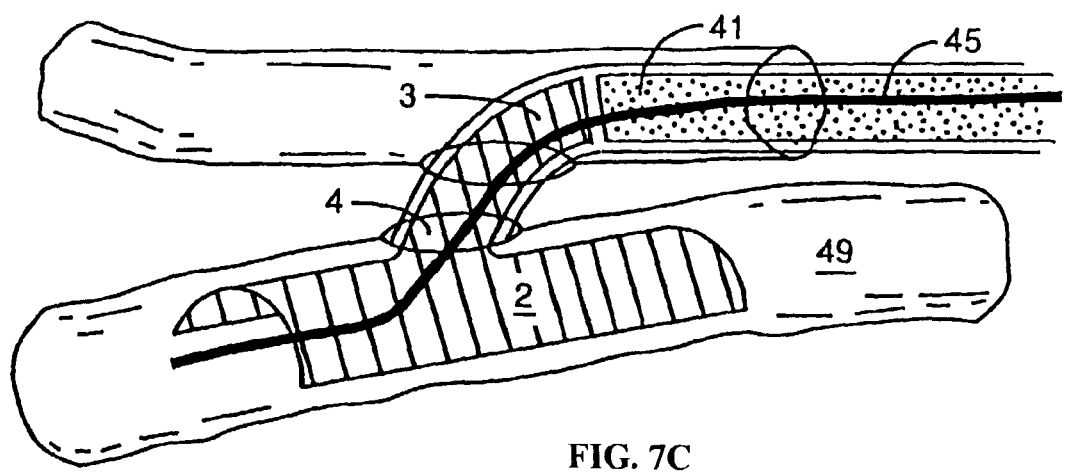
Figure 7D:
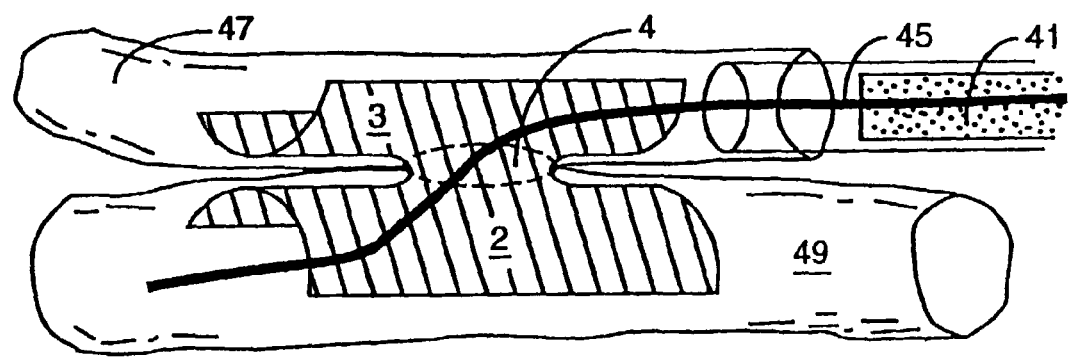

For a less invasive approach, a catheter and a guide wire delivery system can be used as is shown in FIGS. 7A-E. Device 1 is delivered by the catheter through the graft vessel 47. In this embodiment, the device 1 is placed within the delivery sheath 40 in a manner such that guide wire 45 is led through the opening 4 (see FIG. 1) of the device. The guide wire 45 is then inserted within an opening 46 of a graft vessel 47. At this point, the push plunger 41 is used to force the device 1 forward toward the opening 46 as is shown in FIG. 7B. The guide wire then leads the catheter into an opening 48 of a native vessel 49 as shown in FIG. 7B. The device 1 as shown in FIG. 7B is now in position for insertion into the opening 48 of the native vessel 49. The push plunger 41 is then moved forward as shown in FIG. 7C. This causes the first segment 2 of the device 1 to be inserted into the opening 48 of the native vessel 49. Upon being inserted into opening 48, the first segment 2 expands into its original shape. When this is completed, the delivery sheath 40 is positioned relative to the opening 46 of the graft vessel 47 and the push plunger 41 is moved forward to force the second segment 3 of the device 1 out of the delivery sheath 40. The second segment 3 also expands into its original shape upon being forced out of the delivery sheath 40. When this is accomplished the result is shown in FIG. 7D. At this point the device 1 is completely inserted and the vessels 47 and 49 are interconnected by the opening 4 of the device 1. Thereafter the delivery sheath 40, push plunger 41 and guide wire 45 may be withdrawn completely from the patient.

One aspect of the invention is a device such as the device 1 of FIG. 1 or device 33 of FIG. 5 loaded into a catheter delivery system of the type shown in FIGS. 7A-7E. The device 1 is loaded into the delivery sheath 40 so that the guide wire 45 goes through the opening 4. The combination of the device 1 and delivery sheath 40 can be conveniently sold as a unit for performing an anastomosis. Such a combination product provides the surgeon with a device properly matched in size with an insertion catheter.

Figure 8A:
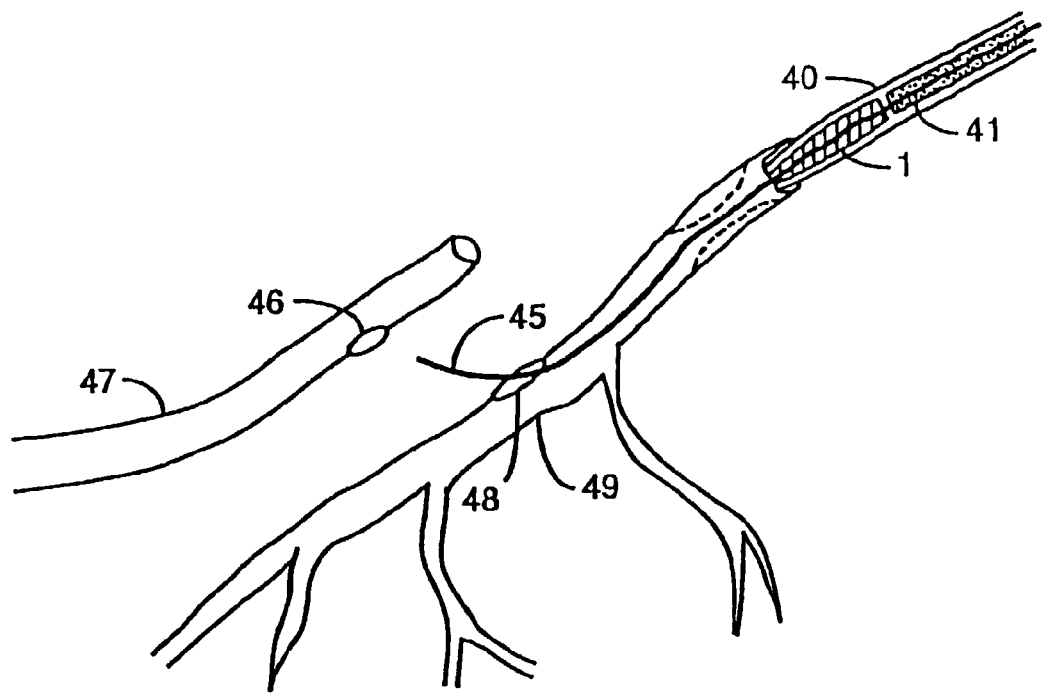
FIG. 8 includes FIGS. 8A, 8B and 8C which show three steps of a device of the type shown in FIG. 1 being inserted into and interconnecting two vessels with FIG. 8A showing the device in the catheter, FIG. 8B showing a guide wire inserted in the vessel opening and FIG. 8C showing the device in place.
Figure 8B:
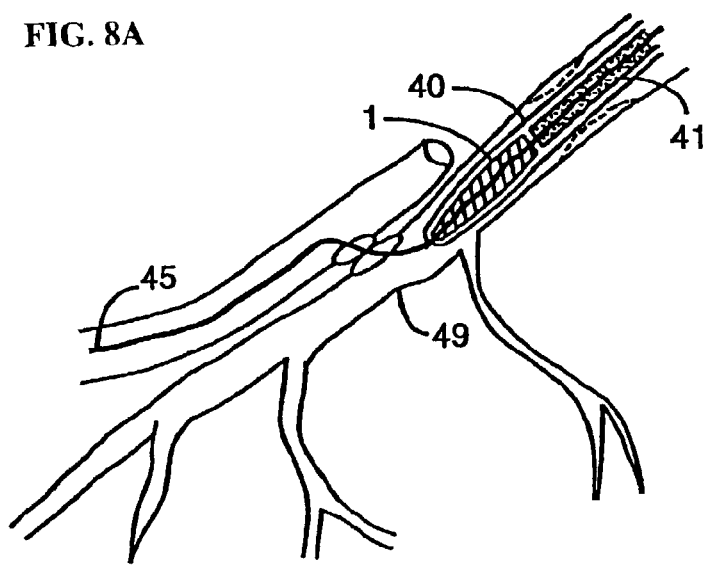
Figure 8C:
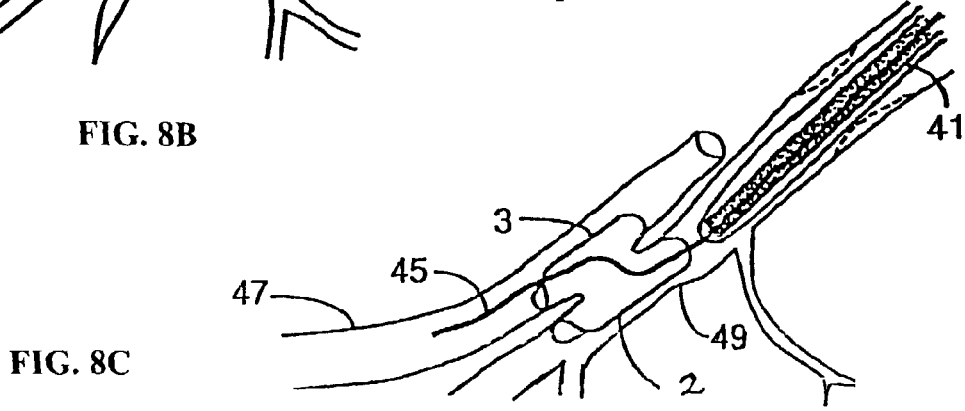

Another embodiment of the catheter insertion procedure is shown in FIGS. 8A, 8B and 8C. In this embodiment the device I is delivered using a catheter through the native vessel 49. Specifically, the delivery sheath 40 has the device 1 loaded within it. The device 1 is loaded into the delivery sheath 40 in a manner such that the guide wire 45 goes through the opening 4 of the device 1. Further, the push plunger 41 is positioned within the delivery sheath 40. The end of the delivery sheath 40 is placed within the native vessel 49 and the guide wire 45 is moved through the native vessel 49 and out of the opening 48 of the native vessel 49 as shown within FIG. 8A. Thereafter, the catheter is moved forward and the guide wire 45 is moved into the opening 46 of the graft vessel 47 (see FIG. 8B). Thereafter, the push plunger 41 is moved forward so that the device 1 forced out of the catheter 40. The first segment 3 of the device 1 enters the opening 46 of the graft vessel 47 and the second segment 2 of the device 1 remains within the native vessel 49 (see FIG. 8C).

After insertion and completion of the anastomosis the free end of the vessel 47 is tied off in a manner as shown within FIG. 2. It may be necessary to further expand the device by the use of a balloon catheter not very differently than a post dilatation of an angioplasty stent. This may help fully expand the device and enhance the sealing and connecting properties of the device. It may also be necessary to utilize stay sutures to stabilize the graft near the heart. These sutures are placed through fat or tissue surrounding the vessel in order to provide additional stability to the anastomosis. This is normally done when grafting the internal mammary artery to the coronaries but may be necessary in some cases using this device in order to prevent the vessels 49 and 47 from being inadvertently separated from each other.

FIGS. 39A-39E show another manner in which the subject devices may be delivered to join vessels together. In this embodiment, a direct access approach is employed to deliver and deploy a subject anastomotic connector device. As described above, a direct access approach may be used in a variety of applications, one such application being the formation of an AV fistula. In further describing this method, the formation of an AV fistula using device 1 of FIG. 1 will be used by way of example and is in no way intended to limit the scope of the invention as it will be apparent that this method may be employed in a variety of applications using any subject device.

Figure 39A:
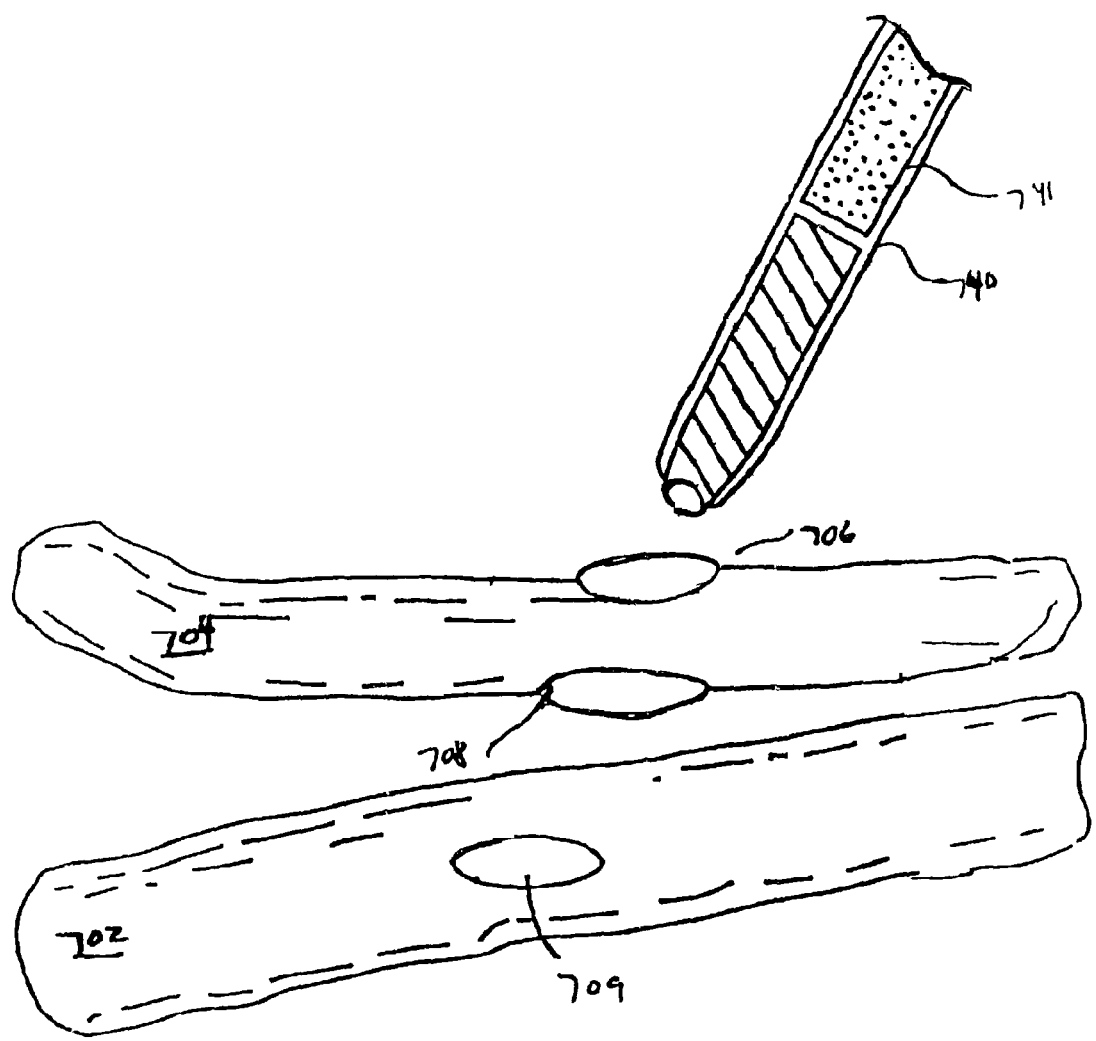
FIG. 39 includes FIGS. 39A-39E which show a step of delivering and deploying a subject device using a direct access approach and closing and sealing the access area with a subject closure device.

Accordingly, FIG. 39A shows the two vessels to be connected, 704 and 702, where one vessel is an artery and another is a vein. To begin the procedure, openings or slits of an appropriate shape and size, e.g., cross-shaped or the like, are created in each vessel using any convenient technique such as, micro incision, arteriotomy/veinotomy, needle puncture, etc, where one of the vessels, herein described with respect to vessel 704, has two openings provided therein. As shown, vessel 702 has opening 709 and vessel 704 has openings 706 and 708. Opening 706, provides access to the vessels for the purpose of providing an anastomotic connection therebetween and may also serve to provide an access graft or the like anastomosed thereto, as will be further described below. Opening 706 may be positioned through a substantially opposing vessel wall with respect to opening 708 or may be positioned in any appropriate area of the vessel, where opening 706 may be positioned in direct alignment with opening 708, i.e., directly above opening 708 such as positioned normal to opening 708, may be positioned opposite opening 708, but offset to one side thereof such that opening 706 is positioned non-normally or at an angle relative to opening 708, etc.

Prior to or after the openings have been provided, device 1 is loaded into sheath 740. A push plunger 741 is positioned within sheath 740, proximal to device 1. Device 1 is typically optimally folded or bent from an original configuration, as described above, and constrained in this folded configuration by sheath 740 so as to deploy within a target vessel in an optimum manner.

Figure 39B:
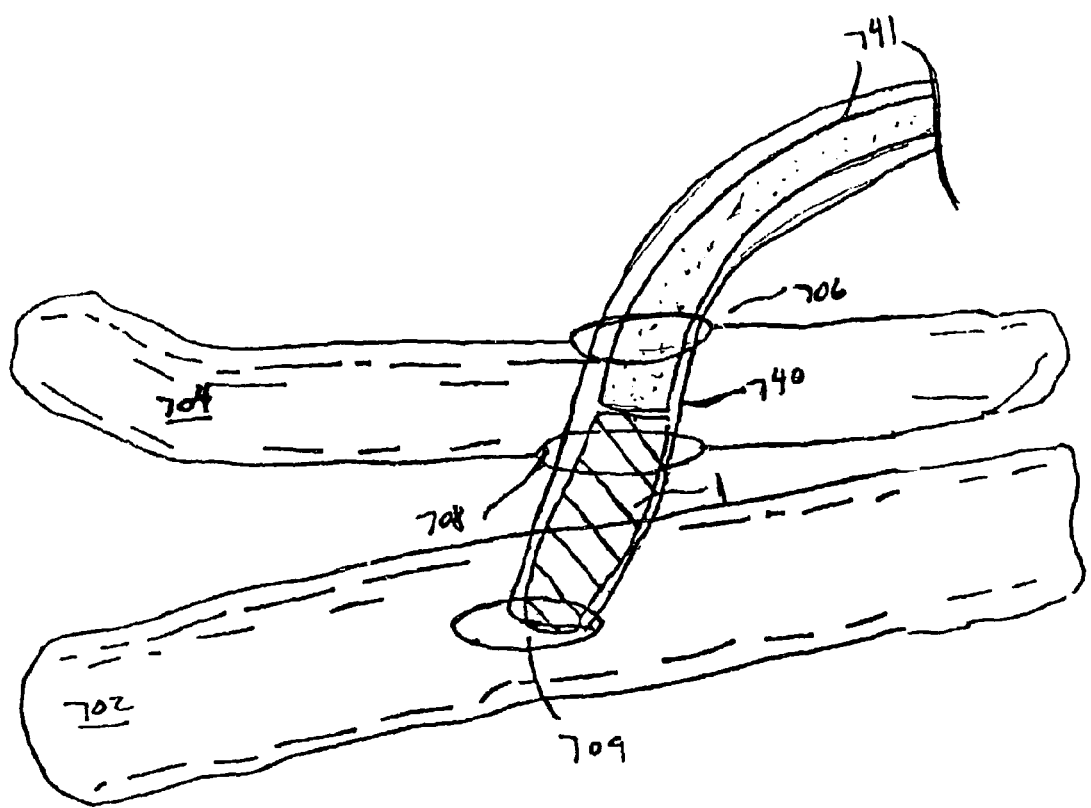

Device 1 is then delivered through the sheath to the vessels in the following manner. Sheath 740 is inserted within opening 706 of vessel 704. The sheath may be inserted such that it is positioned normal to or at an angle with opening 706 (or openings 708 and/or 709 described below). A guide wire may be employed such that the guide wire is inserted through openings 706, 708 and into opening 709 over which sheath is delivered. The guide wire may be retained in the vessels through the procedure, or may be removed after positioning of the sheath. As shown in FIG. 39B, sheath 740 having device 1 therein is further inserted through opening 708 and into or directly adjacent opening 709 of vessel 702 such that the distal tip of the sheath is positioned inside or adjacent vessel 702. At this point, the push plunger 741 is used to force the device 1 forward in sheath 740 towards the distal end thereof, as shown in FIG. 39B. The device 1 as shown in FIG. 39B is now in position for insertion into the opening 709 of vessel 702.

Figure 34B:
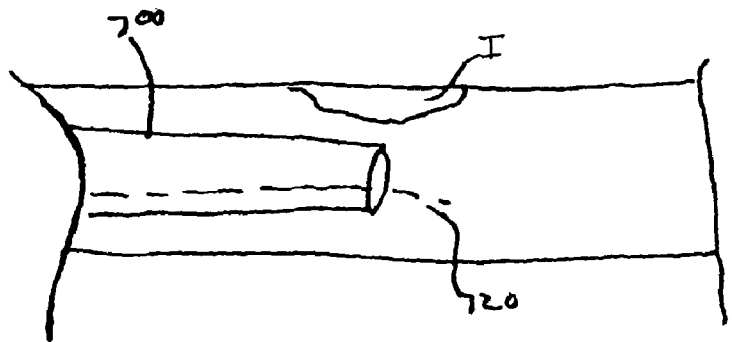
Figure 39C:
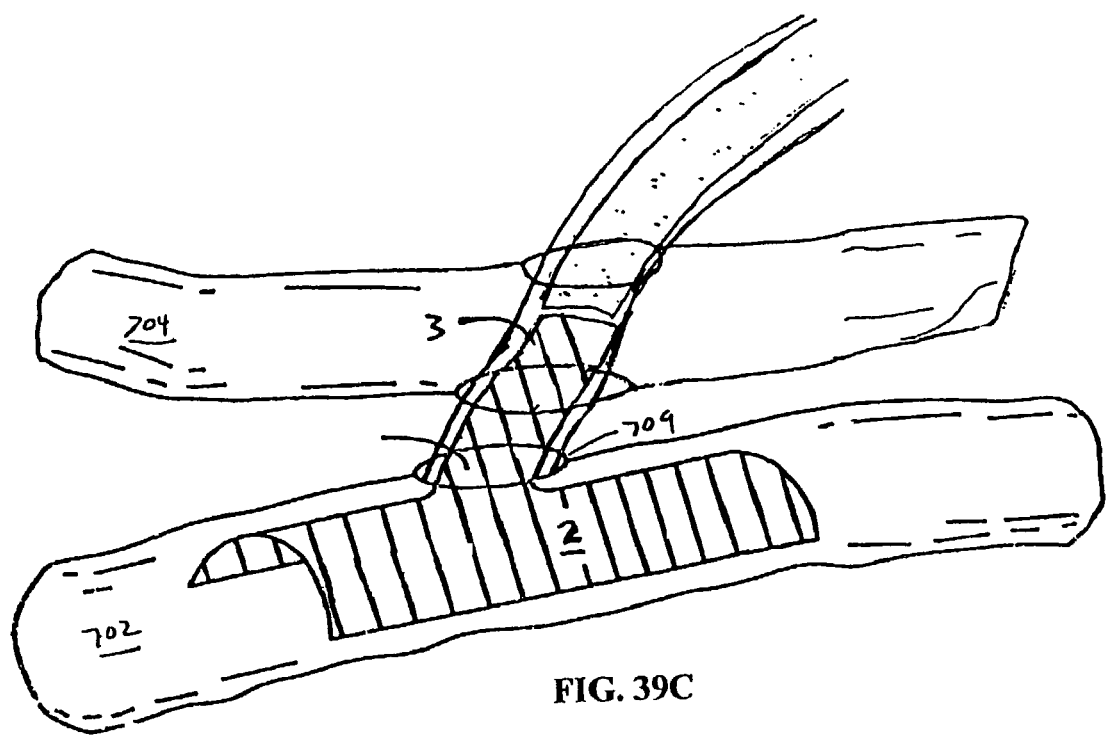
Figure 39D:
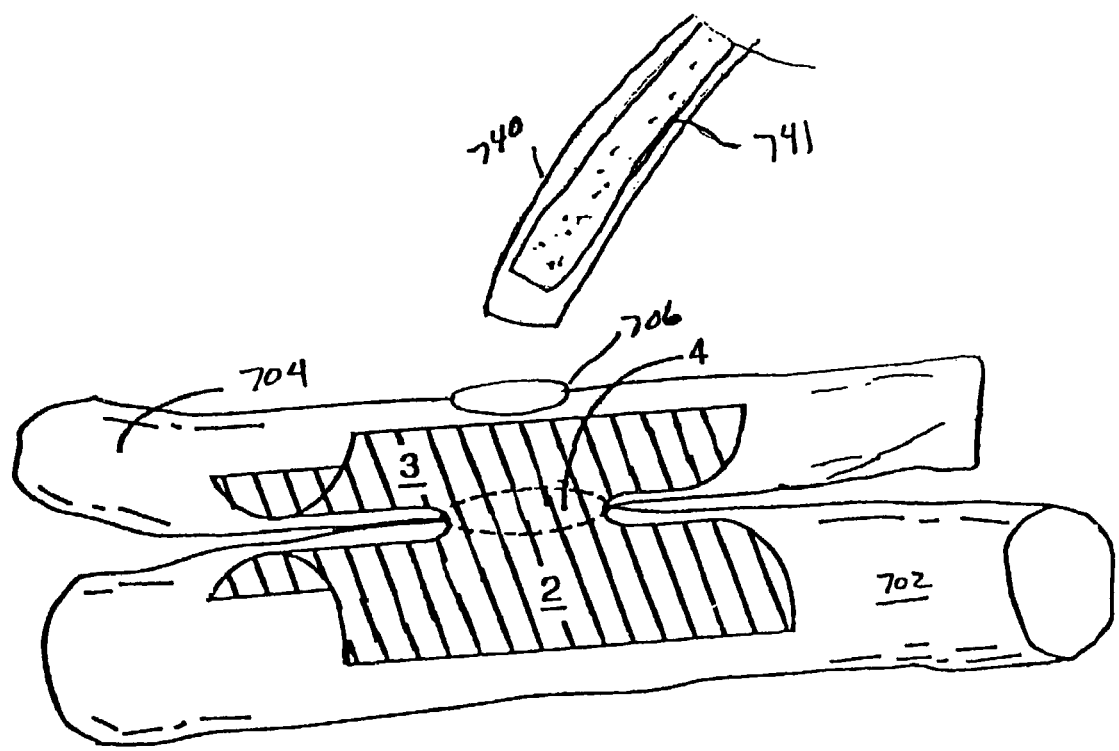
Figure 39E:
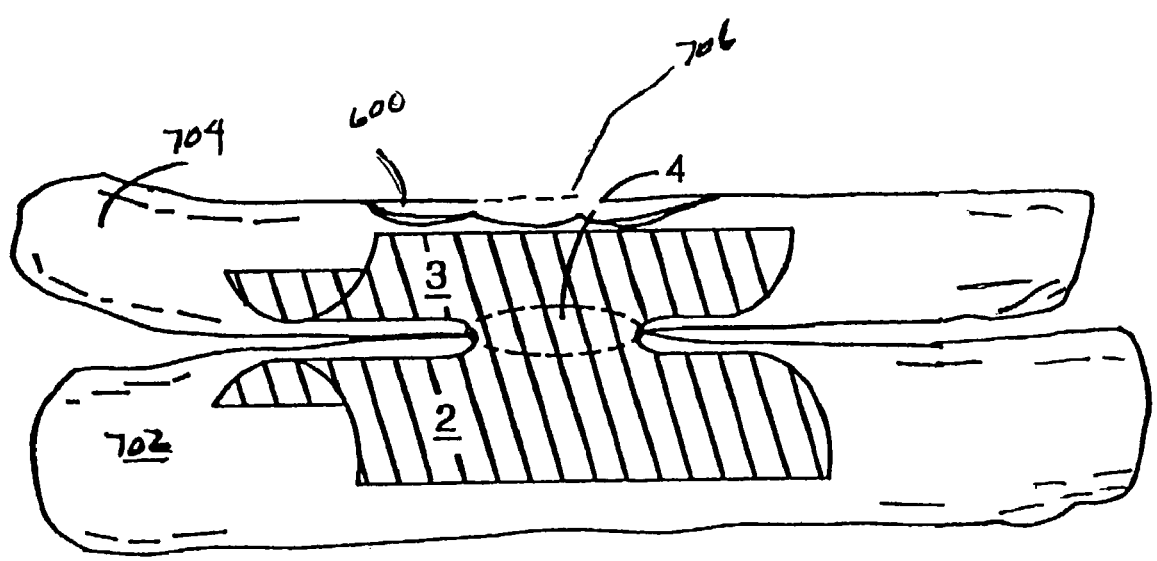

The push plunger 741 is then moved forward or distally as shown in FIG. 39C and/or the distal end of the sheath is retracted a distance proximally to expose the device. This causes the first segment 2 of the device 1 to be inserted into the opening 709 of vessel 702. Upon being inserted into opening 709, the first segment 2 expands into its original shape. When this is completed, the delivery sheath 740 is positioned relative to the opening 708 of vessel 704 and the push plunger 741 is moved forward or distally, and/or the distal end of the sheath is retracted a distance proximally to expose the device, to force the second segment 3 of the device 1 out of the delivery sheath 740. The second segment 3 also expands into its original shape upon being forced out of the delivery sheath 740. When this is accomplished, the result is shown in FIG. 34D. At this point the device 1 is completely inserted and vessels 704 and 702 are interconnected by the opening 4 of device 1. Thereafter the delivery sheath 740, push plunger 741, and the guide wire if used, may be withdrawn completely from the patient, or, in certain instances, may be left in place to deliver a closure and sealing device to close and seal opening 706, or to deliver and deploy a side-to-side anastomotic device to join an access graft thereto, for example a hemodialysis access graft, where the sheath, push plunger and guide wire are thereafter removed.

Figure 7E:
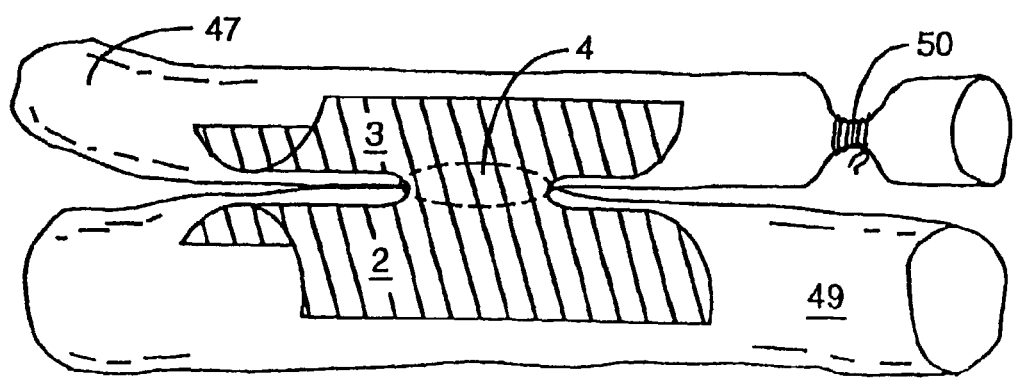

In the case where opening 706 is closed and sealed, such may be accomplished using any convenient closure device and method, e.g., sutures, bioglue, clip, or any other closure device. In many embodiments, opening 706 is sealed and closed using a subject closure and sealing device, as described above, where exemplary methods for closing and sealing an opening using the subject devices are described in detail below. FIG. 7E shows vessels 704 and 702 joined together with device 1 and opening 706 closed and sealed with closure device 600 of FIG. 38.

As mentioned above, in certain embodiments opening 706 is not immediately closed, but rather is used to connect an access conduit to vessel 704, i.e., an end-to-side anastomosis, for example for the purposes of providing access to the vessel for hemodialysis or the like, where any of the subject end-to-side devices may be used in this regard. This end-to-side anastomosis may be accomplished using any end-to-side method described herein.

In certain embodiments, it may be desirable to employ a means for holding together the two vessels to be anastomosed during practice of the subject methods. A suitable holding means, i.e., proximator, appositioner, vessel stabilizer, etc., will comprise a means for holding the donor and graft vessels, e.g., the coronary artery and the IMA, together in a sufficiently close relationship, e.g., in adjacent relationship, so that the device can join the vessels as described above.

Stopped Heart/Beating Heart

The device of the present invention can be used to interconnect vessels or more specifically complete an anastomosis while the patient's heart is beating or after the patient's heart has been stopped. Beating heart procedures can be carried out by making a variety of different types of initial incisions which could include a sternotomy where the patient's sternum is bisected or by making smaller incisions and utilizing minimally invasive surgical devices and methods (see Benetti, F. in U.S. Pat. No. 5,888,247). After the necessary incisions are made, the heart is stabilized using a stabilizer device. Thereafter the device of the invention is inserted by one or more different means described herein. Specifically, the first segment of a flexible device is inserted by bending the device and moving it into an opening in a first vessel. After bending the device and inserting it within the vessel it is released and the first segment of the device resumes its original configuration where the device conforms to an inner intravascular surface of the first vessel. The first segment of the device includes an opening and is connected to a second segment of the device along the periphery of that opening. The second segment of the device is then bent and moved into an opening of a second vessel. Thereafter the device is released and it resumes its original configuration and conforms to the interior wall of the second vessel.

The device can also be used in a stopped heart situation. Many of the different types of initial incisions mentioned above or others can be used to access the patient's chest cavity. A suitable graft vessel is harvested from the patient. Thereafter the patient's heart is stopped using a suitable cardioplegia. Thereafter, the steps referred to above with respect to insertion of the device are carried out. Although the present invention can be used in connection with a stopped heart procedure one of the advantages of the present invention is the ease of manipulation of the device in order to carry out an anastomosis. Because of the simple efficient manner in which the device of the invention can be manipulated and inserted it can generally be carried out while the patient's heart is beating.

Robotic Assist Intervention

The device can be used when robotic assist devices are utilized by the surgical staff. Robotic assist device surgery is typically performed by the surgeon through the use of robotic arms. The use of the robotic arms scales the motion of the surgeon and filters out unwanted tremors. This allows the surgeons to perform the surgery through smaller incisions and in more constricted spaces. Examples of such systems are the ones marketed by Intuitive Surgical Systems as described in U.S. Pat. No. 5,855,583.

Surgical Access and Visualization

The device and the catheter delivery systems can be used during hybrid procedures where surgical procedures are combined with interventional cardiology techniques. Such procedures use fluoroscopy to visualize and position the catheter delivery systems. The catheter is normally placed through femoral or radial access. Direct surgical access to the heart is typically achieved via small incisions in the chest or abdomen. A single or multiple trocar ports or a minimally invasive small retractor is placed in these incisions. An endoscope may be used to aid in visualization and/or deliver the catheter when employed to deliver the device.

The device can also be used in complete percutaneous procedures where no direct access to the heart is available to the physicians.

Stabilizing Device Implantation

Each embodiment of the invention is designed in a manner such that it does not require additional devices, sutures, staples or other materials to hold the device in place. Preferably, the first (and second) segment(s) of the device are joined and configured in a manner such that once the device is in place the segments will apply sufficient force against the interior walls of the vessel to securely hold the device in place aided by the action of intraluminal pressure. After the device has been held in place for significant periods of time, the vessels will naturally develop a new intimal layer and fuse through normal wound healing. At this point the device may no longer be needed and could, if so designed, begin dissolving.

In certain embodiments and certain situations it may be desirable to add additional means of holding the device in place. One addition holding means of interest includes biocompatible glues and adhesives. The glue could be applied after the device is implanted or placed on the device prior to implantation. Any biocompatible glue could also include other drugs such as growth factors that would aid in causing the vessels to grow together in the desired manner. Another means of interest is an annular or ring connector that can move from a first expanded to a second constricted position, such as those described in U.S. Pat. No. 6,056,762; the disclosure of which is herein incorporated by reference.

Tissue Closure Methods

As indicated above, the devices and methods of the subject invention are employed to close and seal an opening in tissue such as an opening in a wall of a conduit, where the subject methods are particularly suited for closing and sealing openings in tissue such as walls of bodily conduits and septums of the heart and are particularly suited for use in closing and sealing openings in walls of vascular vessels. Any type of vascular vessel may be closed and sealed according to the subject invention, where representative types of vascular vessels that may be closed and sealed according to the subject invention include, but are not limited to, coronary vessels, peripheral vessels, neurovascular vessels, etc. However, it will be apparent that the subject invention may be used to close and seal an opening in any appropriate type of tissue such as any bodily lumen, duct or other tubular organ present within a human or animal being. In certain embodiments, the subject closure devices are used to treat abnormal openings, holes or shunts occurring between the chambers of the heart or the great vessels (interatrial and interventricular septal defects or patent ductus arteriosus and aorthico-pulmonary window, respectively, which abnormalities may be created either congenitally or by acquisition, causing shunting of blood through the opening resulting in significant sequelae. As such, the subject devices and methods can be used in a variety of applications that require an opening within a luminal or tissue wall to be closed.

The closure device of the invention in any of its embodiments may be implanted without the use of special surgical tools. Specifically, the device may be inserted manually (i.e., using the surgeon's fingers alone) through an opening in a conduit or in combination with other surgical equipment normally used when operating on a patient. The subject methods may be performed intravascularly or extravascularly, i.e., an intravascular or extravascular approach may be employed with the subject devices. In intravascular methods, the device is delivered through a vessel or the vasculature to the site of the opening in the target vessel desired to be closed, where any convenient delivery means may be employed, including the delivery sheaths and devices described above. For extravascular protocols, the device is introduced from outside of the vessel to the site of the opening in the target vessel wall to be closed and is then inserted through the opening to be closed. In certain embodiments, a closure device may be delivered to an opening in a vessel over a guide wire. Delivery devices suitable for delivery of the subject closure devices are further described in copending U.S. patent application Ser. No. 10/235,944, entitled "Devices and Methods for Interconnecting Body Conduits", to Kupiecki, et al., filed on even date herewith; and copending U.S. patent application Ser. No. 10/236,060, entitled "Anastomosis Delivery Device Systems", to Barry, et al., filed on even date herewith; and in copending U.S. patent application Ser. No. 10/162,122, entitled "Devices and Methods for Interconnecting Vessels", filed on Jun. 3, 2002, which are herein incorporated by reference.

The present invention provides for the following general steps for an approach to closing an opening in a vessel wall and closing the opening with a closure device of the subject invention. However, as described above, the subject invention may be employed to close any type of bodily opening in a tissue in need of closure such as, e.g., septal openings. First, the segment is bent, folded or otherwise constricted to a reduced size and then inserted into the opening desired to be closed such that it is placed within the vessel walls. When released, the segment expands to at least a less constricted configuration and conforms to an inner surface or circumference of the vessel, operatively positioned over the opening to be closed. The surgeon may optionally further secure the closure device to the vessel by applying an adhesive between a surface of the device and a surface of the vessel. In any case, the closure device is inserted through the opening in the vessel wall and allowed to deploy in a manner that produces a sealing contact between the upper surface (i.e., the second or contact surface) of the device and the inner wall of the vessel (see for example FIGS. 17, 28 and 32) such that there is a sealing contact about the entire circumference or perimeter of the opening, thereby closing the opening and preventing the escape of substances from within the vessel through the opening. The above steps result in the establishment of a substantially fluid-tight seal over the opening that is sustained by the conformation of the device to the internal vessel wall and the intravascular pressure.

In certain embodiments, for example where the closure device creates contact amongst opposing edges of the vessel opening, tissue bonding may occur and result in a permanent and natural closure/seal at the opening over time, where such tissue bonding may be facilitated by one or more agents, components, and the like, that are seeded, coated, layered or embedded on or in a subject device.

Furthermore, in those devices having one or more thrombogenic substances associated therewith, thrombosis at the opening may occur and result in a permanent and natural closure/seal at the opening.

As indicated above, any suitable delivery protocol may be employed. In certain embodiments, it may be desirable to provide the closure device of the invention over a guide wire or using a surgical dispenser or the like through which the device is moved and inserted. FIGS. 33A through 33D illustrate a simple representation of how the closure devices of the subject invention may be inserted into a vessel over a guide wire. FIGS. 34A through 34D illustrate a simple representation of the closure devices of the subject invention may be used inserted into a vessel to patch and seal an irregularity on a surface of a conduit wall. FIGS. 35A, 35B and 35C illustrate a simple representation of how the closure devices of the subject invention may be inserted into a vessel using a surgical dispenser having direct access to an opening in a vessel. Both of these approaches will now be described in greater detail.

As mentioned above, a subject closure device may be delivered over a guide wire to a position within a vessel or to a position with the heart, i.e., intracardially, to close an opening in the vessel or septal wall, respectively. In further describing the subject methods, reference to closing an opening in a vessel will be used for exemplary purposes and in no way is intended to limit the scope of the invention as it will be apparent that openings in other tissue structures such as intracardiac openings, e.g., septal defects, may be closed and sealed using the subject methods. Furthermore, device 460 of FIG. 30 will be used to describe an over-the-wire delivery approach for vessel closure using a subject closure device for exemplary purposes and is in no way intended to limit the scope of the invention as any subject closure device having an aperture or area that can accommodate a guide wire may be delivered according to the subject methods.

Figure 33A:
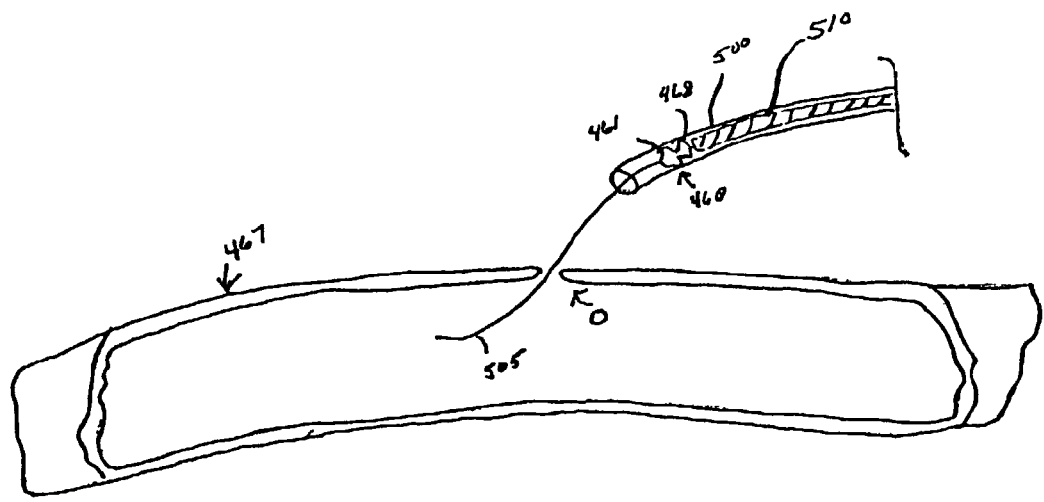
FIG. 33 includes FIGS. 33A-33D each of which show a step of deploying a subject closure device over a guide wire and into an opening in a vessel wall to be closed and closing that opening with the device.
Figure 33B:
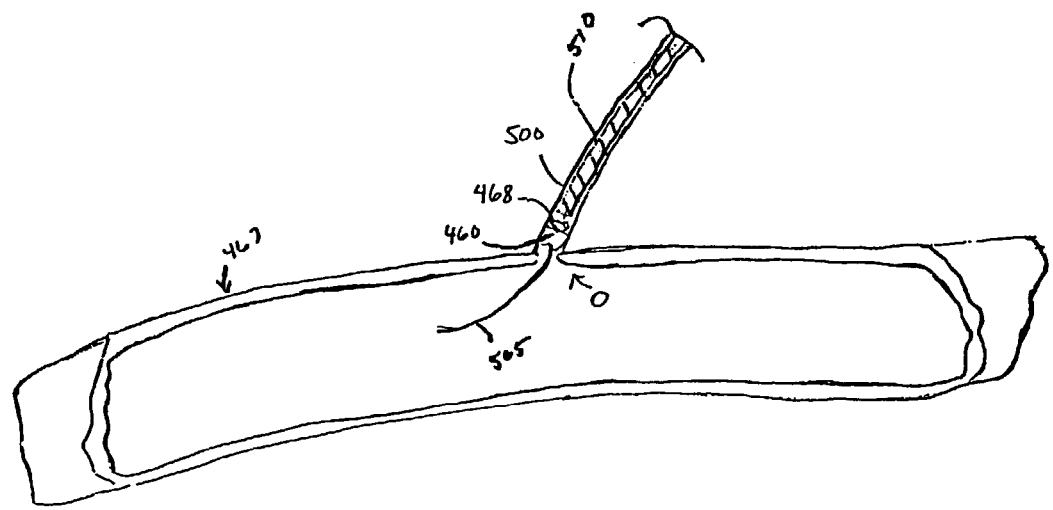
Figure 33C:
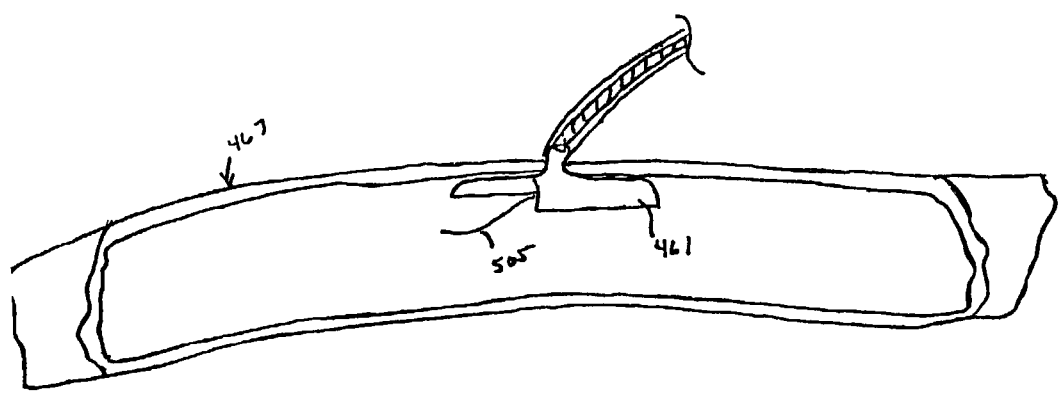
Figure 33D:
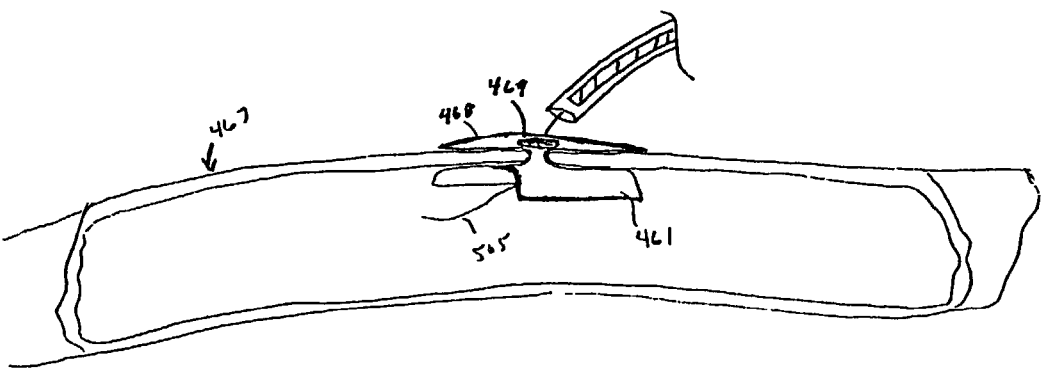

Referring to FIGS. 33A-33D, steps are illustrated for delivering and deploying a subject closure device 460 within a vessel 497 through an opening O over a guide wire 505, where the guide wire may have been positioned through opening O during an intravascular procedure that is completed and which used opening O as an intravascular access site. Device 460 is positioned within a delivery sheath 500, typically device 460 having segment 461 and transition portions 468 is folded or bent into a low profile configuration inside sheath 500 and usually is bend into a configuration that facilities the optimal unfolding of the device inside the vessel, over the opening in an appropriate manner. At this point, delivery sheath 500, with closure device 460 therein, is moved closer to opening O, as shown in FIG. 33B, until sheath 500 is caused to contact vessel 497 such that the opening of sheath 500 is aligned with opening O. Alternatively, sheath 500 may be moved a distance into the vessel through the opening. Once the sheath is appropriately positioned with respect to the vessel, the guide wire may be removed, or may be left in place. Push plunger 510 is used to force closure device 460 forward or distally toward opening O as is shown in FIG. 34B. Closure device 460 as shown in FIG. 33B is now in position for insertion through opening O of the vessel. Push plunger 510 is then moved forward distally as shown in FIG. 33C. This causes segment 461 of device 460 to be inserted into vessel 497, through opening O, and aligned over the opening. Upon being inserted through opening O, segment 461 expands into a less constricted configuration or shape such that it is operatively deployed in the vessel to close and seal the opening. Alternatively, the distal tip of the sheath 500 may be moved into the interior of vessel 497 such that segment 461 is positioned in alignment with opening O and sheath may be retracted a distance proximally to expose and deploy segment 461 within the vessel, over opening O. When this is completed, delivery sheath 500 is again moved a distance proximally to expose and deploy transition portion 468, where push plunger 510 may be used to urge transition portions 468 of device 460 out of delivery sheath 500. Transition flaps 468 expand into their original shape upon being forced out of the delivery sheath and conform to the exterior wall of vessel V to provide a smooth transition between the device and the exterior vessel wall without puncturing or compressing the wall. When this is accomplished, the result is as shown in FIG. 33D where the device is shown deployed in the vessel over the opening. It is important to note that a one-way or hemostatic valve 469, or any other suitable material, element or composition, prevents fluid flow from the interior of the vessel through sheath 500. Thereafter delivery sheath 500, push plunger 510 and guide wire 505 may be withdrawn completely from the patient. Thrombosis may be promoted at the opening to provide a natural and permanent closure and seal at opening O and/or in those embodiments having a self-sealing, thin membrane cover, the opening in the membrane cover is closed after the guide wire is removed to prevent fluid flow from the interior of the vessel out through the opening made by the guide wire.

As mentioned above, the subject methods also include patching and sealing irregularities present on an internal surface of a conduit such as a vessel. Such irregularities may be pathologic conditions or results of procedures and include dissections, protrusions, adhesions, for example formed during or after surgery, micro or macro lesions such as plaque, and the like. These irregularities may result in undesirable consequences that include turbulence within the conduit which can lead to formation of thrombus, stenosis and possible occlusion of the conduit, reduced conduit cross-sectional area which may adversely compromise flow, etc. Accordingly, sealing the irregularities using the subject devices provides a patch over the irregularities and also provides a smooth surface and improved flow through the conduit.

FIGS. 34A-34D illustrate steps involved in the subject methods for delivering and deploying a subject device using an over-the-wire approach for patching and sealing an irregularity on a surface of a conduit wall. In illustrating the subject methods, a device analogous to device 600 of FIG. 37 is used for exemplary purposes only and is no way intended to limit the scope of the invention as any embodiment of the subject closure devices may be used to patch and seal an irregularity on a conduit surface. Furthermore, a vessel is used as a representative conduit, where such is for exemplary purposes only and is no way intended to limit the scope of the invention.

Prior to delivering a subject device to the site of a vascular irregularity, access is made at the target vessel and a guide wire is positioned therein. Such target vessel access may be accomplished by a small incision, i.e., an arteriotomy, made in the target vessel or by the Seldinger technique as described above. FIG. 34A shows guide wire 720 positioned within a vessel 496 at the site of a vascular irregularity I.

Prior to introducing a subject patching and sealing device over the guide wire, a delivery device such as a catheter or any appropriate sheath 700 is advanced over the guide wire, as shown in FIG. 34B. At this point, sheath 700 may be advanced distally over the guide wire a distance such that the distal end of the sheath is positioned adjacent irregularity I, or the sheath may be so advanced after a subject device has been loaded therein.

Once the access site has been established, a guide wire 720 is operatively positioned at the site, and sheath 700 is advanced over the guide wire. Device 730 having segment 732 is now inserted into the proximal end of sheath 700 over guide wire 720 (if not already inserted done so), through an aperture in the device (not shown), such that the device assumes a constrained or folded state within the sheath for optimal expansion and unfolding over the irregularity. As described above, the aperture is capable of being sealed after removal of the guide wire therefrom, i.e., it is self-sealing. If not previously accomplished, the distal end of sheath 700 is advanced adjacent the site of the irregularity to be patched and sealed.

Figure 34C:
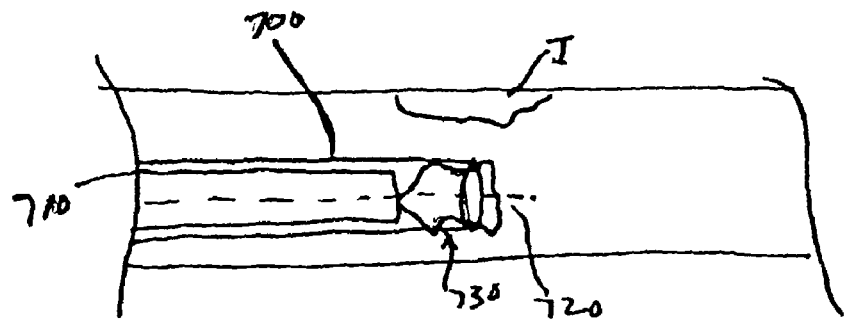
Figure 34D:
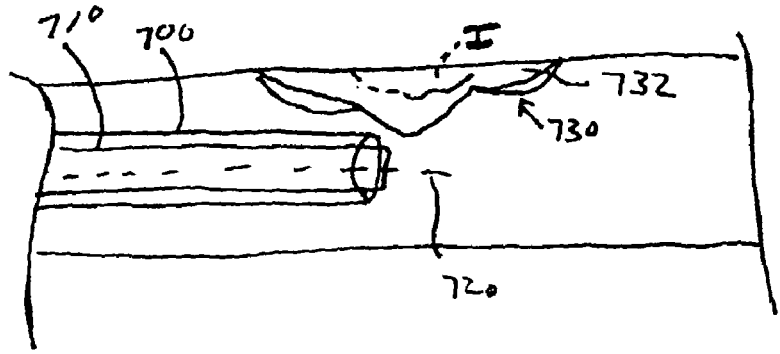

Next, device 730 is caused to exit the distal end of the sheath and deploy over the irregularity, as shown in FIGS. 34C and 34D. Accordingly, device 730 may be pushed out of sheath 700 using a pusher element 710 and/or alternatively sheath 700 may be proximally retracted a distance so as to expose device 730 to the interior of the vessel. In any case, once exited from the sheath, device 730 operatively deploys in the vessel over the irregularity.

As shown in FIG. 35D, once segment 732 is released from the confines of the sheath, it assumes a substantially unconstricted or unfolded configuration. Accordingly, segment 732 expands against the internal wall of vessel 496, over irregularity I, so as to provide a patch over the irregularity. The internal vessel pressure causes the segment to seal against the adjacent vessel wall surface, over the irregularity, providing a smooth vascular surface. In certain instances, it may be desirable to employ an adhesive or the like to facilitate the securement of the device over the irregularity. As mentioned above, once the guide wire is no longer disposed in the aperture of the device, the aperture closes, e.g., the material surrounding the aperture closes in or a valve prevents flow therethrough. Finally, sheath 700 is retrieved over guide wire 720 followed by retrieval of guide wire 720 from within the body.

The subject closure devices may also be inserted into a vessel using a surgical dispenser having direct access to an opening in a vessel. In describing this approach, the closure device shown in FIGS. 35A to 35C will be represented by device 370, which is analogous to the device shown in FIG. 16 for exemplary purposes only and is in no way intended to limit the scope of the invention as it is to be understood that any embodiment of the subject closure devices may be used with the subject methods.

To begin, device 370 is placed within delivery sheath 375. Due to the flexibility of device 370, it can be compacted, folded or bent to a relatively small size, as shown. After being placed in delivery sheath 375 and constrained in this folded configuration by the dimensions of sheath 375, push plunger 31 is used to force device 370 through delivery sheath 375, and ultimately through opening O in vessel 495, such that opening O is an opening in vessel 495 desired to be closed.

Accordingly, end 372 of delivery sheath 375 is either positioned adjacent or within opening O. After being appropriately positioned either adjacent or within opening O, push plunger 371 is used to force segment 373 of device 370 through delivery sheath 375 as shown in FIG. 35B. Upon further application of force to segment 373 by push plunger 371, device 370 is ultimately completely liberated from delivery sheath 375 as shown in FIG. 35C, such that it expands to form a sealing relationship with vessel 495 to close and seal opening O to provide a substantially fluid-tight seal around the opening.

Regardless of how the device is delivered to a site having an opening in a wall thereof which is in need of closure or patching and sealing, a feature of the subject methods is that additional devices, sutures, staples or other materials to hold the closure device in place within the vessel are not required. More specifically, the vessel closure devices are configured in a manner such that, once the closure device is in place operatively aligned with an opening to be closed or an irregularity to be patched and sealed, the segment of the closure device will be held securely in place with respect to the opening by the action of intraluminal pressure.

Vascular Access for Surgical Instrumentation

As mentioned above, the subject vascular closure devices may be used to close and seal any type of opening in a vessel or tissue, e.g., septal openings in need of closure. For example, in many surgical procedures, an opening is created in a vessel to provide an access point for the insertion of surgical instruments into the vessel for a variety of surgical procedures, where surgical procedures utilizing such access are well known in the art and include, but are not limited to procedures for both coronary and peripheral applications such as angiography, ultrasound imaging, angioplasty, atherectomy, embolic protection, stent placement, laser ablation, graft placement, femoro-popletial bypass, arteriovenous fistula formation, minimally invasive CABG, and the like., etc. Regardless of the reason for the opening, the subject closure devices are suitable for use in closing and sealing such openings to provide hemostasis at the site after the completion of the procedure.

Robotic Assist Intervention

The device can be used when robotic assist devices are utilized by the surgical staff. Robotic assist device surgery is typically performed by the surgeon through the use of robotic arms. The use of the robotic arms scales the motion of the surgeon and filters out unwanted tremors. This allows the surgeons to perform the surgery through smaller incisions and in more constricted spaces. Examples of such systems are the ones marketed by Intuitive Surgical Systems as described in U.S. Pat. No. 5,855,583.

Surgical Access and Visualization

The devices and the catheter delivery systems can be used during hybrid procedures where surgical procedures are combined with interventional cardiology techniques. Such procedures use fluoroscopy to visualize and position the catheter delivery systems. The catheter is normally placed through femoral or radial access. Direct surgical access to the heart is typically achieved via small incisions in the chest or abdomen. A single or multiple trocar ports or a minimally invasive small retractor is placed in these incisions. An endoscope may be used to aid in visualization and/or deliver the catheter when employed to deliver the device.

The device can also be used in complete percutaneous procedures where no direct access to the heart is available to the physicians.

Stabilizing Device Implantation

Each embodiment of the invention is designed in a manner such that it does not require additional devices, sutures, staples or other materials to hold the device in place. Preferably, the segment of the device is configured in a manner such that once the device is in place the segment will apply sufficient force against the interior walls of the vessel to securely hold the device in place aided by the action of intraluminal pressure. After the device has been held in place for significant periods of time, the vessels will naturally develop a new intimal layer around the opening that has been closed through normal wound healing. At this point the device may no longer be needed and could, if so designed, begin dissolving.

In certain embodiments and certain situations it may be desirable to add additional means of holding the device in place. One additional holding means of interest includes biocompatible glues and adhesives. The glue could be applied after the device is implanted or placed on the device prior to implantation. Any biocompatible glue could also include other drugs such as growth factors, mitogenic factors, etc., that would aid in causing the vessels to grow together in the desired manner. Another means of interest is an annular or ring connector that can move from a first expanded to a second constricted position, such as those described in U.S. Pat. No. 6,056,762; the disclosure of which is herein incorporated by reference.

Kits

Also provided are kits that at least include one device according to the subject invention, where in many embodiments the kits may include two or more devices having varying sizes so as to provide the surgeon or other health care practitioner the convenience and security of having a device with the correct size for a particular patient. The kits may further include other tools such as delivery devices, (e.g., a delivery catheter, loaded delivery device, etc.), proximator or sizing devices for determining the appropriate size of the device to be used, and the like, as described above, which devices find use in performing an anastomosis with the device present in the kit. The kit may comprise only one anastomotic device or closure device of the invention having a single-size segment(s) which may be readily usable for larger vessels but not for smaller ones. This kit may further include a stamping or cutting fixture and mechanism for trimming the segment to achieve an appropriate size so as to fit into a smaller vessel. Each of the tools of the present invention may also have more than one function. For example, both cutting and delivery functions may be included in a single tool increasing the ease of the procedure, eliminating the cost of another tool and reducing the procedure time. The subject kit may contain a device comprising a single size intravascular segment of sufficient size to be applicable to the largest vessels. The kit may comprise a stamping or cutting fixture and mechanism used to trim the size of the intravascular segment in an appropriate manner so as to be able to fit into smaller vessels.

The subject kits may also include securing or reinforcement means, e.g., biocompatible glues/adhesives, hemostatic rings, etc. In addition, the subject kits typically include instructions for using the devices in methods according to the subject invention. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way if illustration and not by way of limitation.

EXPERIMENTAL

Experimental Examples

An experiment was conducted to test the ease of insertion, sealing properties and retention ability of the segments/flanges of the anastomotic devices of the present invention. Various embodiments of the segments/flanges were implanted into a vessel of a swine weighing 39.2 kg. Vessel having diameters of 2, 3 and 4 mm were used as implant vessels due to their similarity in size to average human coronary arteries. Seven segments were used, all made of a silicone-urethane copolymer (Polymer Technology Group, Pursil 80A) and having a semi-ellipsoidal shape with short and long axis dimensions of 9 by 15 mm. The segments had varying thicknesses ranging from 100 to 380 microns ($100 \times 10^{-3}$ to $380 \times 10^{-3}$ mm). Prior to implant, a suture was secured to the center of each segment to aid in testing the stability and the ability of the segments to keep from dislodging from the arteriotomy. The swine was placed under general anesthesia and, once adequately sedated, a pressure line was placed in its left femoral artery in order to continuously monitor the swine's blood pressure. For each implant vessel, approximately 5 cm of the vessel's length was exposed and isolated. Conventional bulldog clamps were then placed on the exposed vessel, one on each side of the arteriotomy site, to occlude the vessel during implantation of the various devices. An arteriotomy was then cut in the exposed section of vessel between the bulldog clamps. Each of the seven segments was individually inserted into the artery between 10 and 20 minutes during which time observations were made and tests were conducted. No sutures or glues were used to augment the sealing or physical stability of the implanted segments. Blood pressure was manipulated pharmacologically (with Levophed) to create low and high-pressure environments as desired. Ease of insertion and observations for leakage from the arteriotomy site were recorded. A pull test was conducted on each segment by tugging on the centrally placed suture to determine the segments propensity for dislodgment from the vessel. The table below summarizes the results obtained from the experiment:

| | Segment Thickness | Min-Max Vessel size | Ease of BP | Sealing & Insertion | strength & Leakage | Pull Test (tug dislodgment |
|---|---|---|---|---|---|---|
| 1. | 380 microns ($380 \times 10^{-3}$ mm) | 3 mm | 70/12 to 250/110 | High | Good | Strong; no dislodgment |
| 2. | 100 microns ($100 \times 10^{-3}$ mm) | 3 mm | 64/12 to 230/109 | Moderate | Good | Easy; dislodged |
| 3 | 150 microns ($150 \times 10^{-3}$ mm) | 3 mm | 58/17 to 210/109 | High | Good | Fair; dislodged |
| 4. | 200 microns ($250 \times 10^{-3}$ mm) | 3 mm | 68/21 to 210/109 | High | Good | Very strong; minor leakage but no dislodgment |
| 5. | 250 microns ($250 \times 10^{-3}$ mm) | 3 mm | 58/18 to 220/110 | High | Excellent | Very strong; some leakage and slipping but no |

-continued

| Segment Thickness | Min-Max Vessel size | Ease of BP | Sealing & Insertion | strength & Leakage | Pull Test (tug dislodgment |
|---|---|---|---|---|---|
| 6. 300 microns (250 × 10⁻³ mm) | 4 mm | 59/20 to 198/110 | High | Excellent | Very strong; some leakage and slipping but no dislodgment |
| 7. 250 microns (250 × 10⁻³ mm) | 2 mm | 66/19 to 198/112 | High | Excellent | Very strong; no leaks or dislodgment |

Overall, the experiment showed that segments/flanges made of polyurethane polymer and having a thickness in the range from 100 to 380 microns (100×10⁻³ to 380×10⁻³ mm) produced a good arteriotomy seal under normal physiological conditions. The thinner segments provided good sealing function but were less physically stable once in-situ. A range of thicknesses for optimally handling and implanting the segments appeared to be in the range of 250 to 300 (250×10⁻³ to 300×10⁻³ mm) microns with a material having the physical properties utilized in this experiment.

It is evident from the above description and results that the subject invention provides important new anastomotic devices and procedures which overcome a number of disadvantages currently encountered in the field of anastomosis. The subject devices are easy to use and can provide for vessel joinder with out the use of sutures, staples, glues or other holding means. In addition, the subject devices are substantially atraumatic and provide for rapid healing. As such, the subject invention represents a significant contribution to the field.

The instant invention is shown and described herein in what is considered to be the most practical, and preferred embodiments. It is recognized, however, that departures may be made there from, which are within the scope of the invention, and that obvious modifications will occur to one skilled in the art upon reading this disclosure.

What is claimed is:

1. A device for connecting first and second tissue structures comprising:
   first and second substantially parallel and elongate flexible segments each having proximal and distal ends, wherein the first and second segments each comprise a compliant material configured to be constricted for implantation within the first and second tissue structures, respectively, and wherein the material has a natural tendency to return to an unconstricted state such that, when implanted in the tissue structures, the material utilizes an internal fluid pressure within the respective tissue structure to conform to a shape of an inner surface of the tissue structure to provide a sealing contact with the inner surface; and
   a flow opening extending between the first and second segments at a point along the elongate length of the segments at least a distance from each of the proximal and distal ends to fluidically couple the first and second tissue structures.

2. The device according to claim 1, wherein the first and second flexible segments are formed of a material that is one or more of biodegradable and bioresorbable.

3. The device according to claim 1, wherein the first and second flexible segments do not substantially compress, tension, or puncture the tissue structure when implanted therein.

4. The device according to claim 1, further comprises a thrombogenic substance.

5. The device according to claim 1, wherein at least a portion of the device is coated with a therapeutic substance.

6. The device according to claim 1, wherein the first tissue structure is one of a blood vessel and a portion of a heart.

7. The device according claim 1, wherein the first and second segments are configured to cooperatively provide a passive sealing force to the respective first and second tissue structures in which each are operationally disposed that pulls the first and second tissue structures together.

8. The device according to claim 1, further comprising:
   a separation thread disposed at least partially within the first flexible segment and configured to tear at least a portion of the first flexible segment in response to receiving a pulling force on the separation thread.

9. The device according to claim 1, wherein one or more of the first and second segments have a cylindrical shape.

10. The device according to claim 1, wherein the flow opening comprises an elongate member having a cylindrical shape.

11. The device according to claim 10, wherein the elongate member extends substantially perpendicularly between the first and second segments.

12. The device according to claim 10, wherein the elongate member extends between an aperture in the first segment to an aperture in the second segment, and wherein the apertures in the first and second segments are offset from one another.

13. The device according to claim 1, wherein at least the portions of the first and second segments adjacent the ends of the flow opening are positioned in substantially parallel planes.

14. The device according to claim 1, wherein the first and second segments have substantially the same size and shape.

15. The device according to claim 1, wherein the second segment has at least one of a different size and shape than the first segment.

16. The device according to claim 1, wherein the device comprises a unitary component.

17. The device according to claim 1, wherein the device comprises two or more connectable components.

18. A device for fluidically coupling an artificial opening in a first vascular tissue structure with a second tissue structure comprising:
   a first elongate flexible segment having a proximal and a distal end and comprising a compliant material configured to be constricted for implantation in the first tissue structure via the artificial opening, wherein the material has a natural tendency to return to an unconstricted state such that, when implanted in the tissue structure, the material utilizes an internal fluid pressure within the first tissue structure to conform to a shape of an inner surface of the first tissue structure to provide sealing contact with the inner surface of the first tissue structure around the artificial opening;

a second elongate flexible segment disposed substantially parallel to the first segment having a proximal and a distal end and implantable within the second tissue structure; and a flow opening extending through the artificial opening between the first and second segments at a point along the elongate length of the segments at least a distance from each of the proximal and distal ends of the first and second segments to fluidically couple the first and second tissue structures.

19. The device according to claim 18, wherein the first segment further comprises a non-tissue facing surface and a tissue-contacting surface configured to conformingly contact the inner surface of the first tissue structure.

20. The device according to claim 19, wherein the non tissue-facing surface is configured to receive and to transmit fluid pressure exerted thereon to the tissue contacting surface such that a substantially fluid tight contact between the tissue-contacting surface and the inner surface of the first tissue structure is formed.

21. The device according to claim 18, wherein the first segment comprises an elastomer.

22. The device according to claim 18, wherein the first segment comprises a biocompatible material.

23. The device according to claim 18, wherein the first segment comprises one of a biodegradable and a bioresorbable material.

24. The device according to claim 18, wherein the first segment comprises a polymer material.

25. The device according to claim 24, wherein said polymer is an elastomer.

26. The device according to claim 25, wherein said elastomer comprises polysiloxane or polyurethane.

27. The device according to claim 25, wherein said elastomer has a durometer ranging from about 80 Shore A to 55 Shore D.

28. The device according to claim 18, further comprising: a valve controlling flow through said aperture.

29. The device according to claim 18, wherein the first and second segments are configured to cooperatively provide a passive sealing force to the respective first and second tissue structures in which each are operationally disposed that pulls the first and second tissue structures together.

30. The device according to claim 18, further comprising: a separation thread disposed at least partially within the first flexible segment and configured to tear at least a portion of the first flexible segment in response to receiving a pulling force on the separation thread.

31. The device according to claim 18, wherein one or more of the first and second segments have a cylindrical shape.

32. The device according to claim 18, wherein the flow opening comprises an elongate member having a cylindrical shape.

33. The device according to claim 32, wherein the elongate member extends between an aperture in the first segment to an aperture in the second segment, and wherein the apertures in the first and second segments are offset from one another.

34. The device according to claim 32, wherein the elongate member extends substantially perpendicularly between the first and second segments.

35. The device according to claim 18, wherein at least the portions of the first and second segments adjacent the ends of the flow opening are positioned in substantially parallel planes.

36. The device according to claim 18, wherein the first and second segments have substantially the same size and shape.

37. The device according to claim 18, wherein the second segment has at least one of a different size and shape than the first segment.

38. The device according to claim 18, wherein the device comprises a unitary component.

39. The device according to claim 18, wherein the device comprises two or more connectable components.

40. A kit for connecting first and second tissue structures comprising:
an implantable device comprising:
first and second substantially parallel and elongate flexible segments each having proximal and distal ends, wherein the first and second segments comprise a compliant material configured to be constricted for implantation within first and second tissue structures, respectively, the and wherein the material has a natural tendency to return to an unconstricted state such that, when implanted in the tissue structures, the material utilizes an internal fluid pressure within the respective tissue structure to conform to a shape of an inner surface of the tissue structure to provide a sealing contact with the inner surface,
a flow opening extending between the first and second segments along the elongate length of the segments at least a distance from each of the proximal and distal ends to fluidically couple the first and second tissue structures,
wherein the first and second segments are removably connectable to one another; and
a third elongate flexible segment having at least one of a different size and shape than the second segment and configured to be connected to the first segment in place of the second segment.

41. The kit of claim 40, further comprising:
a tool for implanting at least one of the first and second segments in the respective first or second tissue structure.

* * * * *